(12) United States Patent
Walther et al.

(10) Patent No.: US 9,890,400 B2
(45) Date of Patent: Feb. 13, 2018

(54) METHOD OF PRODUCTION OF 2,4-DIHYDROXYBUTYRIC ACID

(71) Applicant: ADISSEO FRANCE S.A.S., Antony (FR)

(72) Inventors: Thomas Walther, Lacroix-Falgarde (FR); Clèmentine Dressaire, Marseillan (FR); Hélène Cordier, Toulouse (FR); Jean-Marie Francois, Toulouse (FR)

(73) Assignee: ADISSEO FRANCE S.A.S., Antony (FR)

( * ) Notice: Subject to any disclaimer, the term of this patent is extended or adjusted under 35 U.S.C. 154(b) by 302 days.

(21) Appl. No.: 14/397,315

(22) PCT Filed: Apr. 25, 2013

(86) PCT No.: PCT/IB2013/001071
§ 371 (c)(1),
(2) Date: Oct. 27, 2014

(87) PCT Pub. No.: WO2013/160762
PCT Pub. Date: Oct. 31, 2013

(65) Prior Publication Data
US 2015/0159182 A1  Jun. 11, 2015

(30) Foreign Application Priority Data

Apr. 26, 2012 (WO) .............................. 2012/001123

(51) Int. Cl.
| | |
|---|---|
| C12P 7/42 | (2006.01) |
| C12N 9/00 | (2006.01) |
| C12N 9/88 | (2006.01) |
| C12P 7/52 | (2006.01) |
| C12N 9/04 | (2006.01) |
| C12N 9/02 | (2006.01) |
| C12N 9/10 | (2006.01) |

(52) U.S. Cl.
CPC ................ *C12P 7/42* (2013.01); *C12N 9/001* (2013.01); *C12N 9/0006* (2013.01); *C12N 9/0008* (2013.01); *C12N 9/13* (2013.01); *C12N 9/88* (2013.01); *C12N 9/93* (2013.01); *C12Y 101/01002* (2013.01); *C12Y 101/01061* (2013.01); *C12Y 102/01075* (2013.01); *C12Y 102/01076* (2013.01); *C12Y 208/03* (2013.01); *C12Y 401/03024* (2013.01); *C12Y 602/01009* (2013.01); *C12P 7/52* (2013.01); *C12Y 103/01028* (2013.01)

(58) Field of Classification Search
None
See application file for complete search history.

(56) References Cited

U.S. PATENT DOCUMENTS

| | | | |
|---|---|---|---|
| 2011/0045575 A1 | 2/2011 | Van Dien et al. | |
| 2013/0273623 A1* | 10/2013 | Walther | C12N 9/0006 435/146 |

FOREIGN PATENT DOCUMENTS

| | | |
|---|---|---|
| DE | 102006025821 A1 | 12/2007 |
| EP | 1167534 A2 | 1/2002 |
| WO | 2008046328 A1 | 4/2008 |
| WO | 2012/056318 A1 | 5/2012 |

OTHER PUBLICATIONS

Prather et al. (Curr. Opin. Biotechnol., 2008).*
Branden et al., "Introduction to Protein Structure Second Edition", Garland Publishing Inc., New York, 1999, p. 247.*
Kizer et al. (Appl. Environ. Microbiol., 2008).*
Seffernick et al. (J. Bacteriol. 183(8):2405-2410, 2001).*
Witkowski et al., Biochemistry, 38, 11643-11650, 1999.*
Oct. 28, 2014 International Preliminary Report on Patentability issued in International Application No. PCT/IB2013/001071.
Nov. 7, 2013 Search Report issued in International Application No. PCT/IB2013/001071.
Ford, Gordon et al. "Characterization of Yprlp from *Saccharomyces cerevisiae* as a 2-methylbutyraldehyde reductase". vol. 19, 1087-1096, 2002, Wiley InterScience.
Kockelkorn, Daniel et al. "Malonic Semialdehyde Reductase, Succinic Semialdehyde Reductase, and Succinyl-Coenzyme A Reductase from Metallosphaera sedula: Enzymes of the Autotrophic 3-Hydroxypropionate/4-Hydroxybutyrate Cycle in Sulfolobales". vol. 191, No. 20, 6352-6362, 2009, Journal of Bacteriology.

* cited by examiner

*Primary Examiner* — Suzanne M Noakes
*Assistant Examiner* — Jae W Lee
(74) *Attorney, Agent, or Firm* — Oliff PLC

(57) ABSTRACT

A method for the preparation of 2,4-dihydroxybutyric acid (2,4-DHB) including the successive steps of converting malate, succinyl-CoA and/or glyoxylate into malyl-CoA, converting malyl-CoA previously obtained into malate-4-semialdehyde, and converting malate-4-semialdehyde into 2,4-DHB using a DHB dehydrogenase.

13 Claims, 3 Drawing Sheets

METHOD OF PRODUCTION OF 2,4-DIHYDROXYBUTYRIC ACID

The present invention relates to a novel method of production of 2,4-dihydroxybutyric acid from malate and/or glyoxylate and/or succinyl-CoA by the implementation of a synthetic pathway that converts malate and/or glyoxylate and/or succinyl-CoA into malylCoA, malylCoA into malate-4-semialdehyde, and then converting said malate-4-semialdehyde into 2,4-dihydroxybutyric acid (2,4-DHB).

The carboxylic acids cited within the present application are equally named under their salt (e.g. 2,4-dihydroxyburyrate) or acid forms (e.g. 2,4-dihydroxybutyric acid).

2,4-dihydroxybutyric acid (equally 2,4-DHB or DHB) is a compound of considerable economic interest. DHB can be readily converted into α-hydroxy-γ-butyrolactone in aqueous media by adjusting the appropriate pH. α-hydroxy-γ-butyrolactone is a prominent precursor for the production of the methionine substitute, 2-hydroxy-4-(methylthio)-butyrate (HMTB), (US 2009/318715) which has a large market in animal nutrition. At present, α-hydroxy-γ-butyrolactone is derived from γ-butyrolactone by a multi-stage process that implies halogenation of the γ-butyrolactone in position α, and subsequent substitution of the halogen atom by a hydroxyl group in alkaline medium (US 2009/318715).

From growing oil prices, the need for the production of DHB from renewable resources arises. Microorganisms are capable of transforming biomass-derived raw material, e.g. sugars or organic acids, into a large variety of different chemical compounds (Werpy & Petersen, 2004). With the growing body of biochemical and genomic information, it is possible to modify microorganisms such that they overproduce naturally occurring metabolic intermediates with high yield and productivity (Bailey, 1991). Optimization of production microorganisms often requires rational engineering of metabolic networks which ensures, among others, overexpression of enzymes required for the biosynthesis of the metabolite of interest, and alleviation of product feedback inhibition. Another possibility is the implementation of novel enzymatic systems that catalyze the production of a metabolite of interest.

Metabolic engineering approaches and enzymatic catalyses require detailed knowledge of the biochemistry and regulation of the metabolic pathway leading to the metabolite of interest. In the case of 2,4-DHB production, this information is not available. Only few studies report the occurrence of 2,4-DHB in patients with succinic semialdehyde dehydrogenase deficiency (Shinka et al., 2002) without, however, identifying enzymatic reactions implicated in DHB production. The zymotic or enzymatic production of 2,4-DHB, therefore, requires (i) the identification of a thermodynamically feasible pathway which transforms an accessible precursor into 2,4-DHB, (ii) the identification or construction of enzymes that are capable to catalyze individual reaction steps in the pathway and (iii) the functional expression of the pathway enzymes in an appropriate production organism.

The present invention has as an objective to satisfy these needs.

Accordingly, one object of the present invention is a method of producing 2,4-DHB comprising a first step of converting malate and/or glyoxylate and/or succinyl-CoA in malyl-CoA, a second step of converting malyl-CoA in malate-4-semialdehyde and, a third step of converting malate-4-semialdehyde in 2,4-DHB.

Accordingly, one object of the present invention is a method of producing 2,4-DHB which comprises a first reaction (see FIG. 1), wherein malate is converted into malyl-CoA by the action of an enzyme which possesses malyl-CoA synthetase activity [1.1], and/or wherein succinyl-CoA is converted into malyl-CoA by the action of an enzyme having a succinyl-CoA:(L)-malate CoA transferase activity [1.2], and/or wherein glyoxylate is converted into malyl-CoA by the action of an enzyme which possesses malyl-CoA lyase activity [1.3]. In the second reaction [2], malyl-CoA is converted into malate-4-semialdehyde by the action of an enzyme which possesses malyl-CoA reductase activity. In the third reaction [3], malate-4-semialdehyde is converted into DHB by the action of an enzyme which possesses DHB dehydrogenase activity. More precisely, reaction [3] is catalysed by an enzyme bearing malate-4-semialdehyde reductase activity in the biosynthetic sense of the pathway.

Within another aspect of the invention, the first step of the method of producing 2,4-DHB involves an enzyme having malyl-CoA synthetase (equally named malate thiokinase or malate-coenzyme A ligase (ADP forming), EC 6.2.1.9), succinyl-CoA:(L)-malate CoA transferase (EC 2.8.3.-), or malyl-CoA lyase (EC 4.1.3.24) activity that transforms malate, succinyl-CoA, or glyoxylate, respectively, into malyl-CoA.

Said enzymes have been identified in methylotrophic bacteria that employ the serine cycle for fixation of formaldehyde (Chistoserdova et al., 2009; Smejkalová et al., 2010; Vuilleumier et al., 2009), in bacteria that rely on acetate assimilation pathways that are independent from the glyoxylate cycle and isocitrate lyase activity (Meister et al., 2005), and in bacteria that employ the 3-hydroxypropionate $CO_2$-fixation cycle for autotrophic growth (Zarzycki et al., 2009).

Proteins sharing homology with the above enzymes are also another aspect of the invention such as functional variants or functional fragments.

Malyl-CoA synthetase consists of two subunits, MtkA and MtkB. Therefore, according to the invention, proteins comprising a malyl-CoA synthetase activity designate all polypeptides having at least 30% of identity with the protein sequences of the malyl-CoA synthetase subunits MtkA and MtkB of *M. petroleiphilum* (YP 001022444 and YP 001022445) *Methylobacter extorquens* (YP002962851 and YP 002962852) or two subunits SucC and SucD of *M. capsulatus* (YP 114179 and YP 114180), preferentially at least 50% and more preferentially 70% of identity.

Malyl-CoA lyase is a homohexamer and found in bacteria that do not employ the glyoxylate cycle for acetate assimilation (Meister et al., 2005). Therefore, according to the invention, proteins comprising a malyl-CoA lyase activity designate all polypeptides having at least 30% of identity with the protein sequences of the malyl-CoA lyase, Mcl, of *Methylobacter extorquens, Rhodobacter capsulatus*, or *Streptomyces coelicolor*, preferentially at least 50 and more preferentially 70% of identity.

In a further aspect of the invention, the malyl-CoA lyase of the invention is represented by SEQ ID No. 1 or by any variant thereof.

Succinyl-CoA:(L)-malate CoA transferase consists of two subunits, SmtA and SmtB (Zarzycki et al., 2009)(Friedmann et al., 2006). Therefore, according to the invention, proteins having a succinyl-CoA:(L)-malate CoA transferase activity designate all polypeptides having at least 30% of identity with the protein sequences of the succinyl-CoA:(L)-malate CoA transferase subunits SmtA and SmtB of *Chloroflexus aurantiacus* (represented by SEQ ID No. 191 and SEQ ID No. 193 or encoded by SEQ ID No. 192 and SEQ ID No. 194), preferentially at least 50% and more preferentially 70% of identity.

More generally, within the meaning of the invention the identity between two protein sequences can be determined by methods well known by the skilled man in the art. Examples of such methods are the use of the CLUSTALW (Larkin et al., 2007) software (with the default parameters indicated on the website) or the BLAST alignment program (with the default parameters indicated on the website).

The term functional variant encompasses enzymes that may present substantial sequence modifications when compared to the sequences specifically described within the present application but that still retain the original enzymatic activity.

The term functional fragment, according to the invention, means that the sequence of the enzyme may comprise less amino acids than the original one but said truncated enzyme still retains the original enzymatic activity.

Improvement of said enzymes can be obtained by at least one mutation, said mutation(s) improving the activity and/or substrate affinity of the mutated enzyme for malate, succinyl-CoA, or glyoxylate respectively.

Within the present invention, the expression "improve the activity and/or substrate affinity" means that the enzyme before mutation was either
unable to use the substrate, and/or
synthesized the product of the reaction at a maximum specific rate at least three times lower, and/or
had an affinity for malate, succinyl-CoA or glyoxylate, malyl-CoA or malate-4-semialdehyde that was at least two more preferably three times lower.

The malyl-CoA synthetase and the malyl-CoA lyase activities can be measured by the enzymatic tests described by (Smejkalová et al., 2010) or (Meister et al., 2005), respectively. The succinyl-CoA:(L)-malate CoA transferase activity can be measured as described by (Friedmann et al., 2006)

Within a still further aspect, the second step of the method of producing 2,4-DHB according to the invention involves an enzyme having malyl-CoA reductase activity characterized in that it transforms malyl-CoA into malate-4-semialdehyde.

Said enzyme can be identified among enzymes having malonyl-CoA reductase, a succinyl-CoA reductase or reported 3-hydroxy-3-methylglutaryl-CoA (HMG-CoA) reductase, cinnamoyl-CoA reductase, or acetaldehyde dehydrogenase activity, or they can be obtained by modification of said enzymes.

Malonyl-CoA reductase (EC 1.2.1.75) and succinyl-CoA reductase (EC 1.2.1.76) were found in bacteria that possess a modified 3-hydroxypropionate cycle for carbon dioxide fixation (Alber et al., 2006; Kockelkorn & Fuchs, 2009), and in bacteria that employ an anaerobic succinate degradation pathway (Seedorf et al., 2008; Söhling & Gottschalk, 1993). HMG-CoA reductase (EC 1.1.1.38, EC 1.1.1.88) is part of the biosynthetic pathway of isoprenoids in eukaryotes and some bacteria. Cinnamoyl-CoA reductase (EC 1.2.1.44), is an enzyme implicated in lignin biosynthesis (Kawasaki et al., 2006). Acetaldehyde dehydrogenase (EC 1.2.1.10) is found in a large variety of bacteria and catalyses the entry into the ethanol producing pathway or the detoxification of acetaldehyde.

Within a further aspect of the invention, the malyl-CoA reductase is represented by ID No. 7, or SEQ ID No.10 or by any functional variant thereof or any functional fragment thereof.

Therefore, according to the invention, proteins having a malonyl-CoA reductase activity designate all polypeptides having at least 30% of identity with the protein sequences of the *Sulfolobus tokodaii* malonyl-CoA reductase, Mcr (SEQ ID No. 7). Preferentially they have at least 50% and more preferentially 70% of identity.

The malonyl-CoA reductase of *Chloroflexus auranthiacus* (SEQ ID No.189 encoded by SEQ ID No. 190) constitutes another aspect of the invention. Polypeptides having at least 30% of identity with the protein sequences of *Chloroflexus auranthiacus* are also part of the invention. Preferentially they have at least 50% and more preferentially 70% of identity.

Therefore, according to the invention, proteins having a succinyl-CoA reductase activity designate all polypeptides having at least 30% of identity with the protein sequences of the *Porphyromonas gingivalis* succinyl-CoA reductase, SucD (SEQ ID No. 10), or with the bifunctional *S. tokodaii* malonyl-CoA and succinyl-CoA reductase, Mcr (SEQ ID No. 7). Preferentially they have at least 50% and more preferentially 70% of identity.

The malyl-CoA reductase activity can be measured by the enzymatic test described in Example 2 (see "Enzymatic assay").

This enzyme activity can be improved by at least one mutation of an enzyme, said mutation(s) improving the activity and/or substrate affinity of the mutated enzyme for malyl-CoA or decreasing its activity on the natural substrate.

The present invention also encompasses modified malyl-CoA reductase having improved activities.

The malyl-CoA reductase according to the invention corresponds in a specific aspect to *Sulfolobus tokodaii* malonyl-CoA reductase comprising at least one mutation when compared to the wild type enzyme in at least one of the positions P111, L152, T154, L202, G203, D204, Y206, D207, K209, T210, T238, T239, D295, R318, wherein the naturally occurring amino acid in said positions is replaced by anyone of the other 19 naturally existing proteinogenic amino acids, that is by either alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

Within another aspect, the third step of the method of producing 2,4-DHB according to the invention involves a DHB dehydrogenase characterized in that it transforms malate-4-semialdehyde into 2,4-DHB, said enzyme bearing malate-4-semialdehyde reductase activity in the biosynthetic sense of the pathway.

Candidate DHB dehydrogenase enzymes that potentially already possess DHB dehydrogenase activity can be chosen from the class of beta-hydroxyacid dehydrogenases that act on C3, C4, or C5 compounds.

According to a still further aspect of the invention, said DHB dehydrogenase enzymes can be structurally and mechanistically related to β-hydroxyacid dehydrogenases such as tartronate semialdehyde reductases, succinate semialdehyde reductases, 4-hydroxybutyrate dehydrogenases, malonate semialdehyde reductases, methylbutyraldehyde reductases, zinc-type alcohol dehydrogenases, L-threonine-3-dehydrogenases, cinnamyl alcohol dehydrogenases, alcohol dehydrogenases, or homoserine dehydrogenases.

The present invention also deals with the use of a methylbutyraldehyde reductase, or of a succinic semialdehyde reductase (equally named as 4-hydroxybutyrate dehydrogenase), or of an alcohol dehydrogenase, to transform malate-4-semialdehyde in 2,4-DHB.

In another specific aspect of the invention, the DHB dehydrogenase corresponds to methylbutyraldehyde reductase (Ypr1) of *S. cerevisiae*, the succinic semialdehyde reductase of *M. sedula*, the 4-hydroxybutyrate dehydrogenase (4hbd) of *P. gingivalis*, or to the alcohol dehydrogenase (YqhD) of *Escherichia coli*.

In specific embodiments, said methylbutyraldehyde reductase is represented by SEQ ID No. 14, said succinic semialdehyde reductase is represented by SEQ ID No. 16, said 4-hydroxybutyrate dehydrogenase is represented by SEQ ID No. 187, said alcohol dehydrogenase is represented by SEQ ID No. 185. The DHB dehydrogenase activity can be measured by the enzymatic test described in Example 3 (see "Enzymatic assay").

The affinity of DHB dehydrogenase for malate-4-semi aldehyde can be increased by at least one mutation of an enzyme, said mutation(s) increasing the activity and/or substrate affinity of the mutated enzyme for malate-4-semi-aldehyde, and/or reducing the activity or affinity for its natural substrate by at least factor 2.

The DHB dehydrogenase according to the invention corresponds in a specific aspect to *M. sedula* succinic semialdehyde reductase (SEQ ID No. 16) comprising at least one mutation when compared to the wild type enzyme in at least one of the positions S40, N43, H39 T49, F85, Q108, L281 and N305 wherein the naturally occurring amino acid in said positions is replaced by anyone of the other 19 naturally existing proteinogenic amino acids, that is by either alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

As demonstrated in a non-exclusive example, the affinity of *M. sedula* succinic semialdehyde reductase for (L)-malate-4-semialdehyde was increased by introducing the double mutation H39R N43H by site-directed mutagenesis, as represented by SEQ ID No. 36. Simple mutants H39R (SEQ ID No. 32) and N43H (SEQ ID No. 34) are also encompassed by the present invention (Example 5).

DHB dehydrogenase can be used to transform malate-4-semialdehyde into 2,4-DHB, which constitutes a further aspect of the invention.

The nucleic acid sequence of genes can be adapted to the codon usage of the host organism thereby increasing the production of the heterologously expressed proteins. This constitutes a further aspect of the invention.

The synthesis of a synthetic gene coding for *M. sedula* succinic semialdehyde reductase H39R N43H whose nucleotide sequence was optimized for the expression of said enzyme in *E. coli* as represented by SEQ ID No. 38 is a further aspect of the invention.

In a still further aspect, the present invention also deals with nucleic acids, and more particularly with isolated nucleic acid sequences encoding malyl-CoA synthetase.

In a still further aspect, the present invention deals with isolated nucleic acid sequences encoding malyl-CoA lyase and more specifically by SEQ ID No.2.

In a still further aspect, the present invention deals with isolated nucleic acid sequences encoding malyl-CoA reductase and more specifically by SEQ ID No. 8, SEQ ID No.11, or SEQ ID No.190.

In a still further aspect, the present invention also deals with isolated nucleic acid sequences encoding a DHB dehydrogenase as described above.

In another aspect, said nucleic acid is represented by SEQ ID No. 15, SEQ ID No. 17, SEQ ID No. 37, SEQ ID No. 186 or SEQ ID No. 188.

In accordance with this invention, a "nucleic acid sequence" refers to a DNA or RNA molecule in single or double stranded form, preferably a DNA molecule. An "isolated DNA", as used herein, refers to a DNA which is not naturally-occurring or no longer in the natural environment wherein it was originally present, e.g., a DNA coding sequence associated with other regulatory elements in a chimeric gene, a DNA transferred into another host cell, or an artificial, synthetically-made DNA sequence having a different nucleotide sequence compared to any naturally-occurring DNA sequence.

The present invention also relates to a chimeric gene comprising, functionally linked to one another, at least one promoter which is functional in a host organism, a polynucleotide encoding anyone of the malyl-CoA synthetase or malyl-CoA lyase, malyl-CoA reductase, malonyl-CoA reductase, succinyl-CoA reductase or DHB dehydrogenase activities as defined according to the invention, and a terminator element that is functional in the same host organism. The various elements which a chimeric gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art. The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, the promoters used for expression in bacteria may be chosen from the promoters mentioned below. For expression in *Escherichia coli* mention may be made of the lac, trp, lpp, phoA, recA, araBAD, prou, cst-I, tetA, cadA, nar, tac, trc, lpp-lac, Psyn, cspA, PL, PL-9G-50, PR-PL, T7, [lambda]PL-PT7, T3-lac, T5-lac, T4 gene 32, nprM-lac, VHb and the protein A promoters or else the Ptrp promoter (WO 99/64607). For expression in Gram-positive bacteria such as *Corynebacteria* or *Streptomyces*, mention may be made of the PtipA or PS1 and PS2 (FR91/09870) promoters or those described in application EP0629699A2. For expression in yeasts and fungi, mention may be made of the *K. lactis* PLAC4 promoters or the *K. lactis* Ppgk promoter (patent application FR 91/05294), the *Trichoderma* tef1 or cbh1 promoter (WO 94/04673), the *Penicillium* his, csl or apf promoter (WO 00/68401) and the *Aspergillus* gla promoter.

According to the invention, the chimeric gene may also comprise other regulatory sequences, which are located between the promoter and the coding sequence, such as transcription activators (enhancers).

As such, the chimeric gene of the invention comprises, in a specific embodiment at least, in the direction of transcription, functionally linked, a promoter regulatory sequence which is functional in a host organism, a nucleic acid sequence encoding the malyl-CoA synthetase, and/or the succinyl-CoA:(L)-malate-CoA transferase, and/or the malyl-CoA lyase, the malyl-CoA reductase and the DHB dehydrogenase of the invention and a terminator regulatory sequence which is functional in said host organism.

The present invention also relates to a cloning and/or expression vector comprising a chimeric gene according to the invention or a nucleic acid sequence of the invention. The vector according to the invention is of use for transforming a host organism and expressing in this organism anyone of the malyl-CoA synthetase, and/or the succinyl-CoA:(L)-malate CoA transferase, and/or the malyl-CoA lyase, the malyl-CoA reductase and/or DHB dehydrogenase. This vector may be a plasmid, a cosmid, a bacteriophage or a virus. Preferentially, the transformation vector according to the invention is a plasmid. Generally, the main qualities of this vector should be an ability to maintain itself and to self-replicate in the cells of the host organism, in particular by virtue of the presence of an origin of replication, and to express anyone of the malyl-CoA synthetase, and/or the succinyl-CoA:(L)-malate CoA transferase and/or the malyl-CoA lyase, the malyl-CoA reductase and/or DHB dehydrogenase therein. For the purpose of stable transformation of a host organism, the vector may also integrate into the genome. The choice of such a vector, and also the techniques of insertion of the chimeric gene according to the invention into this vector and are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. According to a particular embodiment of the invention, the host organism to be transformed is a bacterium, a yeast, a fungus. Among the selectable markers which can be used, mention may be made of markers containing genes for resistance to antibiotics, such as, for example, the hygromycin phosphotransferase gene. Other markers may be genes to complement an auxotrophy, such as the pyrA, pyrB, pyrG, pyr4, arg4, argB and trpC genes, the molybdopterin synthase gene or that of acetamidase. Mention may also be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to transformed host organisms containing at least one chimeric gene according to the invention, either integrated into their genome or carried on an extra-chromosomal genetic element, for example a plasmid. In a more specific aspect of the invention, the transformed host organism comprises a nucleic acid of the invention encoding a polypeptide having malyl-CoA synthetase activity, and/or succinyl-CoA:(L)-malate-CoA transferase and/or malyl-CoA lyase activity or a chimeric gene comprising a nucleic acid encoding a polypeptide having malyl-CoA synthetase activity, and/or succinyl-CoA:(L)-malate CoA transferase and/or a malyl-CoA lyase activity or an expression vector comprising a nucleic acid encoding a polypeptide having malyl-CoA synthetase activity, and/or succinyl-CoA:(L)-malate CoA transferase and/or a malyl-CoA lyase activity, and/or a nucleic acid encoding a polypeptide having malyl-CoA reductase activity, or a chimeric gene comprising a nucleic acid encoding a polypeptide having malyl-CoA reductase activity or an expression vector comprising a nucleic acid encoding a polypeptide having malyl-CoA reductase activity, and/or a nucleic acid encoding a polypeptide having DHB dehydrogenase activity, a chimeric gene comprising a nucleic acid encoding a polypeptide having DHB dehydrogenase activity or an expression vector comprising a nucleic acid encoding a polypeptide having DHB dehydrogenase activity.

The activity of heterologously enzymes in the host organism is often limited by their poor solubility and the formation of inclusion bodies. Therefore, the present invention also relates to chimeric proteins in that a functional enzyme is physically fused to another protein or peptide (equally named fusion protein) in order to increase the activity of said enzyme upon expression in the host organism. Such fusion proteins are known in the art and are commonly selected among the following non-exclusive examples: maltose binding protein, Mbp, thioredoxin, ThrX, glutathione-S-transferase, Gst, transcription termination factor, NusA.

The term "host organism" is intended to mean any lower monocellular organism into which the chimeric gene(s), nucleic acid(s) or vector(s) according to the invention may be introduced in order to produce 2,4-DHB. Preferably, the host organism is a microorganism, in particular a fungus, for example of the *Penicillium*, *Aspergillus* and more particularly *Aspergillus flavus*, *Chrysosporium* or *Trichoderma* genus, a yeast, in particular of the Saccharomycetaceae, Pichiaceae or Schizosaccharomycetaceae, most preferentially *Saccharomyces cerevisiae*, *Schizosaccharomyces pombe*, *Kluyveromyces lactis*, *Kluyveromyces marxianus*, or *Pichia jadinii*, *Pichia stipitis* or *Pichia pastoris*, a bacterium, preferentially selected among Enterobacteriaceae, Clostridiaceae, Bacillaceae, Streptomycetaceae, Streptococcaceae, Methylobacteriacae, and Corynebacteriaceae, most preferentially *Escherichia coli*, *Bacillus subtilis*, *Corynebacterium glutamicum*, *Clostridium acetobutylicum*, *Methylobacterium extorquens*, or *Lactococcus lactis*.

The host organism can be a host organism that naturally overproduces malate or succinate from sugars such as glucose or a host organism that was engineered to overproduce malate or succinate from sugars such as glucose and in which all potential membrane transporters that facilitate export of organic acids, such as malate, pyruvate, succinate, and fumarate have been deleted. The host organism can be an organism that was engineered to overproduce DHB and in which membrane transporters that facilitate export of organic acids such as malate, pyruvate, succinate, and fumarate have been deleted. Examples of permeases that facilitate export of malate and other organic acids are Mae1 from *Schizosaccharomyces pombe* (Camarasa et al., 2001) (Grobler et al., 1995), DctA from *Bacillus subtilis* (Groeneveld et al., 2010), Dct 1-4 from coil, Jen1 from *S. cerevisiae* (Akita et al., 2000). For an expert, it will be possible to identify candidate permeases in *E. coli* based on sequence identity. These constructions will serve to keep malate and other organic acids inside the cell to make them available for DHB production.

The expression "transformed host organism" is intended to mean a host organism which has incorporated into its genome, or in an extra chromosomal genetic element, for example a plasmid, at least one chimeric gene according to the invention, and consequently produces any one of malyl-CoA synthetase, malyl-CoA lyase, malyl-CoA reductase and/or DHB dehydrogenase in cell interior or in a culture medium. To obtain the host organisms according to the invention, those skilled in the art may use one of the many known transformation methods.

One of these methods consists in bringing the cells of the host organisms to be transformed into contact with polyethylene glycol (PEG) and with the vectors according to the invention. Electroporation is another method, which consists in subjecting the cells to be transformed and the vectors of the invention to an electric field. Another method consists in directly injecting the vectors into the cells or the tissues by microinjection. The "biolistic" method may be used. It consists in bombarding cells or tissues with particles onto which the vectors of the invention are adsorbed (U.S. Pat. No. 4,945,050).

Several methods for transforming bacteria are described in the literature for *Escherichia coli* and other Gram-negative bacteria. Conjugation may also be used. For Gram-positive bacteria, electroporation may be used, and also protoplast transformation, in particular for bacteria of the *Streptomyces* genus.

Several methods for transforming fungi are also described in the literature. Protoplast transformation with PEG is described for *Aspergillus* in EP 0260762, and an adaptation of this method to the species *Penicillium funiculosum* is described in WO 00/36120. Transformation by restriction enzyme mediated integration, or REMI, is also known, as is protoplast transformation using bacteria of the *Agrobacterium* genus. Techniques for transforming yeasts are also described in the literature.

In a further aspect, the invention deals with a process of production of 2,4-DHB comprising the step of cultivating a transformed microorganism of the invention.

For the production of DHB various carbohydrates could be utilized individually or as a mixture such as glucose, fructose, sucrose, molasses, maltose, blackstrap molasses, starch hydrolysate (glucose, oligosaccharides), lactose, maltose, starch and starch hydrolysates, cellulose, cellulose hydrolysate, glycerol, acetate and certain hydrocarbons, oils and fats such as soy bean oil, sunflower oil, groundnut oil and coconut oil as well as fatty acids such as e.g. palmitic acid, stearic acid and linoleic acid. Those substances may be used individually or as mixtures.

Various sources of nitrogen could be utilized individually or as mixtures for the commercial and pilot scale production, including inorganic compounds such as gaseous and aqueous ammonia, ammonium salts of inorganic or organic acids such as ammonium sulphate, ammonium nitrate, ammonium phosphate, ammonium chloride, ammonium acetate and ammonium carbonate. Alternatively, natural nitrogen containing organic materials like soybean-hydrolysate, soy protein HCl-hydrolysate (total nitrogen of about 7%), soy bean meal, soybean cake hydrolysate, corn steep liquor, casein hydrolysate, yeast extract, meat extract, malt extract, urea, peptones and amino acids may also be utilized The production process can be carried out under aerobic, anaerobic, and oxygen limited conditions. It can be carried out as a fed-batch process or a batch process.

Said production of 2,4-DHB can be made by cultivating the host organism in media where malate (or another organic acid such as pyruvate, succinate, or fumarate) was added alone or together with another carbon source that ensures growth. Malate (and other organic acids) can be added either directly, or by designing a two-stage fermentation process where malate (or other organic acids) is produced in a first process stage by a malate-overproducing microorganism, and 2,4-DHB production is realised in the following stage by a host organism according to the invention.

Product separation and purification is very important factor enormously affecting overall process efficiency and product costs. Methods for product recovery commonly comprise the steps cell separation, as well as product purification, concentration and drying, respectively.

Cell Separation

Ultra filtration and centrifugation can be used to separate cells from the fermentation medium. Cell separation from fermentation media is often complicated by high medium viscosity. Therefore, we can add additives such as mineral acids or alkali salts, or heating of the culture broth to optimize cell separation.

Product Recovery

A variety of ion-exchange chromatographic methods can be applied for the separation of DHB either before or after biomass removal. They include the use of primary cation exchange resins that facilitate separation of products according to their isoelectric point. Typically, the resin is charged with the solution, and retained product is eluted separately following increase of pH (e.g. by adding ammonium hydroxide) in the eluent. Another possibility is the use of ion-exchange chromatography using fixed or simulated moving bed resins. Different chromatographic steps may have to be combined in order to attain adequate product purity. Those purification methods are more economical compared with a costly crystallization step, also providing additional advantages and flexibility regarding the form of final product.

Product Concentration and Drying

The purification process can also comprises a drying step which may involve any suitable drying means such as a spray granulator, spray dryer, drum dryer, rotary dryer, and tunnel dryer. Concentrated DHB solutions can be obtained by heating fermentation broths under reduced pressure by steam at 130° C. using a multipurpose concentrator or thin film evaporator.

Efficient production of DHB can be ensured by optimizing carbon flux repartitioning in the metabolic network of the host organism and by ensuring sufficient NADPH and ATP supply for the three enzymes of the DHB pathway. Channeling of carbon flux into a desired metabolic pathway and supply of NAD(P)H cofactor is commonly facilitated by deleting or alleviating competing natural fermentative pathways. Nonexclusive examples are the optimization of malate production in *S. cerevisiae* by impeding the formation of ethanol (by the deletion of pyruvate decarboxylases (Zelle et al., 2008)(Zelle et al., 2010).

the optimization of succinate or malate production in *E. coli* by impeding the formation of lactate (e.g. deletion of ldhA), the formation of acetate (e.g. deletion of pta, ackA), the formation of ethanol (e.g. deletion of adhE), the formation of formate (e.g. deletion of pflB, focA), the oxidation of pyruvate (e.g. deletion of poxB), the degradation of malate (deletion of maeB and scfA), the formation of succinate (e.g. deletion of frdBC), the formation of methylglyoxal (deletion of mgsA) (Jantama et al., 2008a) (Jantama et al., 2008b) (Lin et al., 2005) (Zhang et al., 2011) (Sanchez et al., 2005).

the deletion of phosphoglucose isomerase, pgi, to channel carbon flux across the pentose phosphate pathway thereby increasing NADPH availability for biosynthetic reactions (Auriol et al., 2011).

Another possibility to increase carbon flux and ATP supply for the production of organic acids is the engineering of the phosphoenolpyruvate (PEP)/pyruvate/oxaloacetate branch node (reviewed in (Sauer & Eikmanns, 2005)). Nonexclusive examples for metabolic engineering strategies that ensure the increase of carbon flux from phosphoenolpyruvate to oxaloacetate are:

the optimization of malate production in *S. cerevisiae* by impeding the function of pyruvate kinase and increasing the activity of PEP carboxykinase (Zelle et al., 2010).

the optimization of succinate production in *E. coli* by increasing the activity of natural or heterologously expressed PEP carboxylase, PEP carboxykinase, or pyruvate carboxylase (Millard et al., 1996) (Sanchez et al., 2005) (Zhang et al., 2011).

Another possibility to increase carbon flux and ATP supply for the production of organic acids in *E. coli* and other bacteria employing the PEP-consuming phosphotransferase system (PTS) for the initial phosphorylation step of glucose is the deletion of essential components of the PTS system (for example ptsI or ptsG) (Lin et al., 2005) (Zhang et al., 2009). To ensure further glucose uptake in mutants carrying deleterious mutations of the PTS system, the activity of alternative glucose uptake systems (e.g. GalP) has to be ensured.

Another possibility to increase carbon flux into the desired pathways for the production of organic acids is the engineering of the citric acid and glyoxylate cycle. Non-exclusive examples are the optimization of succinic acid production in *E. coli* by increasing the activity of isocitrate lyase (deletion of transcriptional repressor iclR) (Lin et al., 2005) (Sanchez et al., 2005) (Lin et al., 2005; Sanchez et al., 2005a).

the optimization of succinic acid production by the deletion of isocitrate dehydrogenase, and/or succinate dehydrogenase (Lin et al., 2005).

Another possibility to increase the availability of malate, glyoxylate and acetyl-CoA, which are the substrates of the entry reactions into the DHB-producing pathways, is the attenuation of aspartate transaminase (aspC, tyrB), fumarase (fumABC), fumarate reductase (frdBC), malate synthase (aceB) and glyoxylate reductase (ghrAB) enzymes.

In another metabolic setting it is possible to produce the 2,4-DHB precursor malate exclusively via the Krebs cycle and the glyoxylate shunt. This setting requires deletion of the cytosolic and membrane bound malate dehydrogenases, mdh and mqo, respectively. The approach largely avoids potential leakage of carbon flux into aspartate and its derivatives.

Another possibility to increase carbon flux into the desired pathways for the production of 2,4-DHB is the expression of appropriate pyruvate dehydrogenases and citrate synthases in the production organism. Natural pyruvate dehydrogenase and citrate synthase of *E. coli* are inhibited by high intracellular NADH concentrations rendering these enzymes less active under anaerobic conditions. In *E. coli*, the expression of a pyruvate dehydrogenase mutant that is insensitive to NADH resulted in the overproduction of acetyl-CoA under anaerobic conditions and modified carbon flux repartitioning between the fermentative end-products (acetate, lactate, ethanol, formate, and pyruvate) (Wang et al., 2010). The heterologous expression of the *Bacillus subtilis* citrate synthase which is insensitive to NADH increased succinic acid production in engineered *E. coli* strains (Sanchez et al., 2005). In combination with the above described mutations, the use of the appropriate pyruvate dehydrogenases and citrate synthases (NADH sensitive or insensitive) enables the tuning of carbon flux repartitioning between glyoxylate and citric acid cycle reactions and fermentative pathways under anaerobic and aerobic conditions.

Another possibility to increase carbon flux through the DHB pathway is the deletion of enzymatic reactions that may degrade the pathway intermediates malyl-CoA, or 4-malate semialdehyde. Candidate enzymes that may degrade malate semialdehyde are succinic semialdehyde dehydrogenases (sad, gabD), and other dehydrogenases that are able to oxidize short and medium carbon chain molecules with terminal aldehyde groups. Furthermore, it is known that malyl-CoA may be degraded by citrate synthase.

Another possibility to increase 2,4-DHB productivity of the host organism is the deletion of metabolic reactions that degrade 2,4-DHB. 2,4-DHB is a competitive inhibitor of malic enzyme, thus, having comparatively high affinity for the active site of this enzyme (Rognstad & Katz, 1979). Therefore, 2,4-DHB may be recognized by other enzymes and potentially degraded. These enzymes can be identified and deleted from the host organism.

When 2,4-DHB production is based on addition of malate or other organic acids, the 2,4-DHB-producing microorganisms should functionally express a membrane transport protein that facilitates uptake of malate (or other organic acids such as pyruvate, succinate, etc).

The transformed host organisms of the invention may further contain an additional pathway of synthesizing 2,4-DHB, said host organism comprises at least one chimeric gene, either integrated into their genome or carried on an extra-chromosomal genetic element, for example a plasmid encoding a malate kinase or a chimeric gene comprising a nucleic acid encoding a malate kinase or an expression vector comprising a nucleic acid encoding a malate kinase, and/or a nucleic acid encoding a malate semialdehyde dehydrogenase, or a chimeric gene comprising a nucleic acid encoding a malate semialdehyde dehydrogenase or an expression vector comprising a nucleic acid encoding a malate semialdehyde dehydrogenase, and/or a nucleic acid encoding a DHB dehydrogenase, a chimeric gene comprising a nucleic acid encoding a DHB dehydrogenase or an expression vector comprising a nucleic acid encoding a DHB dehydrogenase. Said enzymes are described in the International patent application WO 2012/056318.

The following examples illustrate the invention. These examples are for purposes of illustration only and are not to be construed as limiting the scope of the invention in any manner.

EXAMPLES

Figure 1:
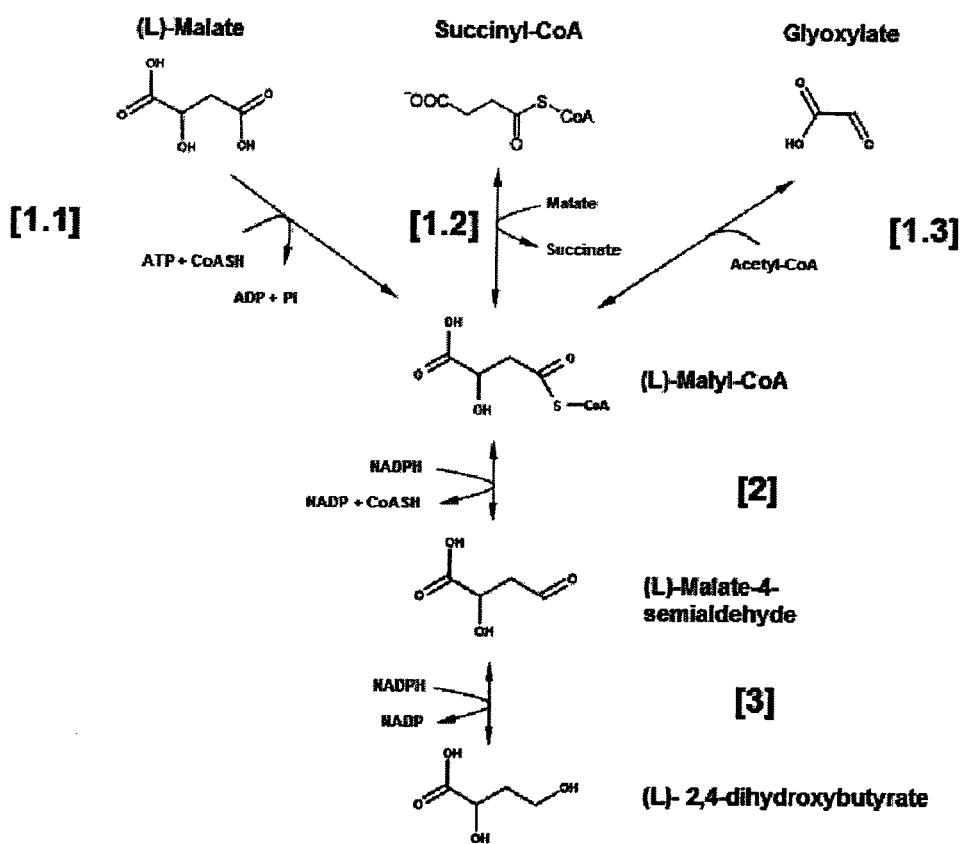
FIG. 1: (i) Reaction scheme that describes the conversion of (L)-malate, succinyl-CoA, or glyoxylate into (L)-2,4-dihydroxybutyrate (2,4-DHB).

Example 1: Demonstration of Malyl-CoA Lyase Activity

Construction of plasmids containing wild-type genes coding for malyl-CoA lyase: The DNA sequences of the mcl genes coding for malyl-CoA lyase in *M. extorquens* (Arps et al., 1993) and *Rhodobacter capsulatus* (Meister et al., 2005) were optimized for the expression in *Escherichia coli* using the GENEius software (Eurofins). The optimized sequences were synthesized by Eurofins MWG OPERON® adding NheI and EcoRI restriction sites upstream of the start codon and downstream of the stop codon of mcl, respectively, which allowed direct cloning of the synthesized DNA fragments into the pET28a+ vector (Novagen) using T4 DNA ligase (Biolabs). Ligation products were transformed into *E. coli* DH5α cells, amplified, and the plasmids pET28-Mex-mcl (expressing the malyl-CoA lyase from *M. extorquens*) and pET28-Rca-mcl (expressing the malyl-CoA lyase from *R. capsulatus*) were isolated using standard genetic protocols (Sambrook et al., 1989). NCBI and Integrated Genomics references of the utilized mcl protein sequences, and the references for the corresponding natural and synthetic DNA sequences are listed in Table 1.

TABLE 1

References to proteins from different organisms having annotated malyl-CoA lyase activity, and references to natural and optimized DNA sequences.

| Organism | Protein | NCBI/Integrated Genomics accession number | Natural DNA sequence | Optimized DNA sequence |
|---|---|---|---|---|
| *M. extorquens* | Mcl SEQ ID No. 1 | YP 002962854 | SEQ ID No. 2 | SEQ ID No. 3 |

Expression of Enzymes:
*E. coli* BL21 (DE3) cells were transformed with the appropriate plasmids using standard genetic protocols (Sambrook et al., 1989). Enzymes with an N-terminal hexa-His tag were expressed in 250 mL LB cultures that were inoculated from an overnight culture at $OD_{600}$ of 0.1 and grown to $OD_{600}$ of 0.6 before protein expression was induced by addition of 1 mM isopropyl β-D-1-thiogalactopyranoside (IPTG) to the culture medium. After 3 h of protein expression, cells were harvested by centrifugation at 13000 g for 10 min and the supernatant is discarded. Cell pellets were stored at −20° C. until further analysis. Growth and protein expression were carried out at 37° C. Culture media contained 50 μg/mL kanamycin.

Purification of Enzymes:
Frozen cell pellets of expression cultures were resuspended in 0.5 mL of breakage buffer (50 mM Hepes, 300 mM NaCl, pH 7.5) and broken open by four successive rounds of sonication (sonication interval: 20 sec, power output: 30%, sonicator: Bioblock Scientific, VibraCell™ 72437). Cell debris were removed by centrifuging the crude extracts for 15 min at 4° C. at 13000 g and retaining the clear supernatant. RNA and DNA were removed from the extracts by adding 15 mg/mL streptomycin (Sigma), centrifuging the samples at 13000 g for 10 min at 4° C. and retaining the supernatant. Clear protein extract was incubated for 20 min at room temperature (1 h at 4° C.) with 0.3 (0.75 mL) (bed volume) of Talon™ Cobalt affinity resin (Clontech). The suspension was centrifuged at 700 g in a table top centrifuge and supernatant was removed. The resin was washed with 10 bed volumes of wash buffer (50 mM Hepes, 300 mM NaCl, 15 mM Imidazole, pH 7.5) before proteins were eluted with 0.5 mL of elution buffer (50 mM Hepes, 300 mM NaCl, 200 mM Imidazole, pH 7.5). Purity of eluted enzymes was verified by SDS-PAGE analysis. Protein concentrations were estimated with the method of Bradford.

Enzymatic Assays:
Malyl-CoA lyase activity was assayed using a method adapted from (Meister et al., 2005). Malyl-CoA synthesis by malyl-CoA lyase was coupled to the citrate synthase-catalyzed release of coenzyme A which was monitored by its spontaneous reaction with DTNB.

Reaction Scheme

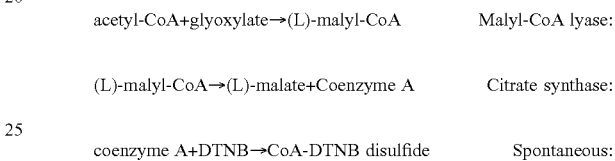

The reaction mixture according to Assay 1 contained 50 mM MOPS/KOH (pH 7.5), 0.25 mM DTNB, 5 mM $MgCl_2$, 1 mM acetyl-CoA, 20 U/mL citrate synthetase (all products from Sigma), and appropriate amounts of purified malyl-CoA lyase or cell extract. Reactions were started by adding 10 mM glyoxylate. Enzymatic assays were carried out at 37° C. in 96-well flat bottomed microtiter plates in a final volume of 250 μL. The reactions were followed by the characteristic absorption of DNTB at 412 nm ($\epsilon_{DNTB+CoA}$=13.6 $mM^{-1}$ $cm^{-1}$) in a microplate reader (Bio-Rad 680XR).

Purified malyl-CoA lyase from *M. extorquens* characterized had a Vmax of 36 μmol/(min mg prot), and a Km on glyoxylate of 0.5 mM.

Example 2: Demonstration of Malyl-CoA Reductase Activity

Construction of plasmids containing wild-type genes coding for malonyl-CoA reductase and succinyl-CoA reductase: The DNA sequence of the mcr gene coding for malyl-CoA reductase in *Sulfolobus tokodaii* str 7 (Alber et al., 2006) was optimized for the expression in *Escherichia coli* using the GENEius software (Eurofins). The optimized mcr sequence, and the natural DNA sequence of the sucD gene coding for succinyl-CoA reductase in *Porphyromonas gingivalis* W83 were synthesized by Eurofins MWG OPERON® adding NheI and EcoRI restriction sites upstream of the start codon and downstream of the stop codon of mcr, respectively, which allowed direct cloning of the synthesized DNA fragments into the pET28a+ vector (Novagen) using T4 DNA ligase (Biolabs). Ligation products were transformed into *E. coli* DH5α cells, amplified, and the plasmids, pET28-St-mcr (expressing the malonyl-CoA reductase from *S. tokodaii*), and pET28-Pgi-sucD (expressing the succinyl-CoA reductase from *P. gingivalis*), were isolated using standard genetic protocols (Sambrook et al., 1989). NCBI references of the utilized mcr and sucD protein sequences, and the references for the corresponding natural and synthetic DNA sequences are listed in Table 2.

TABLE 2

References to proteins from different organisms having annotated
malyl-CoA reductase or succinyl-CoA reductase activity, and
references to natural and optimized DNA sequences.

| Organism | Protein | NCBI/Integrated Genomics accession number | Natural DNA sequence | Optimized DNA sequence |
|---|---|---|---|---|
| S. tokodaii | St-Mcr SEQ ID No. 7 | NP 378167 | SEQ ID No. 8 | SEQ ID No. 9 |
| P. gingivalis | Pg-SucD SEQ ID No. 10 | AAQ65862 | SEQ ID No. 11 | |

Expression and purification of Pg-SucD was carried out as described in Example 1 using plasmid pET28-Pgi-sucD.

The St-mcr gene was amplified from plasmid pET28-St-mcr using primers 5'-TATAATGAGCTCGTTTAACTTTAAGAAGGAGATATACCATGATTCTGATGC GCCGT-3'(SEQ ID No. 12) and 5'-TATAATGGATCCCTCGAATTCTTACTTCTC-3' (SEQ ID No. 13) which added a SacI and a BamHI restriction site upstream of the start codon and downstream of the stop codon, respectively. The PCR fragment was ligated into the pACT3 expression vector using the SacI and BamHI restriction sites. The resulting plasmid pACT3-St-Mcr was transformed into strain E. coli MG1655. The resulting expression strain was cultivated on mineral medium at 37° C. One liter mineral medium contained 20 g glucose, 18 g $Na_2HPO_4*12 H_2O$, 3 g $KH_2PO_4$, 0.5 g NaCl, 2 g $NH_4Cl$, 0.5 g $MgSO_4*7 H_2O$, 0.015 $CaCl_2*2 H_2O$, 1 mL of 0.06 mol/L $FeCl_3$ stock solution prepared in 100 times diluted concentrated HCl, 2 mL of 10 mM thiamine HCl stock solution, 20 g MOPS, 50 µg kanamycin sulphate (and 25 µg chloramphenicol when necessary), and 1 mL of trace element solution (containing per liter: 0.04 g $Na_2EDTA*2H_2O$, 0.18 g $CoCl_2*6 H_2O$, $ZnSO4*7 H_2O$, 0.04 g $Na_2MoO4*2 H_2O$, 0.01 g $H_3BO_3$, 0.12 g $MnSO_4*H_2O$, 0.12 g $CuCl_2*H2O$.). Medium pH was adjusted to 7 and medium was filter-sterilized.

When the exponentially growing culture reached an OD (600 nm) of 0.6, 1 mM IPTG was added and cultures were incubated at 20° C. during 14 h before harvesting the cells by centrifugation (13000×g, 10 min). After discarding the supernatant cell pellets were stored at −20° C.

To purify St-Mcr, frozen cell pellets of expression cultures were resuspended in 0.5 mL of breakage buffer (50 mM Hepes, 300 mM NaCl, pH 7.5) and broken open by four successive rounds of sonication (sonication interval: 20 sec, power output: 30%, sonicator: Bioblock Scientific, Vibra-Cell™ 72437). Cell debris were removed by centrifuging the crude extracts for 15 min at 4° C. at 13000×g and retaining the clear supernatant. Native proteins of E. coli were removed by heat precipitation at 85° C. during 30 min followed by centrifugation at 13000×g. Purity of the protein preparations was analysed by SDS-page analysis which showed only one band corresponding to the expected size of the St-Mcr protein.

Enzymatic Assays:

Malyl-CoA reductase activity was assayed in the reductive and in the oxidative sense of the reaction employing Assay 1 or Assay 2, respectively.

Assay 1 (Reaction Scheme):

glyoxylate+acetyl-CoA→malyl-CoA+acetate    Malyl-CoA lyase:

(L)-Malyl-CoA+NADPH→(L)-Malate semialdehyde+Coenzyme A+NADP    Malyl-CoA reductase:

Assay 2 (Reaction Scheme):

(L)-Malate semialdehyde+Coenzyme A+NADP→(L)-Malyl-CoA+NADPH

The reaction mixture according to Assay 1 contained 50 mM MOPS/KOH (pH 7.5), 10 mM glyoxylate, 4 mM acetyl-CoA, 5 mM $MgCl_2$, 0.25 mM NADPH (all products from Sigma), 5 U/mL of malyl-CoA lyase, and appropriate amounts of purified malyl-CoA reductase or cell extract. Reactions were started by adding glyoxylate. Enzymatic assays were carried out at 37° C. in 96-well flat bottomed microtiter plates in a final volume of 250 µL. The reactions were followed by the characteristic absorption of NADPH at 340 nm ($\epsilon_{NADPH}$=6.22 $mM^{-1}$ $cm^{-1}$) in a microplate reader (BioRad 680XR).

The reaction mixture according to assay 2 contained 200 mM HEPES (pH 9), 5 mM $MgCl_2$, 1 mM NADP, 0.5 mM coenzyme A (all products from Sigma), and appropriate amounts of purified malyl-CoA reductase. Reactions were started by adding 5 mM (L)-malate semialdehyde. Enzymatic assays were carried out at 37° C. in 96-well flat bottomed microtiter plates in a final volume of 250 µL. The reactions were followed by the characteristic absorption of NADPH at 340 nm ($\epsilon_{NADPH}$=6.22 $mM^{-1}$ $cm^{-1}$) in a microplate reader (BioRad 680XR). Unstable malate semialdehyde was produced freshly prior to the enzymatic tests by the deprotection of the stable malate semialdehyde derivative 2-[(4S)-2,2-dimethyl-5-oxo-1,3-dioxolan-4-yl]acetaldehyde (DMODA) (provided by Activation®). Malate semialdehyde was obtained by dissolving appropriate amounts of DMODA in 2 M hydrochloric acid, short heating of the suspension to boiling temperature, and leaving the hot suspension for 15 min at room temperature. The released acetone was evaporated at 35° C. and 50 mbar in a rotary evaporator. The pH of the malate semialdehyde solution was fixed at 3.5 using sodium bicarbonate.

Results listed in Tables 3 and 4 demonstrate malyl-CoA reductase activity for malonyl-CoA reductase, Mcr, of S. tokodaii and succinyl-CoA reductase, SucD, of P. gingivalis.

TABLE 3

Kinetic parameters for the reductive sense of reaction (malonyl-CoA reductase and succinyl-CoA reductase activities were estimated by directly adding the substrates malonyl-CoA or succinyl-CoA to the reaction mixture).

| | Substrate | | | | | |
|---|---|---|---|---|---|---|
| | Malonyl-CoA | | Succinyl-CoA | | Malyl-CoA | |
| Enzyme | Vmax [µmol/(min mg)] | Km [mM] | Vmax [µmol/(min mg)] | Km [mM] | Vmax [µmol/(min mg)] | Km [mM] |
| St-Mcr | 0.67 ± 0.15 | nd | 0.98 ± 0.17 | 0.2 | 0.24 ± 0.045 | nd |
| Pg-SucD | nd | nd | 1 | 1 | 0.025 | nd |

TABLE 4

Kinetic parameters for the oxidative sense of reaction

| | Substrate | | | |
|---|---|---|---|---|
| | Succinic semialdehyde | | Malate semialdehyde | |
| Enzyme | Vmax [μmol/(min mg)] | Km [mM] | Vmax [μmol/(min mg)] | Km [mM] |
| St-Mcr | 1.7 | 1.15 | 0.1 | 0.25 |
| Pg-SucD | 4 | nd | 0.007 | nd |

Example 3: Demonstration of DHB Dehydrogenase Activity

To identify a suitable 2,4 DHB dehydrogenase, beta-hydroxyacid dehydrogenases from different biological sources were tested for their ability to reduce malate semi-aldehyde. Among the tested enzymes were the methylbutyraldehyde reductase from *Saccharomyces cerevisiae*, Ypr1 (Ford & Ellis, 2002) (SEQ ID No.14), the 4-hydroxybutyrate dehydrogenase, 4hbdh, of *P. gingivalis* (SEQ ID No.187), the alcohol dehydrogenase, YqhD, of *E; coli* (SEQ ID no. 185), and the succinic semialdehyde reductase, Ms-Ssr, from *Metallosphaera sedula* (Kockelkorn & Fuchs, 2009) (SEQ ID No. 16). The genes YPR1, 4hbdh, yqhD, and Ms-SSR were amplified using primers listed in Table 5 and cloned into vector pET28 (restriction enzymes see Table 5) yielding plasmids pET28-Sce-YPR1, pET28-Pgi-4-hbdh, pET28-Eco-yqhd and pET28-Mse-SSR, respectively. The proteins were expressed and purified as described in Example 1.

TABLE 5

Primers and restriction enzymes used to clone candidate beta-hydroxyacid dehydrogenases

| Enzyme | Accession No | Primer 5'-3' | Restriction enzymes |
|---|---|---|---|
| YPR1 | GI: 6320576 | TATAATGCTAGCATGCCTGC TACGTTAAAGAA (SEQ ID No. 18) | NheI |
| | | TATAATGAGCTCTCATTGGA AAATTGGGAAGG (SEQ ID No. 18) | SacI |
| YqhD | GI: 16130909 | TATAATGAATTCTTAGCGGG CGG CTTCGTATATACGGCGGCTG ACA (SEQ ID No. 20) | EcoRI |
| | | TATCGTGCTAGCATGAACAA CTTTAATCTGCACA (SEQ ID No. 21) | NheI |
| 4hbdh | GI: 188994588 | TATAATGGATCCTTAGTAGA GTCTTCTGTAG (SEQ ID No. 22) | BamHI |
| | | TATAATCATATGCAACTTTT CAAACTC (SEQ ID No. 23) | NdeI |
| Ms-SSR | GI: 146304190 | TATAATGCTAGCATGAAAGC TGCAGTACTTCA (SEQ ID No. 24) | NheI |
| | | TATAATGAATTCTTACGGGA TTATGAGACTTC (SEQ ID No. 25) | EcoRI |

Test for Malate Semialdehyde Reductase Activity:

Reaction scheme: (L)-Malate semialdehyde+NAD(P)H→(L)-2,4-dihydroxybutyric acid+NAD(P)

The assay mixture contained 200 mM Hepes (pH 7.5), 50 mM KCl, 5 mM $MgCl_2$, 0.24 mM NADH or NADPH, and appropriate amounts of purified enzyme or cell extract. Reactions were started by adding 10 mM (L)-malate semialdehyde (malate semialdehyde was prepared freshly for each test, see Example 3). Enzymatic assays were carried out at 30° C. in 96-well flat bottomed microtiter plates in a final volume of 250 μL. The reactions were followed by the characteristic absorption of NAD(P)H at 340 nm ($\epsilon_{NADPH}$=6.22 $mM^{-1}$ $cm^{-1}$) in a microplate reader (BioRad 680XR). Results are listed in Table 6.

TABLE 6

Reducing activity of selected beta-hydroxyacid dehydrogenases on malate semialdehyde (Results represent the average of at least two independent experiments).

| Enzyme | Origin | Reported function | Activity on malate semialdehyde (cofactor NADH) [μmol/(min * mg_prot)] | Activity on malate semialdehyde (cofactor NADPH) [μmol/(min * mg_prot)] |
|---|---|---|---|---|
| Ms-SSR (SEQ ID No. 16) | *M. sedula* | Succinic semialdehyde reductase | 4.9 | 4.9 |
| YqhD (SEQ ID No 185) | *E. coli* | Alcohol dehydrogenase | nd | 1.2 |
| 4hbdh (SEQ ID No 187) | *P. gingivalis* | 4-hydroxy-butyrate dehydrogenase | 33 | nd |
| YPR1 (SEQ ID No. 14) | *S. cerevisiae* | Methyl-butyraldehyde reductase | nd | 0.19 |

The succinic semialdehyde dehydrogenase from *M. sedula* and the methylbutyraldehyde reductase from *S. cerevisiae* have malate semialdehyde reductase activity. The Km of Ms-SSR for malate semialdehyde was 4 mM.

Example 4: Rational Construction of an Improved Malyl-CoA Reductase Enzyme

Site-directed mutagenesis was carried out using the oligonucleotide pairs listed in Table 7 and the pET28-Sto-mcr plasmid as the template. Point mutations to change the amino acid sequences were introduced by PCR (Phusion 1U, HF buffer 20% (v/v), dNTPs 2.5 mM, direct and reverse primers 1 µM each, template plasmid 200 ng, water). When possible, plasmids created by PCR contained new restriction sites (introduced using silent mutations) in addition to the functional mutation to facilitate identification of mutated clones. The PCR products were digested by DpnI at 37° C. for 2×2 h to remove template DNA, and transformed into NEB DH5-α competent *E. coli* cells (NEB). The mutated plasmids were identified by restriction site analysis and verified to carry the desired mutations by DNA sequencing.

TABLE 7

Primer pairs used to mutate the mcr gene of *S. tokodaii*.

| Mutation | Primer 5'-3' |
|---|---|
| Tyr206 | Forward<br>CATTCTGCCTTTAGGGGACGGCNNKGACGCCAAAACG<br>(SEQ ID No. 26)<br><br>Revers<br>CGTTTTGGCGTCMNNGCCGTCCCCTAAAGGCAGAATG<br>(SEQ ID No. 27) |

Figure 3:
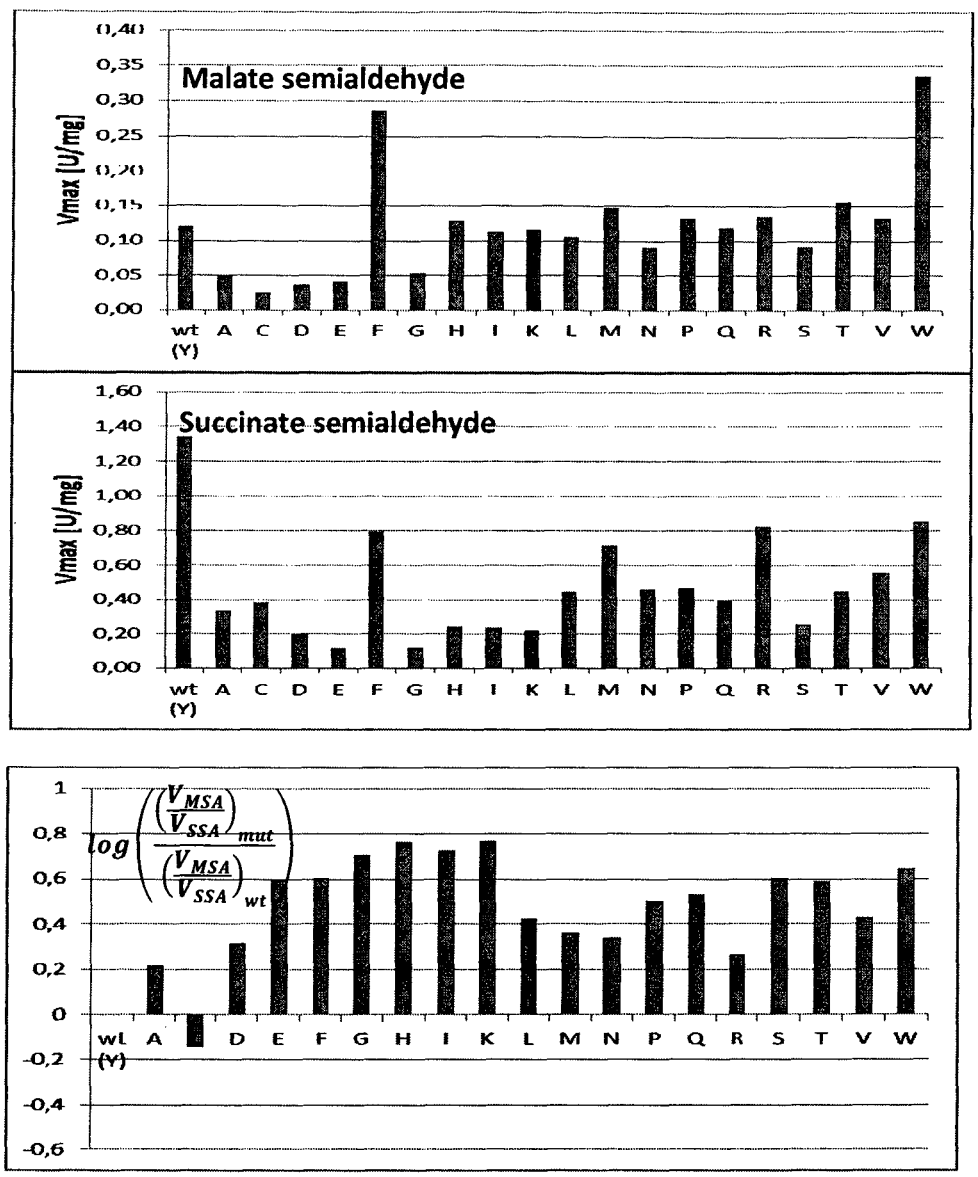
FIG. 3: Chromatograms showing the presence of 2,4-DHB after incubation of 2 mM acetyl-CoA, 2 mM glyoxylate, and 2 mM NADPH, with different combinations of DHB pathway enzymes (Reaction 1: malyl-CoA lyase (150 µg/mL Me-Mcl), malyl-CoA reductase (100 µg/mL St-Mcr), and malate semialdehyde reductase (100 µg/mL Ms-SSAred H39R N43H); Reaction 2:same as reaction 1 but using 100 µg/mL Pg-SucD as malyl-CoA reductase; Control 1: same as reaction 1 but without malyl-CoA reductase; Control 2: same as reaction 1 but without malate semialdehyde reductase.)

The impact of the genetic modifications of St-Mcr was tested in the oxidative sense of the reaction using Assay 3 described in Example 2. FIG. 3 shows that replacing the natural Tyr206 by other amino acids decreases the activity on the natural substrate, succinic semialdehyde, causing at the same time an increased or at least constant activity on malate semialdehyde. Thus, replacing Tyr206 by appropriate amino acid residues provides a selective advantage regarding the specificity of Mcr for the DHB pathway intermediate.

Preferred amino acid residues in position 206 are therefore phenylalanine, histidine, isoleucine, lysine, methionine, glycine, asparagine, proline, arginine, glutamine, leucine, serine, tryptophane, and threonine.

The protein wherein the Tyrosine 206 is replaced by a Proline residue is represented by SEQ ID No. 202.

Example 5: Rational Construction of an Improved DHB Dehydrogenase

Site-directed mutagenesis was carried out using the oligonucleotide pairs listed in Table 6 and the pET28-Mse-SSR plasmid as the template. Point mutations to change the amino acid sequences were introduced by PCR (Phusion 1U, HF buffer 20% (v/v), dNTPs 2.5 mM, direct and reverse primers 1 µM each, template plasmid 200 ng, water). When possible, plasmids created by PCR contained new restriction sites (introduced using silent mutations) in addition to the functional mutation to facilitate identification of mutated clones. The PCR products were digested by DpnI at 37° C. for 2×2 h to remove template DNA, and transformed into NEB DH5-α competent *E. coli* cells (NEB). The mutated plasmids were identified by restriction site analysis and verified to carry the desired mutations by DNA sequencing. Table 8 summarizes kinetic parameters of the mutants. The results demonstrate that the double mutant Ms-SSR H39R N43H (SEQ ID No.38) has improved affinity for malate semialdehyde when compared to the wild type enzyme.

TABLE 8

Primer pairs used to mutate *M. sedula* succinic semialdehyde reductase (Ms-SSR)

| Mutation | Primer 5'-3' | Restriction enzymes |
|---|---|---|
| H39R | gtcaaggcaaccggtctctgtcg<br>ctccgacgtcaatg (SEQ ID No. 28)<br>cattgacgtcggagcgacagaga<br>ccggttgccttgac (SEQ ID No. 29) | NheI |
| N43H | ggctctgtcactccgacgtacat<br>gtctttgaggggaaaac (SEQ ID No. 30)<br>gttttcccctcaaagacatgtac<br>gtcggagtgacagagcc (SEQ ID No. 31) | NheI |

TABLE 9

Summary of kinetic parameters of *M. sedula* succinic semialdehyde reductase (Ms-SSR) mutants (Results represent the average of at least two independent experiments).

| Mutant | Maximum activity [µmol/(min * $mg_{prot}$)] | Km [mmol/L] |
|---|---|---|
| Wild type (SEQ ID No. 16) | 4.9 | 4 |
| H39R (SEQ ID No. 32) | 1.7 | 1 |
| N43H (SEQ ID No. 34) | 4.3 | 5 |
| H39R N43H (SEQ ID No. 36) | 4.7 | 1 |

The corresponding nucleic sequences are represented by SEQ ID No. 17, SEQ ID No. 33, SEQ ID No. 35 and SEQ ID No. 37.

The coding sequence of *M. sedula* succinic semialdehyde reductase including the mutations H39R and N43H was optimized for maximum expression in *E. coli*, using the GeneOptimizer® software. The synthetic gene was produced by GeneArt® Gene Synthesis (Invitrogen Life Technologie). NheI and EcoRI restriction sites were introduced upstream of the start codon and downstream of the stop codon, respectively, allowing direct cloning into pET28a+ (Novagen).

The resulting pET28-Mse-DHB-Dh-H39R_N43H-opt plasmid was isolated and shown by DNA sequencing to contain the full-length *M. sedula* SSR H39R N43H gene having the correct sequence (SEQ ID No.38).

Example 6: Demonstration of In Vitro Production of DHB by the Synthetic Malyl-CoA Pathway The enzymes malyl-CoA lyase (Me-Mcl), malyl-CoA reductase (St-Mcr or Pg-SucD), and DHB dehydrogenase (Ms-SSA-red $H_{39}N$ N43H) were expressed and purified as described in Examples 1, 2, and 3.

Production of DHB by the pathway comprising malyl-CoA lyase, malyl-CoA reductase, and DHB dehydrogenase was demonstrated in vitro by adding 2 mM glyoxylate to a reaction mixture that contained 50 mM Hepes (pH 7.5), 2 mM acetyl-CoA, 2 mM NADPH, 100 µg/mL DHB dehydrogenase, 150 µg/mL malyl-CoA lyase, and 100 µg/mL malyl-CoA reductase (which was either St-Mcr (reaction 1), or Pg-SucD (reaction 2)).
Control reactions contained all components but were lacking either DHB dehydrogenase (Control 1) or malyl-CoA reductase (Control 2). After 120 min of incubation at 37° C. the DHB content in the reaction mixture was analysed by gas chromatography [GCMS-QP2010 Ultra Shimadzu;

equipped with a FID detector (FID-2010 Plus Shimadzu); autosampler AOC20s (Shimadzu); splitless injector AOC20i (Shimadzu) (230° C.); column: Zebron ZB-FFAP, 30 m×0.25 mm, $d_f$ 0.25 µm; and liner: Tapered focus Liner5× 95×3.4 mm (SGE). Carrier gas was hydrogen at a total flow rate of 25 mL/min. Flame ionization was carried out using an air-hydrogen mixture (flow rates were 300 mL/min and 30 mL/min, respectively). Detector temperature was 240° C. Injected sample volume was 1 µL. Temperature program is provided in Table 10.

Figure 2:
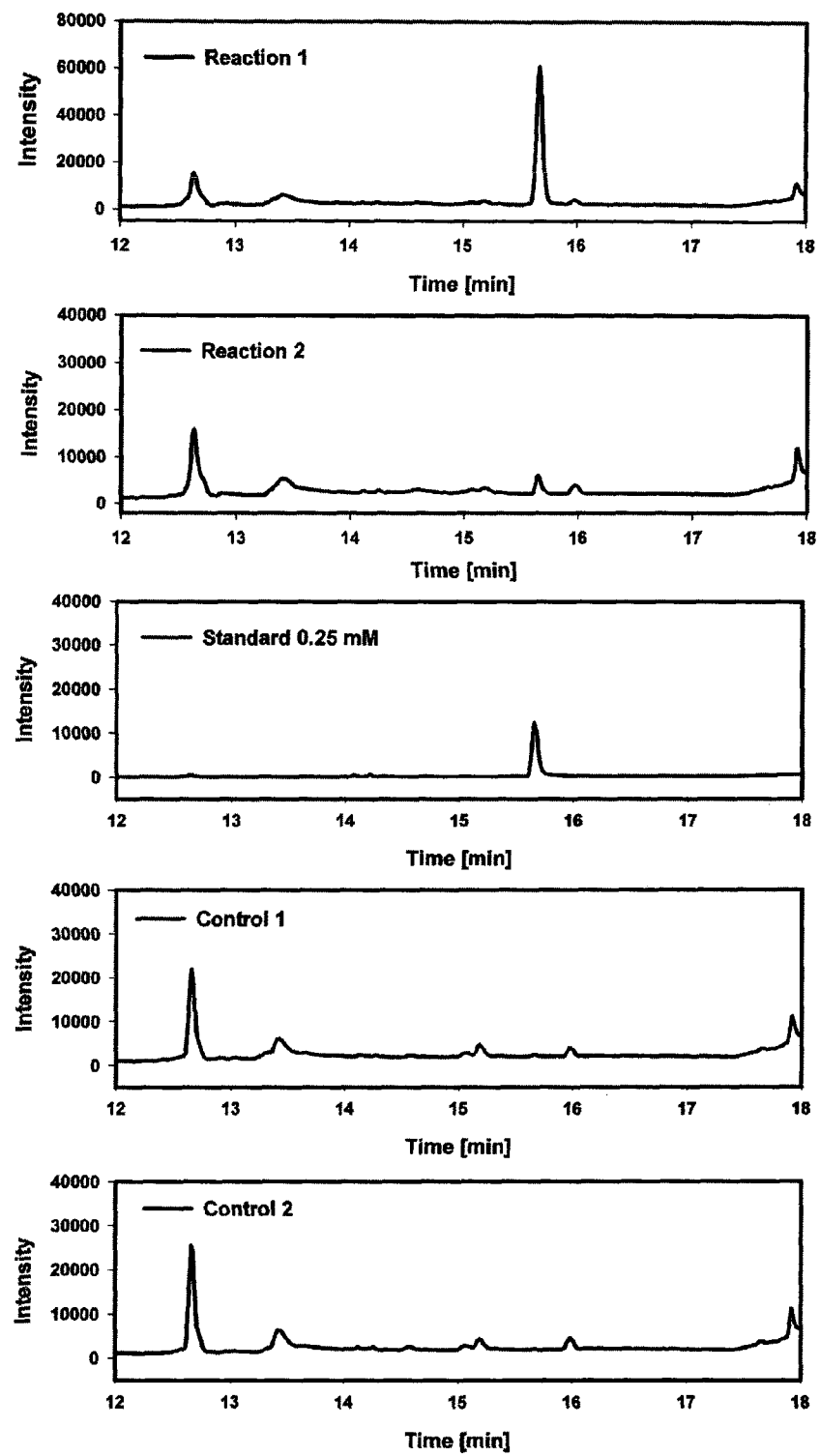
FIG. 2: Figure shows (top graph) activity on malate semialdehyde, (middle graph) activity on succinic semialdehyde, (lower graph) changes of enzyme specificity compared to the wild-type enzyme expressed as the logarithm of the ratio of mutant activity on malate semialdehyde and succinic semialdehyde over the ratio of wild type activity on malate semialdehyde and succinic semialdehyde. (positive values indicate changes of specificity in favour of malate semialdehyde).

Chromatograms showing presence of DHB in the reactions containing all pathway enzymes and absence of DHB in samples containing only two out of three pathway enzymes are shown in FIG. 2.

TABLE 10

Temperature program for GC analysis of reaction mixtures

| Column temperature [° C.] | Hold [min] | Gradient [° C./min] | Runtime [min] |
|---|---|---|---|
| 90 | 0 | 0 | 0 |
| 115 | 1.8 | 30 | 2.63 |
| 170 | 1 | 4 | 17.38 |
| 230 | 3 | 50 | 21.58 |

Example 7: Construction of Optimized DHB Producer Strains

Construction of a Plasmid for Simultaneous Expression of Malyl-CoA Synthetase, Malyl-CoA Reductase, and DHB-Dehydrogenase:

The coding sequence of the malyl-CoA lyase from *M. extorquens*, Me-mcl, was amplified from plasmid pET28-Mex-mcl using the high fidelity polymerase Phusion (Fermentas) and the forward and reverse primers 5'-TCACACA-GGAAACAGAATTC GAGCTCGGTAATGTCGTTTACCCTGATTCAG CAAGCGACT-3' (SEQ ID No. 39) and 5'-GGTATATCTC-CTTCTTAAAGTTAAACTTATTTGCCGCCCATTG-CATCCGCTT TCTG-3' (SEQ ID No. 40) which contained restriction sites for SacI upstream of the start codon (underlined). The coding sequence of the malonyl-CoA reductase from *S. tokodaii*, St-mcr, was amplified from plasmid pET28-Sto-mcr using the forward and reverse primers 5'-GTTTAACTTTAAGAAGGAGATATACCATGATTCT-GATGCGCCGTACCCTGA AAGCG-3' (SEQ ID No. 41) and 5'-GGTATATCTCCTTCTTAAAGTTAAACTTACT-TCTCGATGTAGCCTTTCTCCA CGAG-3' (SEQ ID No. 42) which contained restriction sites for BamHI downstream of the stop codon. The plasmid pET28-Mse-DHB-Dh-H39R_N43H-opt (Example 5) was used as the template to amplify the optimized coding sequence of the succinic semialdehyde reductase H39R N43H from *M. sedula* using the forward and reverse primers 5'-GTTTAACTT-TAAGAAGGAGATATACCATGAAAGCAGCAGTTCTG-CATACCT ATAAAGAACCGCTGAGCAT-3' (SEQ ID No. 43) and 5'-ATGCCTGCAGGTCGACTCTAGA GGATCCTTACGGAATAATCAGGCTACGA ATT-GCTTC-3' (SEQ ID No. 44) that introduced a BamHI restriction site downstream of the stop codon (underlined).

The forward primers for St-mcr and the succinic semialdehyde reductase H39R N43H from *M. sedula* contained a rbs motif. The three genes were simultaneously cloned into the pACT3 expression vector by homologous recombination using the In-Fusion cloning kit (Clontech).

The resulting and pACT3-MCL-DHB (SEQ ID No. 45) plasmid was isolated and shown by DNA sequencing to have the correct sequence.

Construction of a Plasmid for Simultaneous Expression of Malyl-CoA Synthetase, Malyl-CoA Reductase, and DHB-Dehydrogenase:

The DNA sequences coding for the two protein subunits of malyl-CoA synthetase, mtkA (YP_00296285) and mtkB (YP_002962852), from *Methylobacterium extorquens* AM1 were optimized for the expression in *Escherichia coli* using the GENEius software (Eurofins). The optimized DNA sequences of the subunit were physically linked by the DNA sequence naturally occurring between the mtkA and mtkB genes in *M. Extorquens* genome (CGAACGGGGGAG-GAATCACGCC, SEQ ID No. 46). The resulting DNA fragment, 'mtkA gene-linker DNA-mtkB gene', was synthesized by Eurofins MWG OPERON® and subcloned into pET28b expression vector using NheI and EcoRI restriction enzymes. The resulting DNA plasmid pET28-Mex-mtkAB (SEQ ID No. 47) was used to simultaneously amplify the two codons optimized genes encoding malyl-CoA synthetase from *M. extorquens*, Me-mtkA and Me-mtkB using the high fidelity polymerase Phusion (Fermentas) and the forward and reverse primers 5'-CAGGAAACAGAATTC GAGCTCGGTAATGGATGTGCACGAATATCAGGCGA AAGAACTGCT-3' (SEQ ID No. 48) and 5'-TACGGCG-CATCAGAATCATtacgccgcacgtgctaacacatcggcaac-3' (SEQ ID No. 49) which contained restriction sites for SacI upstream of the start codon (underlined). The coding sequence of the malonyl-CoA reductase from *S. tokodaii*, St-mcr, was amplified from plasmid pET28-Sto-mcr using the forward and reverse primers 5'-GGCGTAATGATTCT-GATGCGCCGTACCCTGAAAGCG-3' (SEQ ID No. 50) and 5'-CTGCTGCTTTCATTACTTCTCGATGTAGC-CTTTCTCCACGAG-3' (SEQ ID No. 51) which contained restriction sites for BamHI downstream of the stop codon. The plasmid pET28-Mse-DHB-Dh-H39R_N43H-opt (Example 5) was used as the template to amplify the optimized coding sequence of the succinic semialdehyde reductase H39R N43H from *M. sedula* using the forward and reverse primers 5'-TACATCGAGAAGTAATGAAAGCAGCAGT-TCTGCATACCTATAAAGAAC-3' (SEQ ID No. 52) and 5'-CCTGCAGGTCGACTCTAGAGGATCCTTACG-GAATAATCAGGCTACGAATT GCTTCAC-3' (SEQ ID No. 53) that introduced a BamHI restriction site downstream of the stop codon (underlined).

The three genes were simultaneously cloned into the pEXT20 expression vector by homologous recombination using the In-Fusion cloning kit (Clontech).

The resulting pEXT20-MCS-DHB (SEQ ID No.54) plasmid was isolated and shown by DNA sequencing to have the correct sequence.

Construction of Plasmids for Overexpression of Phosphoenolpyruvate (PEP) Carboxykinase, PEP Carboxylase, Pyruvate Kinase, Pyruvate Carboxylase, Isocitrate Lyase Enzymes and the Galactose Symporter Permease:

The plasmid pACT3-pck harbouring the PEP carboxykinase encoding pck gene of *E. coli* was constructed by amplifying the pck coding sequence using genomic DNA from E. coli MG1655 as the template and the forward and reverse primers, respectively, 5'TATAATCCCGGGAT-GCGCGTTAACAATGGTTTGACC3' (SEQ ID No. 56 and 5'TATAATTCTAGATTACAGTTTCGGACCAGCCG3' (SEQ ID No. 57). The DNA fragment was digested with XmaI and XbaI, ligated into the corresponding sites of the pACT3 expression vector (Dykxhoorn et al., 1996) using T4 DNA ligase (Biolabs), and transformed into E. coli DH5α cells. The transformants were selected on solid LB medium containing chloramphenicol (25 μg/mL). The resulting plasmid was isolated and correct insertion of the pck gene was verified by sequencing. Plasmids pACT3-aceA, pACT3-ppc, pACT3-galP, pACT3-pck and pACT3-pyc harbouring, respectively, aceA, ppc, galP, or pykA (all E. coli) or pck from Lactococcus lactis were constructed analogously using the primers listed in Table 11.

TABLE 11

Primers used for construction of plasmids for gene overexpression.

| Gene | Primer | Linker | Sequence |
|---|---|---|---|
| Ec_pck | Ec_pck_clon_for | XmaI | tataatcccgggatgcgcgttaacaatggtttgacc (SEQ ID No. 57) |
| | Ec_pck_clon_rev | XbaI | tataattctagattacagtttcggaccagccg (SEQ ID No. 58) |
| Ec_ppc | Ec_ppc_clon_for | XmaI | tataatcccgggatgaacgaacaatattcc (SEQ ID No. 59) |
| | Ec_ppc_clon_rev | XbaI | tataattctagattagccggtatacgcat (SEQ ID No. 60) |
| Ec_pykA | Ec_pykA_clon_for | XmaI | tataatcccgggatgtccagaaggcttcgcagaaca (SEQ ID No. 61) |
| | Ec_pykA_clon_rev | XbaI | tataattctagattactctaccgttaaaatac (SEQ ID No. 62) |
| Ec_aceA | Ec_aceA_clon_for | XmaI | tataatcccgggatgaaaacccgtacacaacaaatt (SEQ ID No. 63) |
| | Ec_aceA_clon_rev | XbaI | tataattctagattagaactgcgattcttcag (SEQ ID No. 64) |
| Ll_pycA | Ll_pycA_clon_for | XmaI | tataatcccgggatgaaaaaactactcgtcgccaat (SEQ ID No. 65) |
| | Ll_pycA_clon_rev | XbaI | tataattctagattaattaatttcgattaaca (SEQ ID No. 66) |
| Ec_galP | Ec_galP_clon_for | XmaI | tataatcccgggatgcctgacgctaaaaaacaggggcggt (SEQ ID No. 67) |
| | Ec_galP_clon_rev | XbaI | tataattctagattaatcgtgagcgcctatttc (SEQ ID No. 68) |

Restriction sites used for cloning into pACT3 are underlined

It is understood that removal of the lacI gene from the backbone of the above described plasmids along with the genomic deletion of lacI in the host strain may render protein expression from above described plasmids constitutive.

Construction of Strains with Optimized Carbon Flux Repartitioning for DHB Production Several genes were disrupted in E. coli strain MG1655 in order to optimise carbon flux repartitioning and cofactor supply for DHB production. Gene deletions were carried out using either the lambda red recombinase method according to Datsenko et al. (Datsenko & Wanner, 2000), or the phage transduction method adapted from Miller (Miller, 1992).

Protocol for introduction of gene deletions using the lambda red recombinase method: the deletion cassettes were prepared by PCR using high fidelity polymerase Phusion™ (Finnzymes), and the FRT-flanked kanamycin resistance gene (kan) of plasmid pKD4 as the template (Datsenko & Wanner, 2000). Sense primers contained sequences corresponding to the 5'-end of each targeted gene (underlined) followed by 20 bp corresponding to the FRT-kan-FRT cassette of pKD4. Anti-sense primers contained sequences corresponding to the 3'-end region of each targeted gene (underlined) followed by 20 bp corresponding to the cassette. The primers are described in Table 12. PCR products were digested with DpnI and purified prior to transformation.

E. coli MG1655 strain was rendered electro-competent by growing the cells to an $OD_{600}$ of 0.6 in LB liquid medium at 37° C., concentrating the cells 100-fold, and washing them twice with ice-cold 10% glycerol. The cells were transformed with plasmid pKD46 (Datsenko & Wanner, 2000) by electroporation (2.5 kV, 200 Ω, 25 μF, in 2 mm gap cuvettes). Transformants were selected at 30° C. on ampicillin (100 μg/mL) LB solid medium.

Disruption cassettes were transformed into electro-competent E. coli strains harbouring the lambda Red recombinase-expressing plasmid pKD46. The cells were grown at 30° C. in liquid SOB medium containing ampicillin (100 μg/mL). The lambda red recombinase system was induced by adding 10 mM arabinose when $OD_{600}$ of the cultures reached 0.1. Cells were further grown to an $OD_{600}$ of 0.6 before they were harvested by centrifugation, washed twice with ice-cold 10% glycerol, and transformed with the disruption cassette by electroporation. After an overnight phenotypic expression at 30° C. in LB liquid medium, cells were plated on solid LB medium containing 25 μg/mL kanamycin. Transformants were selected after cultivation at 30° C.

The gene replacement was verified by colony PCR using Crimson Taq polymerase (NEB). A first reaction was carried out with the flanking locus-specific primers (see Table 12) to verify simultaneous loss of the parental fragment and gain of the new mutant specific fragment. Two additional reactions were done by using one locus-specific primer together with one of the corresponding primers k1rev, or k2for (see Table 12) that align within the FRT-kanamycin resistance cassette (sense locus primer/k1rev and k2for/reverse locus primer).

The resistance gene (FRT-kan-FRT) was subsequently excised from the chromosome using the FLP recombinase-harbouring plasmid pCP20 (Cherepanov & Wackernagel, 1995) leaving a scar region containing one FRT site. pCP20 is an ampicillin and CmR plasmid that shows temperature-sensitive replication and thermal induction of FLP recombinase synthesis. Kanamycin resistant mutants were transformed with pCP20, and ampicillin-resistant transformants were selected at 30° C. Transformants were then grown on solid LB medium at 37° C. and tested for loss of all antibiotic resistances. Excision of the FRT-kanamycin cassette was analysed by colony PCR using crimson Taq polymerase and the flanking locus-specific primers (Table 12). Multiple deletions were obtained by repeating the above described steps.

TABLE 12

Primers used for gene disruptions.

| Gene | Primer | Sequence |
|---|---|---|
| ldhA | Δ_ldhA_for | gaaggttgcgcctacacactaagcatagttgttgatgagtgtaggctggagctgcttc (SEQ ID No. 69) |
|  | Δ_ldhA_rev | ttaaaccagttcgttcgggcaggtttcgccttttttcatgggaattagccatggtcc SEQ ID No. 70) |
| adhE | Δ_adhE_for | atggctgttactaatgtcgctgaacttaacgcactcgtagagcgtgtgtaggctggagctgcttc (SEQ ID No. 71) |
|  | Δ_adhE_rev | ttaagcggattttttcgcttttttctcagctttagccggagcagccatatgaatatcctccttag (SEQ ID No. 72) |
| ackA | Δ_ackA_for | atgtcgagtaagttagtactggttctgaactgcggtagttcttcagtgtaggctggagctgcttc (SEQ ID No. 73) |
|  | Δ_ackA_rev | tcaggcagtcaggcggctcgcgtcttgcgcgataaccagttcttccatatgaatatcctccttag (SEQ ID No. 74) |
| focA-pflB | Δ_focA-pflB_for | ttactccgtatttgcataaaaaccatgcgagttacgggcctataagtgtaggctggagctgcttc (SEQ ID No. 75) |
|  | Δ_focA-pflB_rev | atagattgagtgaaggtacgagtaataacgtcctgctgctgttctcatatgaatatcctccttag (SEQ ID No. 76) |
| pta | Δ_pta_for | gtgtcccgtattattatgctgatccctaccggaaccagcgtcggtgtgtaggctggagctgcttc (SEQ ID No. 77) |
|  | Δ_pta_rev | ttactgctgctgtgcagactgaatcgcagtcagcgcgatggtgtacatatgaatatcctccttag (SEQ ID No. 78) |
| poxB | Δ_poxB_for | atgaaacaaacggttgcagcttatatcgccaaaacactcgaatcggtgtaggctggagctgcttc (SEQ ID No. 79) |
|  | Δ_poxB_rev | ttaccttagccagtttgttttcgccagttcgatcacttcatcacccatatgaatatcctccttag (SEQ ID No. 80) |
| sad | Δ_sad_for | atgaccattactccggcaactcatgcaatttcgataaatcctgccgtgtaggctggagctgcttc (SEQ ID No. 81) |
|  | Δ_sad_rev | tcagatccggtctttccacaccgtctggatattacagaattcgtgcatatgaatatcctccttag (SEQ ID No. 82) |
| gabD | Δ_gabD_for | atgaaacttaacgacagtaacttattccgccagcaggcgttgattgtgtaggctggagctgcttc (SEQ ID No. 83) |
|  | Δ_gabD_rev | ttaaagaccgatgcacatatatttgatttctaagtaatcttcgatcatatgaatatcctccttag (SEQ ID No. 847) |
| gadA | Δ_gadA_for | atggaccagaagctgttaacggatttccgctcagaactactcgatgtgtaggctggagctgcttc (SEQ ID No. 85) |
|  | Δ_gadA_rev | tcaggtgtgtttaaagctgttctgctgggcaatacccctgcagtttcatatgaatatcctccttag (SEQ ID No. 86) |
| gadB | Δ_gadB_for | atggataagaagcaagtaacggatttaaggtcggaactactcgatgtgtaggctggagctgcttc (SEQ ID No. 87) |
|  | Δ_gadB_rev | tcaggtatgtttaaagctgttctgttgggcaatacccctgcagtttcatatgaatatcctccttag (SEQ ID No. 88) |
| gadC | Δ_gadC_for | atggctacatcagtacagacaggtaaagctaagcagctcacattagtgtaggctggagctgcttc (SEQ ID No. 89) |
|  | Δ_gadC_rev | ttagtgttcttgtcattcatcacaatatagtgtggtgaacgtgccatatgaatatcctccttag (SEQ ID No. 90) |
| sfcA | Δ_sfcA_for | atggaaccaaaaacaaaaaaacagcgttcgctttatatcccttacgtgtaggctggagctgcttc (SEQ ID No. 91) |
|  | Δ_sfcA_rev | ttagatggaggtacggcggtagtcgcggtattcggcttgccagaacatatgaatatcctccttag (SEQ ID No. 92) |
| maeB | Δ_maeB_for | atggatgaccagttaaaacaaagtgcacttgatttccatgaatttgtgtaggctggagctgcttc (SEQ ID No. 93) |
|  | Δ_maeB_rev | ttacagcggttgggtttgcgcttctaccacggccagcgccaccatcatatgaatatcctccttag (SEQ ID No. 94) |
| ppc | Δ_ppc_for | atgaacgaacaatattccgcattgcgtagtaatgtcagtatgctcgtgtaggctggagctgcttc (SEQ ID No. 95) |
|  | Δ_ppc_rev | ttagccggtattacgcatacctgccgcaatcccggcaatagtgaccatatgaatatcctccttag (SEQ ID No. 96) |
| pykA | Δ_pykA_for | atgtccagaaggcttcgcagaacaaaaatcgttaccacgttaggcgtgtaggctggagctgcttc (SEQ ID No. 97) |
|  | Δ_pykA_rev | ttactctaccgttaaaatacgcgtggtattagtagaacccacggtcatatgaatatcctccttag (SEQ ID No. 98) |

TABLE 12-continued

Primers used for gene disruptions.

| Gene | Primer | Sequence |
|------|--------|----------|
| pykF | Δ_pykF_for | <u>atgaaaaagaccaaaattgtttgcaccatcggaccgaaaaccgaag</u>tgtaggctggagctgcttc (SEQ ID No. 99) |
|      | Δ_pykF_rev | <u>ttacaggacgtgaacagatgcggtgttagtagtgccgctcggtac</u>catatgaatatcctccttag (SEQ ID No. 100) |
| mgsA | Δ_mgsA_for | <u>atggaactgacgactcgcactttacctgcgcggaaacatattgcg</u>gtgtaggctggagctgcttc (SEQ ID No. 101) |
|      | Δ_mgsA_rev | <u>ttacttcagacggtccgcgagataacgctgataatcggggatcag</u>catatgaatatcctccttag (SEQ ID No. 102) |
| icIR | Δ_icIR_for | <u>atggtcgcacccattcccgcgaaacgcggcagaaaaccgccgtt</u>tgtgtaggctggagctgcttc (SEQ ID No. 103) |
|      | Δ_icIR_rev | <u>tcagcgcattccaccgtacgccagcgtcacttccttcgccgcttt</u>catatgaatatcctccttag (SEQ ID No. 104) |
| icd  | Δ_icd_for | <u>atggaaagtaaagtagttgttccggcacaaggcaagaagatcacc</u>gtgtaggctggagctgcttc (SEQ ID No. 105) |
|      | Δ_icd_rev | <u>ttacatgttttcgatgatcgcgtcaccaaactctgaacatttcag</u>catatgaatatcctccttag (SEQ ID No. 106) |
| sucA | Δ_sucA_for | <u>atgcagaacagcgctttgaaagcctggttggactcttcttacctc</u>gtgtaggctggagctgcttc (SEQ ID No. 107) |
|      | Δ_sucA_rev | <u>ttattcgacgttcagcgcgtcattaaccagatcttgttgctgttt</u>catatgaatatcctccttag (SEQ ID No. 108) |
| sucB | Δ_sucB_for | <u>atgagtagcgtagatattctggtccctgacctgcctgaatccgta</u>gtgtaggctggagctgcttc (SEQ ID No. 109) |
|      | Δ_sucB_rev | <u>ctacacgtccagcagcagacgcgtcggatcttccagcaactcttt</u>catatgaatatcctccttag (SEQ ID No. 110) |
| frdA | Δ_frdA_for | <u>gtgcaaacctttcaagccgatcttgccattgtaggcgccggtggc</u>gtgtaggctggagctgcttc (SEQ ID No. 111) |
|      | Δ_frdA_rev | <u>tcagccattcgcccttctcclicttattggctgcttccgccttatc</u>catatgaatatcctccttag (SEQ ID No. 112) |
| frdB | Δ_frdB_for | <u>atggctgagatgaaaaacctgaaaattgaggtggtgcgctataac</u>gtgtaggctggagctgcttc (SEQ ID No. 113) |
|      | Δ_frdB_rev | <u>ttagcgtggtttcagggtcgcgataagaaagtctttcgaactttc</u>catatgaatatcctccttag (SEQ ID No. 114) |
| frdC | Δ_frdC_for | <u>atgacgactaaacgtaaaccgtatgtacggccaatgacgtccacc</u>gtgtaggctggagctgcttc (SEQ ID No. 115) |
|      | Δ_frdC_rev | <u>ttaccagtacagggcaacaaacaggattacgatggtggcaaccac</u>catatgaatatcctccttag (SEQ ID No. 116) |
| frdD | Δ_frdD_for | <u>atgattaatccaaatccaaagcgttctgacgaaccggtattctgg</u>gtgtaggctggagctgcttc (SEQ ID No. 117) |
|      | Δ_frdD_rev | <u>ttagattgtaacgacaccaatcagcgtgacaactgtcaggatagc</u>catatgaatatcctccttag (SEQ ID No. 118) |
| ptsI | Δ_ptsI_for | <u>atgatttcaggcattttagcatccccgggtatcgctttcggtaaa</u>gtgtaggctggagctgcttc (SEQ ID No. 119) |
|      | Δ_ptsI_rev | <u>ttagcagattgttttttcttcaatgaacttgttaaccagcgtcat</u>catatgaatatcctccttag (SEQ ID No. 120) |
| ptsG | Δ_ptsG_for | <u>atgtttaagaatgcatttgctaacctgcaaaaggtcggtaaatcg</u>gtgtaggctggagctgcttc (SEQ ID No. 121) |
|      | Δ_ptsG_rev | <u>ttagtggttacggatgtactcatccatctcggttttcaggttatc</u>catatgaatatcctccttag (SEQ ID No. 122) |
| lacI | Δ_lacI_for | <u>gtgaaaccagtaacgttatacgatgtcgcagagtatgccggtgtcg</u>gtgtaggctggagctgcttc (SEQ ID No. 123) |
|      | Δ_lacI_rev | <u>tcactgcccgctttccagtcgggaaacctgtcgtgccagctgcat</u>catatgaatatcctccttag (SEQ ID No. 124) |
| lldD | Δ_lldD_for | <u>atgattatttccgcagccagcgattatcgcgccgcagcgcaacgc</u>gtgtaggctggagctgcttc (SEQ ID No. 125) |
|      | Δ_lldD_rev | <u>ctatgccgcattcccttcgccatgggagccagtgccgcaggcaa</u>catatgaatatcctccttag (SEQ ID No. 126) |
| pgi  | Δ_pgi_for | <u>atgaaaaacatcaatccaacgcagaccgctgcctggcaggcacta</u>gtgtaggctggagctgcttc (SEQ ID No. 127) |
|      | Δ_pgi_rev | <u>ttaaccgcgccacgctttatagcggttaatcagaccattggtcga</u>catatgaatatcctccttag (SEQ ID No. 128) |

Sequences homologous to target genes are underlined

TABLE 13

Primer pairs used for verification of gene disruptions

| Deleted gene | Forward primer | Reverse Primer |
|---|---|---|
| K2 for/ k1 rev | cggtgccctga atgaactgc (SEQ ID No. 129) | cagtcatagcc gaatagcct (SEQ ID No. 130) |
| ldhA | atacgtgtccc gagcggtag (SEQ ID No. 131) | tacacatcccg ccatcagca (SEQ ID No. 132) |
| adhE | gaagtaaacgg gaaaatcaa (SEQ ID No. 133) | agaagtggcata agaaaacg (SEQ ID No. 134) |
| ackA | ccattggctga aaattacgc (SEQ ID No. 135) | gttccattgca cggatcacg (SEQ ID No. 136) |
| focA_ pflB | atgccgtagaa gccgccagt (SEQ ID No. 137) | tgttggtgcgca gctcgaag (SEQ ID No. 138) |
| pta | gcaaatctggt ttcatcaac (SEQ ID No. 139) | tcccttgcacaa aacaaagt (SEQ ID No. 140) |
| poxB | ggatttggtt ctcgcataat (SEQ ID No. 141) | agcattaacgg tagggtcgt (SEQ ID No. 142) |
| sad | gctgattctcg cgaataaac (SEQ ID No. 143) | aaaaacgttct tgcgcgtct (SEQ ID No. 144) |
| gabD | tctgtttgtca ccaccccgc (SEQ ID No. 145) | aagccagcacc tggaagcag (SEQ ID No. 146) |
| gadA | aagagctgccg caggaggat (SEQ ID No. 147) | gccgccctctt aagtcaaat (SEQ ID No. 148) |
| gadB | ggattttagca atattcgct (SEQ ID No. 149) | cctaatagcag gaagaagac (SEQ ID No. 150) |
| gadC | gctgaactgt tgctggaaga (SEQ ID No. 151) | ggcgtgctttt acaactaca (SEQ ID No. 152) |
| sfcA | tagtaaataa cccaaccggc (SEQ ID No. 153) | tcagtgagcgc agtgtttta (SEQ ID No. 154) |
| maeB | attaatggtga gagtttgga (SEQ ID No. 155) | tgctttttttt attattcgc (SEQ ID No. 156) |
| ppc | gctttataaa agacgacgaa (SEQ ID No. 157) | gtaacgacaat tccttaagg (SEQ ID No. 158) |
| pykA | tttatatgcc atggtttct (SEQ ID No. 159) | atctgttagag gcggatgat (SEQ ID No. 160) |
| pykF | ctggaacgtt aaatctttga (SEQ ID No. 161) | ccagtttagt agctttcatt (SEQ ID No. 162) |
| iclR | gatttgttcaacat taactcatcgg (SEQ ID No. 163) | tgcgattaac agacacccctt (SEQ ID No. 164) |
| mgsA | tctcaggtgct cacagaaca (SEQ ID No. 165) | tatggaagagg cgctactgc (SEQ ID No. 166) |
| icd | cgacctgctgc ataaacacc (SEQ ID No. 167) | tgaacgctaag gtgattgca (SEQ ID No. 168) |
| sucA | acgtagacaa gagctcgcaa (SEQ ID No. 169) | catcacgtacg actgcgtcg (SEQ ID No. 170) |
| sucB | tgcaactttg tgctgagcaa (SEQ ID No. 171) | tatcgcttccg ggcattgtc (SEQ ID No. 172) |
| frdA | aaatcgatctcgt caaatttcagac (SEQ ID No. 173) | aggaaccacaa atcgccata (SEQ ID No. 174) |
| frdB | gacgtgaaga ttactacgct (SEQ ID No. 175) | agttcaatgc tgaaccacac (SEQ ID No. 176) |
| frdC | tagccgcgaccac ggtaagaaggag (SEQ ID No. 177) | cagcgcatcac ccggaaaca SEQ ID No. 178) |
| frdD | atcgtgatca ttaacctgat (SEQ ID No. 179) | ttaccctgat aaattaccgc (SEQ ID No. 180) |
| lacI | gaatctggtg tatatggcga (SEQ ID No. 181) | tcttcgctat tacgccagct (SEQ ID No. 182) |
| lldD | cgtcagcgga tgtatctggt (SEQ ID No. 183) | gcggaatttct ggttcgtaa (SEQ ID No. 184) |
| pgi | ttgtcaacga tggggtcatg (SEQ ID No. 195) | aaaaatgccg acataacgtc (SEQ ID No. 196) |
| ptsG | ccatccgttga atgagtttt (SEQ ID No. 197) | tggtgttaact ggcaaaatc (SEQ ID No. 198) |
| ptsI | gtgacttccaa cggcaaaag (SEQ ID No. 199) | ccgttggtttg atagcaata (SEQ ID No. 200) |

Protocol for introduction of gene deletions using the phage transduction method: strains carrying the desired single deletions were obtained from the Keio collection (Baba et al., 2006). Phage lysates of single deletion mutants were prepared by inoculating 10 mL of LB medium containing 50 μg/mL kanamycin, 2 g/L glucose, and 5 mM CaCl$_2$ with 100 μL of overnight precultures. Following an incubation of 1 h at 37° C., 200 μL of phage lysate prepared from the wild-type MG1655 strain were added, and cultures were incubated for another 2-3 h until cell lysis had completed. After addition of 200 μL chloroform, cell preparations were first vigorously vortexed and then centrifuged for 10 min at 4500×g. The clear lysate was recovered and stored at 4° C.

The receptor strain was prepared for phage transduction by an overnight cultivation at 37° C. in LB medium. A volume of 1.5 mL of the preculture was centrifuged at 1500×g for 10 min. The supernatant was discarded and the cell pellet was resuspended in 600 µL of a solution containing 10 mM MgSO$_4$ and 5 mM CaCl$_2$. The transduction was carried out by mixing 100 µL of the solution containing the receptor strain with 100 µL of lysate and incubating this mixture at 30° C. for 30 min. Thereafter, 100 µL of a 1M sodium citrate solution were added followed by vigorous vortexing. After addition of 1 mL LB medium, the cell suspension was incubated at 37° C. for 1 h before spreading the cells on LB agar dishes containing 50 µg/mL kanamycin. Clones able to grow in presence of the antibiotic were confirmed by colony PCR to contain the desired deletion using the primers listed in Table 13. After the introduction of each gene deletion, the antibiotic marker was removed as described above following the method of (Cherepanov & Wackernagel, 1995)

The plasmids co-expressing malyl-CoA synthetase, malyl-CoA reductase, and DHB dehydrogenase (pEXT20-MCS-DHB or pACT3-MCS-DHB); or plasmids co-expressing malyl-CoA lyase, malyl-CoA reductase, and DHB dehydrogenase (pEXT20-MCL-DHB or pACT3-MCL-DHB); or the empty control plasmids (pEXT20 or pACT3) were transformed alone or together with one of the plasmids pACT3-aceA, pACT3-ppc, pACT3-galP, pACT3-pck or pACT3-pyc into the optimized host strains. Transformants containing both a plasmid expressing the DHB-pathway enzymes, and a plasmid expressing an anaplerotic enzyme were selected on solid LB medium containing chloramphenicol (25 µg/mL) and kanamycin (50 µg/mL). Non-exclusive examples of constructed strains are listed in Table 14.

TABLE 14

Examples of strains constructed for DHB production

| Strain | Relevant Genotype |
|---|---|
| MG1655 | Wild-type |
| ECE50 | pEXT20-MCS-DHB |
| ECE51 | pACT3-MCS-DHB |
| ECE52 | pEXT20-MCL-DHB |
| ECE53 | pACT3-MCL-DHB |
| ECE54 | ΔldhA ΔadhE Δpta-ack ΔpflB pEXT20-MCS-DHB |
| ECE55 | ΔldhA ΔadhE Δpta-ack ΔpflB pACT3-MCS-DHB |
| ECE56 | ΔldhA ΔadhE Δpta-ack ΔpflB pACT3-MCS-DHB, pACT3-ppc |
| ECE57 | ΔldhA ΔadhE Δpta-ack ΔpflB ΔpoxB pEXT20-MCS-DHB |
| ECE58 | ΔldhA ΔadhE Δpta-ack ΔpflB ΔpoxB pACT3-MCS-DHB |
| ECE59 | ΔldhA ΔadhE Δpta-ack ΔpflB ΔpoxB pEXT20-MCS-DHB, pACT3-ppc |
| ECE60 | ΔldhA ΔadhE Δpta-ack ΔpflB ΔpoxB ΔmaeB ΔsfcA pEXT20-MCS-DHB |
| ECE61 | ΔldhA ΔadhE Δpta-ack ΔpflB ΔpoxB ΔmaeB ΔsfcA pACT3-MCS-DHB |
| ECE62 | ΔldhA ΔadhE Δpta-ack ΔpflB ΔpoxB ΔmaeB ΔsfcA pEXT20-MCS-DHB, pACT3-ppc |
| ECE63 | ΔldhA ΔadhE Δpta-ack ΔpflB ΔpoxB ΔmaeB ΔsfcA Δpts pEXT20-MCS-DHB |
| ECE64 | ΔldhA ΔadhE Δpta-ack ΔpflB ΔpoxB ΔmaeB ΔsfcA Δpts pACT3-MCS-DHB |
| ECE65 | ΔldhA ΔadhE Δpta-ack ΔpflB ΔpoxB ΔmaeB ΔsfcA Δpts pEXT20-MCS-DHB, pACT3-ppc |
| ECE66 | ΔldhA ΔadhE Δpta-ack ΔpflB ΔpoxB ΔmaeB ΔsfcA Δpts ΔfrdBC pEXT20-MCS-DHB |
| ECE67 | ΔldhA ΔadhE Δpta-ack ΔpflB ΔpoxB ΔmaeB ΔsfcA Δpts ΔfrdBC pACT3-MCS-DHB |
| ECE68 | ΔldhA ΔadhE Δpta-ack ΔpflB ΔpoxB ΔmaeB ΔsfcA Δpts ΔfrdBC pEXT20-MCS-DHB, pACT3-ppc |
| ECE69 | Δpta ΔiclR ΔaceB pACT3-MCL-DHB |
| ECE70 | Δpta ΔiclR ΔaceB |
| ECE71 | Δpta ΔiclR ΔaceB ΔadhE pACT3-MCL-DHB |
| ECE72 | Δpta ΔiclR ΔaceB ΔadhE |
| ECE73 | ΔldhA ΔadhE Δpta-ack ΔpoxB ΔmaeB ΔsfcA Δmdh Δmqo ΔiclR ΔaceB pEXT20-MCS-DHB, pACT3-MCL-DHB |
| ECE74 | ΔldhA ΔadhE Δpta-ack ΔpoxB ΔmaeB ΔsfcA Δmdh Δmqo ΔiclR ΔaceB Δpts pEXT20-MCS-DHB, pACT3-MCL-DHB |
| ECE75 | ΔldhA ΔadhE Δpta-ack ΔpoxB ΔmaeB ΔsfcA Δmdh Δmqo ΔiclR ΔaceB Δpts Δpgi pEXT20-MCS-DHB, pACT3-MCL-DHB |
| ECE76 | ΔldhA ΔadhE Δpta-ack ΔpoxB ΔmaeB ΔsfcA Δmdh Δmqo ΔiclR ΔaceB Δpgi pEXT20-MCS-DHB, pACT3 MCL-DHB |
| ECE77 | ΔldhA ΔadhE Δpta-ack ΔpoxB ΔmaeB ΔsfcA Δmdh Δmqo ΔiclR ΔaceB ΔghrAB pEXT20-MCS-DHB, pACT3-MCL-DHB |
| ECE79 | ΔldhA ΔadhE Δpta-ack ΔpflB ΔpoxB ΔmaeB ΔsfcA aspC pEXT20-MCS-DHB, pACT3-ppc |
| ECE80 | ΔldhA ΔadhE Δpta-ack ΔpflB ΔpoxB ΔmaeB ΔsfcA ΔaspC ΔiclR ΔaceB pEXT20-MCS-DHB, pACT3-ppc |
| ECE81 | ΔldhA ΔadhE Δpta-ack ΔpflB ΔpoxB ΔmaeB ΔsfcA ΔaspC ΔiclR ΔaceB ΔghrAB pEXT20-MCS-DHB, pACT3-ppc |

Example 8: Demonstration of Zymotic Production of DHB by the Synthetic Malyl-CoA Pathway Strains and Cultivation Conditions:

Experiments were carried out using strain ECE69 which expressed the DHB pathway from plasmid pACT3-MCL-DHB represented by SEQ ID No. 203 (the wild-type Mcr enzyme was replaced by the Mcr Tyr206Pro mutant in this experiment) and the isogenic control strain ECE70 containing the empty plasmid pACT3. All cultivations were carried out at 37° C. on an Infors rotary shaker running at 170 rpm. Overnight cultures (3 mL medium in test tube) were inoculated from glycerol stocks and used to adjust an initial OD$_{600}$ of 0.05 in 100 mL growth cultures cultivated in 500 mL shake flasks. IPTG was added at a concentration of 1 mmol/L when OD$_{600}$ of the growth cultures reached 1. The composition of the growth mineral medium is provided in Example 2.

Estimation of DHB Concentration by LC-MS/MS Analyses:

DHB was quantified using LC-MS: Liquid anion exchange chromatography was performed on an ICS-3000 system from Dionex (Sunnyvale, USA) equipped with an automatic eluent (KOH) generator system (RFIC, Dionex), and an autosampler (AS50, Dionex) holding the samples at 4° C. Analytes were separated on an IonPac AS11 HC (250×2 mm, Dionex) column protected by an AG11 HC (50×2 mm, Dionex) pre-column. Column temperature was held at 25° C., flow rate was fixed at 0.25 mL/min, and analytes were eluted applying the KOH gradient described earlier (Groussac E, Ortiz M & Francois J (2000) Improved protocols for quantitative determination of metabolites from biological samples using high performance ionic-exchange chromatography with conductimetric and pulsed amperometric detection. *Enzyme. Microb. Technol.* 26, 715-723). Injected sample volume was 15 µL. For background reduction, an ASRS ultra II (2 mm, external water mode, 75 mA) anion suppressor was used. Analytes were quantified a mass-sensitive detector (MSQ Plus, Thermo) running in ESI mode (split was ⅓, nitrogen pressure was 90 psi, capillary voltage was 3.5 kV, probe temperature was 450° C.).

Results:

After 24 h of cultivation the supernatant of strains ECE69 and ECE70 contained 0.05 mM DHB and 0 mM DHB, respectively, demonstrating DHB production via the synthetic pathway.

REFERENCES

Akita, O., Nishimori, C., Shimamoto, T., Fujii, T. & Iefuji, H. (2000). Transport of pyruvate in *Saccharomyces cerevisiae* and cloning of the gene encoded pyruvate permease. *Biosci Biotechnol Biochem* 64, 980-984.

Alber, B., Olinger, M., Rieder, A., Kockelkorn, D., Jobst, B., Hügler, M. & Fuchs, G. (2006). Malonyl-coenzyme A reductase in the modified 3-hydroxypropionate cycle for autotrophic carbon fixation in archaeal *Metallosphaera* and *Sulfolobus* spp. *J Bacteriol* 188, 8551-8559.

Arps, P. J., Fulton, G. F., Minnich, E. C. & Lidstrom, M. E. (1993). Genetics of serine pathway enzymes in *Methylobacterium extorquens* AM1: phosphoenolpyruvate carboxylase and malyl coenzyme A lyase. *J Bacteriol* 175, 3776-3783.

Auriol, C., Bestel-Corre, G., Claude, J.-B., Soucaille, P. & Meynial-Salles, I. (2011). Stress-induced evolution of *Escherichia coli* points to original concepts in respiratory cofactor selectivity. *Proc Natl Acad Sci USA* 108, 1278-1283.

Baba, T., Ara, T., Hasegawa, M., Takai, Y., Okumura, Y., Baba, M., Datsenko, K. A., Tomita, M., Wanner, B. L. & Mori, H. (2006). Construction of *Escherichia coli* K-12 in-frame, single-gene knockout mutants: the Keio collection. *Mol Syst Biol* 2, 2006.0008.

Bailey, J. E. (1991). Toward a science of metabolic engineering. *Science* 252, 1668-1675.

Camarasa, C., Bidard, F., Bony, M., Barre, P. & Dequin, S. (2001). Characterization of *Schizosaccharomyces pombe* malate permease by expression in *Saccharomyces cerevisiae*. *Appl Environ Microbiol* 67, 4144-4151.

Cherepanov, P. P. & Wackernagel, W. (1995). Gene disruption in *Escherichia coli*: TcR and KmR cassettes with the option of Flp-catalyzed excision of the antibiotic-resistance determinant. *Gene* 158, 9-14.

Chistoserdova, L., Kalyuzhnaya, M. G. & Lidstrom, M. E. (2009). The expanding world of methylotrophic metabolism. *Annu Rev Microbiol* 63, 477-499.

Datsenko, K. A. & Wanner, B. L. (2000). One-step inactivation of chromosomal genes in *Escherichia coli* K-12 using PCR products. *Proc Natl Acad Sci USA* 97, 6640-6645.

Ford, G. & Ellis, E. M. (2002). Characterization of Ypr1p from *Saccharomyces cerevisiae* as a 2-methylbutyraldehyde reductase. *Yeast Chichester Engl* 19, 1087-1096.

Friedmann, S., Steindorf, A., Alber, B. E. & Fuchs, G. (2006). Properties of succinyl-coenzyme A:L-malate coenzyme A transferase and its role in the autotrophic 3-hydroxypropionate cycle of *Chloroflexus aurantiacus*. *J Bacteriol* 188, 2646-2655.

Grobler, J., Bauer, F., Subden, R. E. & Van Vuuren, H. J. (1995). The mae1 gene of *Schizosaccharomyces pombe* encodes a permease for malate and other C4 dicarboxylic acids. *Yeast Chichester Engl* 11, 1485-1491.

Groeneveld, M., Weme, R. G. J. D. O., Duurkens, R. H. & Slotboom, D. J. (2010). Biochemical characterization of the C4-dicarboxylate transporter DctA from *Bacillus subtilis*. *J Bacteriol* 192, 2900-2907.

Jantama, K., Zhang, X., Moore, J. C., Shanmugam, K. T., Svoronos, S. A. & Ingram, L. O. (2008a). Eliminating side products and increasing succinate yields in engineered strains of *Escherichia coli* C. *Biotechnol Bioeng* 101, 881-893.

Jantama, K. Haupt, M. J., Svoronos, S. A., Zhang, X., Moore, J. C., Shanmugam, K. T. & Ingram, L. O. (2008b). Combining metabolic engineering and metabolic evolution to develop nonrecombinant strains of *Escherichia coli* C that produce succinate and malate. *Biotechnol Bioeng* 99, 1140-1153.

Kawasaki, T., Koita, H., Nakatsubo, T., Hasegawa, K., Wakabayashi, K., Takahashi, H., Umemura, K., Umezawa, T. & Shimamoto, K. (2006). Cinnamoyl-CoA reductase, a key enzyme in lignin biosynthesis, is an effector of small GTPase Rac in defense signaling in rice. *Proc Natl Acad Sci USA* 103, 230-235.

Kockelkorn, D. & Fuchs, G. (2009). Malonic semialdehyde reductase, succinic semialdehyde reductase, and succinyl-coenzyme A reductase from *Metallosphaera sedula*: enzymes of the autotrophic 3-hydroxypropionate/4-hydroxybutyrate cycle in *Sulfolobales*. *J Bacteriol* 191, 6352-6362.

Larkin, M. A., Blackshields, G., Brown, N. P., Chema, R., McGettigan, P. A., McWilliam, H., Valentin, F., Wallace, I. M., Wilm, A. & other authors. (2007). Clustal W and Clustal X version 2.0. *Bioinforma Oxf Engl* 23, 2947-2948.

Lin, H., Bennett, G. N. & San, K.-Y. (2005). Metabolic engineering of aerobic succinate production systems in *Escherichia coli* to improve process productivity and achieve the maximum theoretical succinate yield. *Metab Eng* 7, 116-127.

Meister, M., Saum, S., Alber, B. E. & Fuchs, G. (2005). L-malyl-coenzyme A/beta-methylmalyl-coenzyme A lyase is involved in acetate assimilation of the isocitrate lyase-negative bacterium *Rhodobacter capsulatus*. *J Bacteriol* 187, 1415-1425.

Millard, C. S., Chao, Y. P., Liao, J. C. & Donnelly, M. I. (1996). Enhanced production of succinic acid by overexpression of phosphoenolpyruvate carboxylase in *Escherichia coli*. *Appl Environ Microbiol* 62, 1808-1810.

Miller, J. H. (1992). *A Short Course in Bacterial Genetics: A Laboratory Manual and Handbook for Escherichica coli and Related Bacteria*. Plainview (NY): Cold Spring Harbor Laboratory Press.

Rognstad, R. & Katz, J. (1979). Effects of 2,4-dihydroxybutyrate on lipogenesis in rat hepatocytes. *J Biol Chem* 254, 11969-11972.

Sambrook, J., Fritsch, E. F. & Maniatis, T. (1989). *Molecular Cloning: A Laboratory Manual,* 2nd edn. Cold Spring Harbor: Cold Spring Harbor Laboratory Press.

Sanchez, A. M., Bennett, G. N. & San, K.-Y. (2005). Novel pathway engineering design of the anaerobic central metabolic pathway in *Escherichia coli* to increase succinate yield and productivity. *Metab Eng* 7, 229-239.

Sauer, U. & Eikmanns, B. J. (2005). The PEP-pyruvate-oxaloacetate node as the switch point for carbon flux distribution in bacteria. *Fems Microbiol Rev* 29, 765-794.

Seedorf, H., Fricke, W. F., Veith, B., Brüggemann, H., Liesegang, H., Strittmatter, A., Miethke, M., Buckel, W., Hinderberger, J. & other authors. (2008). The genome of *Clostridium kluyveri*, a strict anaerobe with unique metabolic features. *Proc Natl Acad Sci USA* 105, 2128-2133.

Shinka, T., Inoue, Y., Ohse, M., Ito, A., Ohfu, M., Hirose, S. & Kuhara, T. (2002). Rapid and sensitive detection of urinary 4-hydroxybutyric acid and its related compounds by gas chromatography-mass spectrometry in a patient with succinic semialdehyde dehydrogenase deficiency. *J Chromatogr B Anal Technol Biomed Life Sci* 776, 57-63.

Smejkalová, H., Erb, T. J. & Fuchs, G. (2010). Methanol assimilation in *Methylobacterium extorquens* AM 1: demonstration of all enzymes and their regulation. *Plos One* 5.

Söhling, B. & Gottschalk, G. (1993). Purification and characterization of a coenzyme-A-dependent succinate-semialdehyde dehydrogenase from *Clostridium kluyveri*. *Eur J Biochem Febs* 212, 121-127.

Vuilleumier, S., Chistoserdova, L., Lee, M.-C., Bringel, F., Lajus, A., Zhou, Y., Gourion, B., Barbe, V., Chang, J. & other authors. (2009). *Methylobacterium* genome sequences: a reference blueprint to investigate microbial metabolism of C1 compounds from natural and industrial sources. *Plos One* 4, e5584.

Wang, Q., Ou, M. S., Kim, Y., Ingram, L. O. & Shanmugam, K. T. (2010). Metabolic flux control at the pyruvate node in an anaerobic *Escherichia coli* strain with an active pyruvate dehydrogenase. *Appl Environ Microbiol* 76, 2107-2114.

Werpy, T. & Petersen, G. (2004). *Top value added chemicals from biomass. Results of screening for potential candidates from sugars and synthesis gas.* Washington D.C.

Zarzycki, J., Brecht, V., Müller, M. & Fuchs, G. (2009). Identifying the missing steps of the autotrophic 3-hydroxypropionate CO2 fixation cycle in *Chloroflexus aurantiacus*. *Proc Natl Acad Sci USA* 106, 21317-21322.

Zelle, R. M., de Hulster, E., van Winden, W. A., de Waard, P., Dijkema, C., Winkler, A. A., Geertman, J.-M. A., van Dijken, J. P., Pronk, J. T. & van Maris, A. J. A. (2008). Malic acid production by *Saccharomyces cerevisiae*: engineering of pyruvate carboxylation, oxaloacetate reduction, and malate export. *Appl Environ Microbiol* 74, 2766-2777.

Zelle, R. M., de Hulster, E., Kloezen, W., Pronk, J. T. & van Maris, A. J. A. (2010). Key process conditions for production of C(4) dicarboxylic acids in bioreactor batch cultures of an engineered *Saccharomyces cerevisiae* strain. *Appl Environ Microbiol* 76, 744-750.

Zhang, X., Jantama, K., Shanmugam, K. T. & Ingram, L. O. (2009). Reengineering *Escherichia coli* for Succinate Production in Mineral Salts Medium. *Appl Environ Microbiol* 75, 7807-7813.

Zhang, X., Wang, X., Shanmugam, K. T. & Ingram, L. O. (2011). L-malate production by metabolically engineered *Escherichia coli*. *Appl Environ Microbiol* 77, 427-434.

---

The invention claimed is:

1. A method for the preparation of 2,4-dihydroxybutyric acid (2,4-DHB), comprising the successive steps of:
   a) a first step of converting malate, succinyl-CoA, and/or glyoxylate into malyl-CoA by contacting the malate, the succinyl-CoA, and/or the glyoxylate with a malyl-CoA synthetase, succinyl-CoA: (L)-malate-CoA transferase, and/or malyl-CoA lyase,
   b) a second step of converting malyl-CoA previously obtained into malate-4-semialdehyde by contacting the malyl-CoA with a malyl-CoA reductase, and
   c) a third step of converting malate-4-semialdehyde into 2,4-DHB by contacting the malate-4-semialdehyde with a DHB dehydrogenase.

2. The method of claim 1, wherein the malyl-CoA lyase has the amino acid sequence set forth in SEQ ID NO: 1 or any variant or fragment thereof having malyl-CoA lyase activity and the succinyl-CoA: (L)-malate-CoA transferase has the amino acid sequence set forth in at least one of SEQ ID NO: 191 and SEQ ID NO: 193 or any variant or fragment thereof having succinyl-CoA: (L)-malate-CoA transferase activity.

3. The method of claim 1, wherein the malyl-CoA lyase is encoded by the nucleic acid sequence set forth in SEQ ID NO: 2 or any variant or fragment thereof which results in a functionally active malyl-CoA lyase, and the succinyl-CoA: (L)-malate-CoA transferase is encoded by at least one of the nucleic acid sequences set forth in SEQ ID NO: 194 and SEQ ID NO: 192 or any variant or fragment thereof, which results in a functionally active succinyl-CoA: (L)-malate-CoA transferase.

4. The method according to claim 1, wherein the malyl-CoA reductase is selected from the group consisting of: a malonyl-CoA reductase, a succinyl-CoA reductase,3-hydroxy-3-methylglutaryl-CoA (HMG-CoA) reductase, cinnamoyl-CoA reductase, acetaldehyde dehydrogenase, and any variant thereof having malonyl-CoA reductase activity, succinyl-CoA reductase activity, HMG-CoA reductase activity, cinnamoyl-CoA reductase activity, or acetaldehyde dehydrogenase activity.

5. The method of claim 1, wherein the malyl-CoA reductase has the amino acid sequence set forth in SEQ ID NO: 7, SEQ ID NO: 10, or SEQ ID NO: 189, or any variant or fragment thereof having malyl-CoA reductase activity.

6. The method of claim 5, wherein the malyl-CoA reductase is encoded by any one of the nucleic acid sequences set forth in SEQ ID NO: 8, SEQ ID NO: 11, or SEQ ID NO: 190, or any variant or fragment thereof, which results in a functionally active malyl-CoA reductase.

7. The method of claim 1, wherein:
the malyl-CoA reductase comprises the amino acid sequence of SEQ ID NO: 7 with at least one mutation in at least one of the positions P111, L152, T154, L202, G203, D204, Y206, D207, K209, T210, T238, T239, D295, and R318,
the amino acid in said positions is replaced by any one of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine, and
the mutated malyl-CoA reductase has malyl-CoA reductase activity.

8. The method of claim 7, wherein the malyl-CoA reductase comprises the amino acid sequence set forth in SEQ ID NO: 202 or is encoded by the nucleic acid sequence set forth in SEQ ID NO: 201.

9. The method of claim 1, wherein the DHB dehydrogenase is a methylbutyraldehyde reductase, a succinic semialdehyde reductase, a 4-hydroxybutyrate dehydrogenase, or an alcohol dehydrogenase.

10. The method of claim 9, wherein the DHB dehydrogenase comprises the amino acid sequence of SEQ ID NO: 14, SEQ ID NO: 16, SEQ ID NO: 32, SEQ ID NO: 34, SEQ ID NO: 36, SEQ ID NO: 187, or SEQ ID NO: 185, or any variant thereof having DHB dehydrogenase activity.

11. The method of claim 10, wherein the DHB dehydrogenase is encoded by any one of the nucleic acid sequences set forth in SEQ ID NO: 15, SEQ ID NO: 17, SEQ ID NO: 33, SEQ ID NO: 35, SEQ ID NO: 37, SEQ ID NO: 188, SEQ ID NO: 186, or any variant or fragment thereof, which results in a functionally active DHB dehydrogenase.

12. The method according to claim 1, wherein, steps a), b) and c) are performed by a modified microorganism heterologously expressing at least one of malyl-CoA synthetase, succinyl-CoA: (L)-malate-CoA transferase, malyl-CoA lyase, malyl-CoA reductase, and DHB dehydrogenase.

13. The method according to claim 1, wherein steps a), b) and c) are performed within the same microorganism.

* * * * *

SEQUENCE LISTING

```
<160> NUMBER OF SEQ ID NOS: 203

<210> SEQ ID NO 1
<211> LENGTH: 324
<212> TYPE: PRT
<213> ORGANISM: Methylobacter extorquens

<400> SEQUENCE: 1

Met Ser Phe Thr Leu Ile Gln Gln Ala Thr Pro Arg Leu His Arg Ser
1               5                   10                  15

Glu Leu Ala Val Pro Gly Ser Asn Pro Thr Phe Met Glu Lys Ser Ala
            20                  25                  30

Ala Ser Lys Ala Asp Val Ile Phe Leu Asp Leu Glu Asp Ala Val Ala
        35                  40                  45

Pro Asp Asp Lys Glu Gln Ala Arg Lys Asn Ile Ile Gln Ala Leu Asn
    50                  55                  60

Asp Leu Asp Trp Gly Asn Lys Thr Met Met Ile Arg Ile Asn Gly Leu
65                  70                  75                  80

Asp Thr His Tyr Met Tyr Arg Asp Val Val Asp Ile Val Glu Ala Cys
                85                  90                  95

Pro Arg Leu Asp Met Ile Leu Ile Pro Lys Val Gly Val Pro Ala Asp
            100                 105                 110

Val Tyr Ala Ile Asp Val Leu Thr Thr Gln Ile Glu Gln Ala Lys Lys
        115                 120                 125

Arg Glu Lys Lys Ile Gly Phe Glu Val Leu Ile Glu Thr Ala Leu Gly
    130                 135                 140

Met Ala Asn Val Glu Ala Ile Ala Thr Ser Ser Lys Arg Leu Glu Ala
145                 150                 155                 160

Met Ser Phe Gly Val Ala Asp Tyr Ala Ala Ser Thr Arg Ala Arg Ser
                165                 170                 175

Thr Val Ile Gly Gly Val Asn Ala Asp Tyr Ser Val Leu Thr Asp Lys
            180                 185                 190

Asp Glu Ala Gly Asn Arg Gln Thr His Trp Gln Asp Pro Trp Leu Phe
        195                 200                 205
```

```
Ala Gln Asn Arg Met Leu Val Ala Cys Arg Ala Tyr Gly Leu Arg Pro
    210                 215                 220

Ile Asp Gly Pro Phe Gly Asp Phe Ser Asp Pro Asp Gly Tyr Thr Ser
225                 230                 235                 240

Ala Ala Arg Arg Cys Ala Ala Leu Gly Phe Glu Gly Lys Trp Ala Ile
                245                 250                 255

His Pro Ser Gln Ile Asp Leu Ala Asn Glu Val Phe Thr Pro Ser Glu
            260                 265                 270

Ala Glu Val Thr Lys Ala Arg Arg Ile Leu Glu Ala Met Glu Glu Ala
        275                 280                 285

Ala Lys Ala Gly Arg Gly Ala Val Ser Leu Asp Gly Arg Leu Ile Asp
    290                 295                 300

Ile Ala Ser Ile Arg Met Ala Glu Ala Leu Ile Gln Lys Ala Asp Ala
305                 310                 315                 320

Met Gly Gly Lys

<210> SEQ ID NO 2
<211> LENGTH: 975
<212> TYPE: DNA
<213> ORGANISM: Methylobacter extorquens

<400> SEQUENCE: 2
atgagcttca ccctgatcca gcaggccacc ccgcgcctgc accgctcgga actcgcggtt     60
cccggctcca acccgacctt catggagaag tcggccgcct cgaaggccga cgtgatcttc    120
ctcgacctcg aggacgcggt tgcgcccgac gacaaggagc aggcccgcaa gaacatcatc    180
caggccctca cgacctggga ttggggcaac aagaccatga tgatccgcat caacggtctc    240
gacacccact acatgtaccg cgacgtggtg gacatcgtgg aggcctgccc cgcgcctcgac    300 atgatcctga tccccaaggt cggcgtgccg gccgacgtct acgccatcga cgtgctgacg    360
acgcagatcg agcaggccaa gaagcgcgag aagaagatcg gcttcgaggt gctgatcgag    420
accgcgctcg gcatggccaa tgtcgaggcg atcgcgacct cgtctaagcg ccttgaggcg    480
atgtccttcg gtgtcgccga ctacgccgct tccacccgcg cccgctccac cgtgatcggc    540
ggcgtcaacg ccgattacag cgtgctcacc gacaaggacg aggccggcaa ccgccagacc    600
cactggcagg atccgtggct gttcgcccag aaccgcatgc tggtcgcctg ccgcgcctac    660
ggcctgcgcc cgatcgacgg tcccttcggc gacttctccg atccggacgg ctacacctcg    720
gccgctcgcc gctgcgccgc gctcggcttc gagggcaagt gggcgatcca ccctcgcag    780 atcgatctcg ccaacgaggt cttcaccccc tccgaggccg aggtcaccaa ggcccgccgc    840
atcctggaag ccatggaaga ggccgccaag gccggccgcg gcgccgtctc gctcgacggc    900
cgtctcatcg acatcgcctc gatccgcatg gccgaggcgc tgatccagaa ggccgacgcg    960
atgggcggaa agtaa                                                    975

<210> SEQ ID NO 3
<211> LENGTH: 975
<212> TYPE: DNA
<213> ORGANISM: Methylobacter extorquens

<400> SEQUENCE: 3
atgtcgttta ccctgattca gcaagcgact ccgcgcttac atcgcagcga acttgcggtt     60
ccgggttcaa atccgacctt tatggagaaa tcagcagcca gcaaggccga tgtcatcttc    120
ttggatctgg aggatgccgt tgcacctgat gacaaagaac aggcgcgtaa gaacatcatt    180
```

```
caggcactga acgatctgga ctggggcaac aaaacgatga tgatccgcat taacggtctg    240
gacacccact acatgtatcg ggatgtggtc gacatcgtag aagcatgccc tcgcctggat    300
atgattctca ttcccaaagt cggagtacca gcagacgtgt atgcgattga tgtgctgacg    360
acgcaaatcg aacaggcgaa gaaacgggag aagaaaatcg gattcgaggt gctcattgaa    420
acggctttag gcatggccaa tgttgaagcc atcgccacat cttcgaaacg cttggaagcg    480
atgtcgtttg gtgtgccga ttatgcagca tccactcgtg cccgtagtac cgtgattggt    540
ggtgtgaatg cggattactc cgttctcact gacaaagatg aagcagggaa ccgtcaaacc    600
cattggcaag atccgtggct gtttgcgcag aatcgcatgc tggttgcttg ccgtgcttac    660
gggcttcgcc cgattgatgg gccatttggc gacttcagcg atcccgatgg ctataccagt    720
gctgcgcgtc gttgtgcggc gctgggcttt gaaggcaaat gggcgattca cccgagtcag    780
atcgacttag cgaacgaggt gttcacaccg tctgaagctg aagtcaccaa agcgcgccgc    840
attctggagg caatggaaga agcggccaaa gccggtcgtg gcgctgtaag cctgacggt    900 cgcttgattg acatcgccag cattcgcatg gctgaagccc tgatccagaa agcggatgca    960
atgggcggca aataa                                                     975

<210> SEQ ID NO 4
<211> LENGTH: 348
<212> TYPE: PRT
<213> ORGANISM: Rhodobacter capsulatus

<400> SEQUENCE: 4

Met Leu Gln Ala Gln Lys Phe Leu Ala Arg Arg Ser Ala Thr Ile Tyr
1               5                   10                  15

Arg Lys Arg Asn Ala Ser Arg Asn Phe Ile Ala Glu Arg Gln Met Ser
            20                  25                  30

Phe Arg Thr Gln Pro Pro Ala Pro Ala Arg Leu Asn Arg Cys Gln Leu
        35                  40                  45

Phe Gly Pro Gly Ser Arg Pro Ala Ile Phe Glu Lys Met Ala Gln Ser
    50                  55                  60

Ala Ala Asp Val Ile Asn Leu Asp Leu Glu Asp Ser Val Ala Pro Asp
65                  70                  75                  80

Asp Lys Pro Gln Ala Arg Arg Asn Ile Ile Glu Ala Ser His Asn Ile
                85                  90                  95

Asp Trp Gly Asn Lys Tyr Leu Ser Val Arg Ile Asn Gly Leu Asp Thr
            100                 105                 110

Pro Phe Trp Tyr Arg Asp Val Val Glu Leu Leu Glu Asp Gly Ser Glu
        115                 120                 125

Arg Ile Asp Gln Ile Met Ile Pro Lys Val Gly Cys Ala Ala Asp Val
    130                 135                 140

Tyr Ala Val Asp Ala Leu Val Thr Ala Ile Glu Ala Ala Lys Gly Arg
145                 150                 155                 160

Lys Lys Arg Ile Ser Leu Glu Val Ile Ile Glu Ser Ala Ala Gly Ile
                165                 170                 175

Ala His Val Glu Glu Ile Ala Ala Ala Ser Pro Arg Leu Gln Ala Met
            180                 185                 190

Ser Leu Gly Ala Ala Asp Phe Ala Ala Ser Met Gly Met Ala Thr Thr
        195                 200                 205

Gly Ile Gly Gly Thr Gln Glu Asn Tyr Tyr Met Leu His Ala Gly Val
    210                 215                 220
```

```
Lys His Trp Ser Asp Pro Trp His Trp Ala Gln Ala Ala Ile Val Ala
225                 230                 235                 240

Ala Cys Arg Thr His Gly Ile Leu Pro Val Asp Gly Pro Phe Gly Asp
            245                 250                 255

Phe Ser Asp Asp Glu Gly Phe Arg Ala Gln Ala Leu Arg Ser Ala Thr
        260                 265                 270

Leu Gly Met Val Gly Lys Trp Ala Ile His Pro Lys Gln Val Ala Leu
    275                 280                 285

Ala Asn Glu Val Phe Thr Pro Ser Asp Ala Ala Val Ala Glu Ala Arg
    290                 295                 300

Glu Ile Leu Ala Ala Met Glu Lys Ala Lys Ala Glu Gly Ala Gly Ala
305                 310                 315                 320

Thr Val Tyr Lys Gly Arg Leu Val Asp Ile Ala Ser Ile Arg Gln Ala
            325                 330                 335

Glu Val Ile Val Arg Gln Ala Glu Met Ala Lys Val
            340                 345

<210> SEQ ID NO 5
<211> LENGTH: 1047
<212> TYPE: DNA
<213> ORGANISM: Rhodobacter capsulatus

<400> SEQUENCE: 5
atgctgcagg cgcagaaatt ccttgcacgc cgcagcgcaa caatatatcg caaacgcaac        60
gcatcccgta acttcattgc gagagacag atgagcttcc gcacccagcc ccctgccccc       120
gcccgcctca accgctgcca gctgttcggg ccgggttcgc gtccggcgat ctttgaaaag       180
atggcgcaat cggcggccga tgtgatcaac ctcgacctgg aagactcggt ggcgcccgac       240
gacaagccgc aggcgcggcg caacatcatc gaggccagcc acaacatcga ctggggcaac       300
aaatatctgt cggtgcggat aacgggctg atacgccgt tctggtatcg gacgtggtc         360 gagctgctgg aagacgggtc cgagcgcatc gaccagatca tgatcccgaa agtgggctgc       420
gccgccgacg tttacgccgt cgatgcgctg gtcaccgcga tcgaggccgc caagggccgg       480
aagaaacgca tctcgctgga agtgatcatc gaatcggccg cgggcatcgc ccatgtcgag       540
gaaatcgcgg ccgcctcgcc gcggctgcag gcgatgagcc ttggcgcggc ggatttcgcg       600
gcctccatgg gcatggccac caccggtatc ggcggcacgc aggaaaacta ctacatgctg       660
catgcgggcg tgaaacattg gtcggacccc tggcactggg cgcaggccgc catcgtcgcc       720
gcctgccgca cccatggcat cctgccggtc gatggcccgt ttggcgattt ctccgatgac       780
gagggcttcc gggcccaggc cttgcggtcg gcgacgctcg gcatggtcgg caaatgggcg       840
atccacccga acaggtcgc tttgcgaac gaggtcttca ccccctctga cgctgcggtt       900
gcagaggcgc gggaaattct ggcggcgatg aaaaggcca aggccgaggg cgccggcgcc       960
accgtctaca aggggcggct ggtcgatatt gcctcgatcc ggcaggcgga agtgattgtc      1020
agacaggcgg aaatggctaa ggtctga                                          1047

<210> SEQ ID NO 6
<211> LENGTH: 1047
<212> TYPE: DNA
<213> ORGANISM: Rhodobacter capsulatus

<400> SEQUENCE: 6
atgcttcagg cgcagaaatt cctggcacgt cgttctgcga cgatttaccg caaacgtaat        60
gcctcccgga acttcattgc gagcgccag atgtcgtttc gtacccaacc accggctcct       120
```

```
gcccgtctga atcgctgcca gctgtttggc ccaggttctc gtcctgcgat cttcgagaaa     180
atggctcaga gtgcagcgga tgtgatcaat ctggatctgg aggacagcgt cgctccggat     240
gataagcccc aagcccgccg caatatcatt gaagcgtcac acaacattga ctggggtaac     300
aagtatctga gcgttcgtat taacggctta gacacgccgt tctggtatcg ggatgtcgtg     360
gagttgctgg aagatggtag cgaacgtatc gaccagatta tgatcccgaa ggtaggttgc     420
gcagcggacg tatatgccgt ggatgcttta gttaccgcga tcgaagccgc taaaggtcgc     480
aagaaacgca tttccctgga agtgatcatc gaaagtgcag ctgggattgc ccatgtggaa     540
gaaatcgccg ctgcctctcc acgcttgcag gcgatgagct taggagcagc ggactttgcc     600
gcgtcgatgg gtatggccac aaccggcatt ggcgggactc aggagaacta ctatatgctg     660
catgcgggcg tgaaacactg gagtgatccc tggcattggg cacaggccgc aattgtggcg     720
gcatgtcgca cgcatgggat tctgccggtt gatggcccgt ttggcgattt ctccgatgac     780
gaaggctttc gtgcacaggc acttcgttcg cgactctggg tatggtggg caaatgggcc     840 attcacccga acaagtggc tctcgcaaac gaggtattta ccccgtcaga tgcggcggtt     900
gcggaagcgc gcgaaatctt ggccgcaatg gagaaagcca aagcggaagg agcgggagct     960
accgtctaca aggtcgcct cgtcgatatc gcgagcattc gccaagcaga agttattgtt    1020
cgccaagcgg aaatggccaa agtctaa                                       1047
```

<210> SEQ ID NO 7
<211> LENGTH: 359
<212> TYPE: PRT
<213> ORGANISM: Sulfolobus tokodaii

<400> SEQUENCE: 7

```
Met Ile Leu Met Arg Arg Thr Leu Lys Ala Ala Ile Leu Gly Ala Thr
1               5                   10                  15

Gly Leu Val Gly Ile Glu Tyr Val Arg Met Leu Ser Asn His Pro Tyr
            20                  25                  30

Ile Lys Pro Ala Tyr Leu Ala Gly Lys Gly Ser Val Gly Lys Pro Tyr
        35                  40                  45

Gly Glu Val Val Arg Trp Gln Thr Val Gly Gln Val Pro Lys Glu Ile
    50                  55                  60

Ala Asp Met Glu Ile Lys Pro Thr Asp Pro Lys Leu Met Asp Asp Val
65                  70                  75                  80

Asp Ile Ile Phe Ser Pro Leu Pro Gln Gly Ala Ala Gly Pro Val Glu
                85                  90                  95

Glu Gln Phe Ala Lys Glu Gly Phe Pro Val Ile Ser Asn Ser Pro Asp
            100                 105                 110

His Arg Phe Asp Pro Asp Val Pro Leu Leu Val Pro Glu Leu Asn Pro
        115                 120                 125

His Thr Ile Ser Leu Ile Asp Glu Gln Arg Lys Arg Arg Glu Trp Lys
    130                 135                 140

Gly Phe Ile Val Thr Thr Pro Leu Cys Thr Ala Gln Gly Ala Ala Ile
145                 150                 155                 160

Pro Leu Gly Ala Ile Phe Lys Asp Tyr Lys Met Asp Gly Ala Phe Ile
                165                 170                 175

Thr Thr Ile Gln Ser Leu Ser Gly Ala Gly Tyr Pro Gly Ile Pro Ser
            180                 185                 190

Leu Asp Val Val Asp Asn Ile Leu Pro Leu Gly Asp Gly Tyr Asp Ala
        195                 200                 205
```

```
Lys Thr Ile Lys Glu Ile Phe Arg Ile Leu Ser Glu Val Lys Arg Asn
    210                 215                 220

Val Asp Glu Pro Lys Leu Glu Asp Val Ser Leu Ala Ala Thr Thr His
225                 230                 235                 240

Arg Ile Ala Thr Ile His Gly His Tyr Glu Val Leu Tyr Val Ser Phe
                245                 250                 255

Lys Glu Glu Thr Ala Ala Glu Lys Val Lys Glu Thr Leu Glu Asn Phe
                260                 265                 270

Arg Gly Glu Pro Gln Asp Leu Lys Leu Pro Thr Ala Pro Ser Lys Pro
            275                 280                 285

Ile Ile Val Met Asn Glu Asp Thr Arg Pro Gln Val Tyr Phe Asp Arg
        290                 295                 300

Trp Ala Gly Asp Ile Pro Gly Met Ser Val Val Gly Arg Leu Lys
305                 310                 315                 320

Gln Val Asn Lys Arg Met Ile Arg Leu Val Ser Leu Ile His Asn Thr
                325                 330                 335

Val Arg Gly Ala Ala Gly Gly Gly Ile Leu Ala Ala Glu Leu Leu Val
                340                 345                 350

Glu Lys Gly Tyr Ile Glu Lys
        355

<210> SEQ ID NO 8
<211> LENGTH: 1080
<212> TYPE: DNA
<213> ORGANISM: Sulfolobus tokodaii

<400> SEQUENCE: 8
gtgatactca tgaggagaac attaaaagcc gcaatattag gtgctactgg tttagtagga      60
atcgaatacg taagaatgct atcaaatcat ccttatatta aaccagcata tttagctgga     120
aaaggttcag tgggtaaacc gtatggtgag gtagtaagat ggcaaacagt aggacaagtt     180
cctaaggaaa tagctgatat ggaaataaaa ccaactgatc ctaagttaat ggatgatgta     240
gacataatat tttctccatt acctcaaggt gctgctggcc cagtagaaga acaatttgca     300
aaagaaggat ccctgtgat tagtaattca ccagatcata gatttgatcc tgatgttccc      360
ttattggttc ctgaactaaa tcctcatact attagcttaa ttgatgagca agaaaaaga     420 agagaatgga aaggatttat agtaactaca ccactatgca cagcccaggg tgcagcaata     480
ccattaggtg ctatatttaa agattataag atggatggag catttataac tactattcaa     540
tcgctatctg gtgccggtta ccaggaata ccatcattag atgtagtaga taatatcttg      600
cctttaggtg atggatacga tgccaagacg ataaaagaga tcttcagaat tttaagcgaa     660
gttaagagaa atgtagatga acctaaatta gaagatgtaa gcttagcagc aacaactcat     720
agaatagcta ctatacatgg tcattatgaa gtactatatg tatcgttcaa agaggaaact     780
gctgctgaaa agttaagga gctttagaa aactttagag gggaaccaca agatctaaaa      840
ttaccaactg caccttcaaa gccaattatc gttatgaatg aggatacaag acctcaagtc     900
tattttgata gatgggctgg ggatattcca ggaatgagtg tagttgtagg tagattaaag     960
caagtgaata gagaatgat aaggttagta tcattaattc ataacacggt cagaggagcc    1020
gcaggaggag gtatattagc agctgaatta cttgtcgaaa aaggatatat tgaaaagtaa    1080

<210> SEQ ID NO 9
<211> LENGTH: 1080
<212> TYPE: DNA
```

<213> ORGANISM: Sulfolobus tokodaii

<400> SEQUENCE: 9

| | |
|---|---:|
| atgattctga tgcgccgtac cctgaaagcg gcaatcttgg gtgccaccgg cttagtcggg | 60 |
| attgagtacg tacggatgct gagcaatcat ccgtacatca aacccgccta tctggctggg | 120 |
| aaagggtcag ttggcaaacc gtatggcgaa gtagtgcgct ggcagactgt gggccaagtt | 180 |
| cccaaagaaa ttgccgatat ggaaatcaag ccgactgatc cgaaactgat ggatgatgtt | 240 |
| gacatcatct ttagcccact gcctcaaggt gcggcaggac ccgttgagga acaatttgcg | 300 |
| aaagaaggat ttccggtcat ttccaattct ccggatcatc ggtttgatcc ggatgtccca | 360 |
| ctcctggtgc cagaactgaa tccgcacacc attagcctta ttgacgaaca gcgtaaacgc | 420 |
| cgtgaatgga aaggcttcat cgttacgacg ccgttatgca ccgcacaggg tgctgcgatc | 480 |
| ccattgggtg ccatcttcaa ggactacaaa atggatggcg cattcattac gaccattcag | 540 |
| tctcttagcg gtgcgggata tccgggtatt ccgtccctgg atgtggtgga taacattctg | 600 |
| cctttagggg acggttatga cgccaaaacg atcaaggaaa ttttccgcat cctgagtgaa | 660 |
| gtgaaacgca atgtggacga acctaaactg gaggacgttt cactggccgc cacaacccat | 720 |
| cgcattgcaa ccattcatgg ccactatgag gtgttgtacg tgtcgtttaa ggaagaaaca | 780 |
| gcagcggaga aggtcaaaga aacgctggaa aactttcgcg gtgaacctca ggatctcaaa | 840 |
| ctgccgacag cgccctcgaa accgatcatt gtgatgaacg aagatactcg cccacaggta | 900 |
| tatttcgatc gttgggcggg cgacattccg ggcatgagtg tcgttgttgg ccgtctgaaa | 960 |
| caggtcaaca aacgcatgat tcgtctggta tcgcttatcc acaacaccgt acgtggtgct | 1020 |
| gcgggcggtg ggatttttagc tgcggagttg ctcgtggaga aaggctacat cgagaagtaa | 1080 |

<210> SEQ ID NO 10
<211> LENGTH: 451
<212> TYPE: PRT
<213> ORGANISM: Porphyromonas gingivalis

<400> SEQUENCE: 10

```
Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
        35                  40                  45

Val Asp Glu Thr Gly Met Gly Val Tyr Glu His Lys Val Ala Lys Asn
    50                  55                  60

Gln Gly Lys Ser Lys Gly Val Trp Tyr Asn Leu His Asn Lys Lys Ser
65                  70                  75                  80

Ile Gly Ile Leu Asn Ile Asp Glu Arg Thr Gly Met Ile Glu Ile Ala
                85                  90                  95

Lys Pro Ile Gly Val Val Gly Ala Val Thr Pro Thr Thr Asn Pro Ile
            100                 105                 110

Val Thr Pro Met Ser Asn Ile Ile Phe Ala Leu Lys Thr Cys Asn Ala
        115                 120                 125

Ile Ile Ile Ala Pro His Pro Arg Ser Lys Lys Cys Ser Ala His Ala
    130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
```

|     |     |     | 165 |     |     |     | 170 |     |     |     | 175 |     |
|---|---|---|---|---|---|---|---|---|---|---|---|---|

Met Gly Ala Val Asp Val Val Ala Thr Gly Gly Met Gly Met Val
                180                          185                          190

Lys Ser Ala Tyr Ser Ser Gly Lys Pro Ser Phe Gly Val Gly Ala Gly
    195                         200                          205

Asn Val Gln Val Ile Val Asp Ser Asn Ile Asp Phe Glu Ala Ala Ala
    210                         215                          220

Glu Lys Ile Ile Thr Gly Arg Ala Phe Asp Asn Gly Ile Ile Cys Ser
225                       230                         235                         240

Gly Glu Gln Ser Ile Ile Tyr Asn Glu Ala Asp Lys Glu Ala Val Phe
                245                          250                         255

Thr Ala Phe Arg Asn His Gly Ala Tyr Phe Cys Asp Glu Ala Glu Gly
            260                          265                         270

Asp Arg Ala Arg Ala Ala Ile Phe Glu Asn Gly Ala Ile Ala Lys Asp
        275                       280                         285

Val Val Gly Gln Ser Val Ala Phe Ile Ala Lys Lys Ala Asn Ile Asn
290                       295                         300

Ile Pro Glu Gly Thr Arg Ile Leu Val Val Glu Ala Arg Gly Val Gly
305                       310                         315                         320

Ala Glu Asp Val Ile Cys Lys Glu Lys Met Cys Pro Val Met Cys Ala
                325                          330                         335

Leu Ser Tyr Lys His Phe Glu Gly Val Glu Ile Ala Arg Thr Asn
            340                          345                         350

Leu Ala Asn Glu Gly Asn Gly His Thr Cys Ala Ile His Ser Asn Asn
        355                       360                         365

Gln Ala His Ile Ile Leu Ala Gly Ser Glu Leu Thr Val Ser Arg Ile
    370                       375                         380

Val Val Asn Ala Pro Ser Ala Thr Thr Ala Gly Gly His Ile Gln Asn
385                       390                         395                         400

Gly Leu Ala Val Thr Asn Thr Leu Gly Cys Gly Ser Trp Gly Asn Asn
                405                          410                         415

Ser Ile Ser Glu Asn Phe Thr Tyr Lys His Leu Leu Asn Ile Ser Arg
            420                          425                         430

Ile Ala Pro Leu Asn Ser Ser Ile His Ile Pro Asp Asp Lys Glu Ile
        435                       440                         445

Trp Glu Leu
    450

<210> SEQ ID NO 11
<211> LENGTH: 1356
<212> TYPE: DNA
<213> ORGANISM: Porphyromonas gingivalis

<400> SEQUENCE: 11

| | | | | | |
|---|---|---|---|---|---|
| atggaaatca | aagaaatggt | gagccttgca | cgcaaggctc | agaaggagta | tcaagctacc | 60 |
| cataaccaag | aagcagttga | caacatttgc | cgagctgcag | caaagttat | ttatgaaaat | 120 |
| gcagctattc | tggctcgcga | agcagtagac | gaaaccggca | tgggcgttta | cgaacacaaa | 180 |
| gtggccaaga | atcaaggcaa | atccaaaggt | gtttggtaca | acctccacaa | taaaaaatcg | 240 |
| attggtatcc | tcaatataga | cgagcgtacc | ggtatgatcg | agattgcaaa | gcctatcgga | 300 |
| gttgtaggag | ccgtaacgcc | gacgaccaac | ccgatcgtta | ctccgatgag | caatatcatc | 360 |
| tttgctctta | agacctgcaa | tgccatcatt | attgcccccc | accccagatc | caaaaaatgc | 420 |
| tctgcacacg | cagttcgtct | gatcaaagaa | gctatcgctc | cgttcaacgt | accggaaggt | 480 |

```
atggttcaga tcatcgaaga acccagcatc gagaagacgc aggaactcat gggcgccgta    540
gacgtagtag ttgctacggg tggtatgggc atggtgaagt ctgcatattc ttcaggaaag    600
ccttctttcg tgttggagc cggtaacgtt caggtgatcg tggatagcaa catcgatttc    660
gaagctgctg cagaaaaaat catcaccggt cgtgctttcg acaacggtat catctgctca    720
ggcgaacaga gcatcatcta caacgaggct gacaaggaag cagttttcac agcattccgc    780
aaccacggtg catatttctg tgacgaagcc gaaggagatc gggctcgtgc agctatcttc    840
gaaaatggag ccatcgcgaa agatgtagta ggtcagagcg ttgccttcat tgccaagaaa    900
gcaaacatca atatccccga gggtacccgt attctcgttg ttgaagctcg cggcgtagga    960
gcagaagacg ttatctgtaa ggaaaagatg tgtcccgtaa tgtgcgccct cagctacaag   1020
cacttcgaag aagtgtagaa atcgcacgt acgaacctcg ccaacgaagg taacggccac   1080
acctgtgcta tccactccaa caatcaggca cacatcatcc tcgcaggatc agagctgacg   1140
gtatctcgta tcgtagtgaa tgctccgagt gccactacag caggcggtca catccaaaac   1200
ggtcttgccg taaccaatac gctcggatgc ggatcatggg gtaataactc tatctccgag   1260
aacttcactt acaagcacct cctcaacatt tcacgcatcg caccgttgaa ttcaagcatt   1320
cacatccccg atgacaaaga aatctgggaa ctctaa                             1356
```

```
<210> SEQ ID NO 12
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 12
tataatgagc tcgtttaact ttaagaagga gatataccat gattctgatg cgccgt        56

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct - Primer for amplification

<400> SEQUENCE: 13
tataatggat ccctcgaatt cttacttctc                                     30

<210> SEQ ID NO 14
<211> LENGTH: 312
<212> TYPE: PRT
<213> ORGANISM: Saccharomyces cerevisiae

<400> SEQUENCE: 14
```

```
Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ala Ile Tyr Leu Asn Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
```

```
                85                  90                  95
Ser Lys Arg Leu Gly Leu Asp Tyr Val Asp Leu Tyr Leu Met His
            100                 105                 110

Trp Pro Val Pro Leu Lys Thr Asp Arg Val Thr Asp Gly Asn Val Leu
            115                 120                 125

Cys Ile Pro Thr Leu Glu Asp Gly Thr Val Asp Ile Asp Thr Lys Glu
            130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
            195                 200                 205

Cys Lys Glu Lys Gly Ile Val Val Glu Ala Tyr Ser Pro Phe Gly Ser
            210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
            260                 265                 270

Ser Asn Phe Lys Ile Phe Thr Leu Pro Glu Asp Asp Phe Lys Thr Ile
            275                 280                 285

Ser Asn Leu Ser Lys Val His Gly Thr Lys Arg Val Val Asp Met Lys
            290                 295                 300

Trp Gly Ser Phe Pro Ile Phe Gln
305                 310

<210> SEQ ID NO 15
<211> LENGTH: 939
<212> TYPE: DNA
<213> ORGANISM: Saccharomyces cerevisiae

<400> SEQUENCE: 15
atgcctgcta cgttaaagaa ttcttctgct acattaaaac taaatactgg tgcctccatt        60
ccagtgttgg gtttcggcac ttggcgttcc gttgacaata acggttacca ttctgtaatt       120
gcagctttga agctggata cagacacatt gatgctgcgg ctatctattt gaatgaagaa        180
gaagttggca gggctattaa agattccgga gtccctcgtg aggaaatttt tattactact       240
aagctttggg gtacggaaca acgtgatccg gaagctgctc taaacaagtc tttgaaaaga       300
ctaggcttgg attatgttga cctatatctg atgcattggc cagtgccttt gaaaaccgac       360
agagttactg atggtaacgt tctgtgcatt ccaacattag aagatggcac tgttgacatc       420
gatactaagg aatggaattt tatcaagacg tgggagttga tgcaagagtt gccaaagacg       480
ggcaaaacta agccgttgg tgtctctaat ttttctatta acaacattaa agaattatta       540
gaatctccaa ataacaaggt ggtaccagct actaatcaaa ttgaaattca tccattgcta       600
ccacaagacg aattgattgc cttttgtaag gaaaagggta ttgttgttga agcctactca       660
ccatttggga gtgctaatgc ccctttacta aagagcaag caattattga tatggctaaa       720
aagcacggcg ttgagccagc acagcttatt atcagttgga gtattcaaag aggctacgtt       780
gttctggcca atcggttaa tcctgaaaga attgtatcca attttaagat tttcactctg       840
```

```
cctgaggatg atttcaagac tattagtaac ctatccaaag tgcatggtac aaagagagtc    900
gttgatatga agtggggatc cttcccaatt ttccaatga                           939
```

<210> SEQ ID NO 16
<211> LENGTH: 360
<212> TYPE: PRT
<213> ORGANISM: Metallosphaera sedula

<400> SEQUENCE: 16

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
            20                  25                  30

Lys Ala Thr Gly Leu Cys His Ser Asp Val Asn Val Phe Glu Gly Lys
        35                  40                  45

Thr Pro Val Pro Pro Val Val Ala Gly His Glu Ile Ser Gly Ile
    50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu
        115                 120                 125

Ile Arg Thr Phe Leu Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205

Ile Ile Ala Val Gly Thr Lys Lys Trp Lys Leu Asp Arg Ala Met Glu
    210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Gly Pro Gln Val Val Ile Glu Ala
                245                 250                 255

Gly Gly Asn Glu Asp Thr Ile His Met Ala Leu Asp Ser Val Arg Ile
            260                 265                 270

Gly Gly Lys Val Val Leu Val Gly Leu Pro Pro Ala Thr Ala Met Ile
        275                 280                 285

Pro Ile Arg Val Ala Ser Ile Val Arg Gly Gly Ile Glu Val Val Gly
    290                 295                 300

Asn Tyr Gly Gly Arg Pro Arg Val Asp Met Pro Lys Leu Leu Glu Leu
305                 310                 315                 320

Val Arg Gln Gly Arg Tyr Asp Pro Ser Arg Leu Val Thr Gly Arg Phe
                325                 330                 335

Arg Leu Glu Glu Ile Asn Glu Ala Val Lys Met Leu Glu Glu Gly Glu
            340                 345                 350

```
Ala Ile Arg Ser Leu Ile Ile Pro
        355             360
```

<210> SEQ ID NO 17
<211> LENGTH: 1083
<212> TYPE: DNA
<213> ORGANISM: Metallosphaera sedula

<400> SEQUENCE: 17

```
atgaaagctg cagtacttca tacgtataag gaaccgctgt ccattgagga cgtgaatatc      60
tcccaaccta aggctgggga agtcaagatc aaggtcaagg caaccgggct ctgtcactcc     120
gacgtcaatg tctttgaggg gaaaacccca gttcctcccc cagtggttgc tggacacgaa     180
atatcaggga ttgtggagga agtgggacct ggggtgacca gggttaaacc aggtgatagg     240
gtgatttcag cgtttattca ccctgtggt aaatgcggta actgcgttgc aggaaaggag      300
aatctgtgtg agaccttctc ccaggtcaga ctcaagggag taatgccaga tggaacgtca     360
aggctgtcaa aggacggaaa ggagataagg actttccttg gaggcggttt cgcggagtac     420
gccattgtgg gagagaacgc gctaaccagg gttccagagg acatggacct agagaaggta     480
gctgtcctag gttgtgctgg gttaacaggg tacggtgcca tatcatcatc caagattgag     540
cctggagaca ctgtggccgt gataggcgta ggaggagtgg gtttgtccac aatacaactc     600
ctaagggcct cgggtgccgg gaggataatc gccgtgggaa cgaaaaagtg gaaacttgac     660
agggccatgg agctaggtgc aactgacgtg gtaaactcga aggagataga tcccgtcaaa     720
gcaataaagg agatcacggg tggagggcca caggtggtga tagaggctgg aggaaatgag     780
gatacgattc atatggcgct ggattcagtt agaattggag gaaaggtggt tctggtaggg     840
ttacctccag caacggccat gatacccatc agggtagcgt caatagttag ggggaggcata     900
gaggttgtgg ggaattacgg aggaagacct agggttgata tgcccaagct tctcgagcta     960
gtgaggcagg gaagatacga tccgtctagg cttgtgacgg gtagattcag gttggaggaa    1020
ataaatgagg cagtcaaaat gcttgaggaa ggagaggcca taagaagtct cataatcccg    1080
taa                                                                  1083
```

<210> SEQ ID NO 18
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 18

```
tataatgcta gcatgcctgc tacgttaaag aa                                     32
```

<210> SEQ ID NO 19
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 19

```
tataatgagc tctcattgga aaattgggaa gg                                     32
```

<210> SEQ ID NO 20
<211> LENGTH: 46
<212> TYPE: DNA
<213> ORGANISM: Artificial Sequence
<220> FEATURE:

<223> OTHER INFORMATION: Synthetic Construct - Primer for amplification

<400> SEQUENCE: 20
tataatgaat tcttagcggg cggcttcgta tatacggcgg ctgaca           46

<210> SEQ ID NO 21
<211> LENGTH: 34
<212> TYPE: DNA
<213> ORGANISM: Artificial Sequence
<220> FEATURE:
<223> OTHER INFORMATION: Synthetic Construct - Primer for amplification

<400> SEQUENCE: 21
tatcgtgcta gcatgaacaa ctttaatctg caca                         34

<210> SEQ ID NO 22
<211> LENGTH: 27
<212> TYPE: DNA
<213> ORGANISM: Artificial Sequence
<220> FEATURE:
<223> OTHER INFORMATION: Synthetic Construct - Primer for amplification

<400> SEQUENCE: 22
tataatcata tgcaactttt caaactc                                 27

<210> SEQ ID NO 23
<211> LENGTH: 31
<212> TYPE: DNA
<213> ORGANISM: Artificial Sequence
<220> FEATURE:
<223> OTHER INFORMATION: Synthetic Construct - Primer for amplification

<400> SEQUENCE: 23
tataatggat ccttagtaga gtcttctgta g                            31

<210> SEQ ID NO 24
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 24
tataatgcta gcatgaaagc tgcagtactt ca                           32

<210> SEQ ID NO 25
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 25
tataatgaat tcttacggga ttatgagact tc                           32

<210> SEQ ID NO 26
<211> LENGTH: 37
<212> TYPE: DNA
<213> ORGANISM: Artificial Sequence
<220> FEATURE:
<223> OTHER INFORMATION: Synthetic Construct - Primer for amplification
<220> FEATURE:
<221> NAME/KEY: misc_feature
<222> LOCATION: (23)..(24)
<223> OTHER INFORMATION: n is a, c, g, or t

<400> SEQUENCE: 26

```
cattctgcct ttaggggacg gcnnkgacgc caaaacg                                37
```

<210> SEQ ID NO 27
<211> LENGTH: 37
<212> TYPE: DNA
<213> ORGANISM: Artificial Sequence
<220> FEATURE:
<223> OTHER INFORMATION: Synthetic Construct - Primer for amplification
<220> FEATURE:
<221> NAME/KEY: misc_feature
<222> LOCATION: (14)..(15)
<223> OTHER INFORMATION: n is a, c, g, or t

<400> SEQUENCE: 27

```
cgttttggcg tcmnngccgt ccoctaaagg cagaatg                                37
```

<210> SEQ ID NO 28
<211> LENGTH: 37
<212> TYPE: DNA
<213> ORGANISM: Artificial Sequence
<220> FEATURE:
<223> OTHER INFORMATION: Synthetic Construct - Primer for amplification

<400> SEQUENCE: 28

```
gtcaaggcaa ccggtctctg tcgctccgac gtcaatg                                37
```

<210> SEQ ID NO 29
<211> LENGTH: 37
<212> TYPE: DNA
<213> ORGANISM: Artificial Sequence
<220> FEATURE:
<223> OTHER INFORMATION: Synthetic Construct - Primer for amplification

<400> SEQUENCE: 29

```
cattgacgtc ggagcgacag agaccggttg ccttgac                                37
```

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct - Primer for amplification

<400> SEQUENCE: 30

```
ggctctgtca ctccgacgta catgtctttg aggggaaaac                             40
```

<210> SEQ ID NO 31
<211> LENGTH: 40
<212> TYPE: DNA
<213> ORGANISM: Artificial Sequence
<220> FEATURE:
<223> OTHER INFORMATION: Synthetic Construct - Primer for amplification

<400> SEQUENCE: 31

```
gttttcccct caaagacatg tacgtcggag tgacagagcc                             40
```

<210> SEQ ID NO 32
<211> LENGTH: 360
<212> TYPE: PRT
<213> ORGANISM: Metallosphaera sedula

<400> SEQUENCE: 32

```
Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
```

```
                    20                  25                  30
Lys Ala Thr Gly Leu Cys Arg Ser Asp Val Asn Val Phe Glu Gly Lys
                35                  40                  45

Thr Pro Val Pro Pro Val Ala Gly His Glu Ile Ser Gly Ile
         50                  55                  60

Val Glu Glu Val Gly Pro Gly Val Thr Arg Val Lys Pro Gly Asp Arg
 65                  70                  75                  80

Val Ile Ser Ala Phe Ile His Pro Cys Gly Lys Cys Gly Asn Cys Val
                 85                  90                  95

Ala Gly Lys Glu Asn Leu Cys Glu Thr Phe Ser Gln Val Arg Leu Lys
             100                 105                 110

Gly Val Met Pro Asp Gly Thr Ser Arg Leu Ser Lys Asp Gly Lys Glu
             115                 120                 125

Ile Arg Thr Phe Leu Gly Gly Phe Ala Glu Tyr Ala Ile Val Gly
         130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                 165                 170                 175

Ser Lys Ile Glu Pro Gly Asp Thr Val Ala Val Ile Gly Val Gly Gly
             180                 185                 190

Val Gly Leu Ser Thr Ile Gln Leu Leu Arg Ala Ser Gly Ala Gly Arg
         195                 200                 205

Ile Ile Ala Val Gly Thr Lys Lys Trp Lys Leu Asp Arg Ala Met Glu
     210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Pro Gln Val Val Ile Glu Ala
                 245                 250                 255

Gly Gly Asn Glu Asp Thr Ile His Met Ala Leu Asp Ser Val Arg Ile
             260                 265                 270

Gly Gly Lys Val Val Leu Val Gly Leu Pro Pro Ala Thr Ala Met Ile
         275                 280                 285

Pro Ile Arg Val Ala Ser Ile Val Arg Gly Gly Ile Glu Val Val Gly
     290                 295                 300

Asn Tyr Gly Gly Arg Pro Arg Val Asp Met Pro Lys Leu Leu Glu Leu
305                 310                 315                 320

Val Arg Gln Gly Arg Tyr Asp Pro Ser Arg Leu Val Thr Gly Arg Phe
                 325                 330                 335

Arg Leu Glu Glu Ile Asn Glu Ala Val Lys Met Leu Glu Glu Gly Glu
             340                 345                 350

Ala Ile Arg Ser Leu Ile Ile Pro
         355                 360

<210> SEQ ID NO 33
<211> LENGTH: 1083
<212> TYPE: DNA
<213> ORGANISM: Metallosphaera sedula

<400> SEQUENCE: 33
atgaaagctg cagtacttca tacgtataag gaaccgctgt ccattgagga cgtgaatatc      60
tcccaaccta aggctgggga agtcaagatc aaggtcaagg caaccggtct ctgtcgctcc     120
gacgtcaatg tctttgaggg gaaaacccca gttcctcccc cagtggttgc tggacacgaa     180
```

```
atatcaggga ttgtggagga agtgggacct ggggtgacca gggttaaacc aggtgatagg    240
gtgatttcag cgtttattca ccctgtggt aaatgcggta actgcgttgc aggaaaggag    300
aatctgtgtg agaccttctc ccaggtcaga ctcaaggag taatgccaga tggaacgtca    360
aggctgtcaa aggacggaaa ggagataagg actttccttg gaggcggttt cgcggagtac    420
gccattgtgg gagagaacgc gctaaccagg gttccagagg acatggacct agagaaggta    480
gctgtcctag gttgtgctgg gttaacaggg tacggtgcca tatcatcatc caagattgag    540
cctggagaca ctgtggccgt gataggcgta ggaggagtgg gtttgtccac aatacaactc    600
ctaagggcct cgggtgccgg gaggataatc gccgtgggaa cgaaaaagtg gaaacttgac    660
agggccatgg agctaggtgc aactgacgtg gtaaactcga aggagataga tcccgtcaaa    720
gcaataaagg agatcacggg tggagggcca caggtggtga tagaggctgg aggaaatgag    780
gatacgattc atatggcgct ggattcagtt agaattggag gaaaggtggt tctggtaggg    840
ttacctccag caacggccat gatacccatc agggtagcgt caatagttag gggaggcata    900
gaggttgtgg ggaattacgg aggaagacct agggttgata tgcccaagct tctcgagcta    960
gtgaggcagg gaagatacga tccgtctagg cttgtgacgg gtagattcag gttggaggaa   1020
ataaatgagg cagtcaaaat gcttgaggaa ggagaggcca taagaagtct cataatcccg   1080
taa                                                                  1083

<210> SEQ ID NO 34
<211> LENGTH: 360
<212> TYPE: PRT
<213> ORGANISM: Metallosphaera sedula

<400> SEQUENCE: 34

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
                20                  25                  30

Lys Ala Thr Gly Leu Cys His Ser Asp Val His Val Phe Glu Gly Lys
            35                  40                  45

Thr Pro Val Pro Pro Val Ala Gly His Glu Ile Ser Gly Ile
        50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu
        115                 120                 125

Ile Arg Thr Phe Leu Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205
```

```
Ile Ile Ala Val Gly Thr Lys Lys Trp Lys Leu Asp Arg Ala Met Glu
210                 215                 220
Leu Gly Ala Thr Asp Val Val Asn Ser Lys Glu Ile Asp Pro Val Lys
225                 230                 235                 240
Ala Ile Lys Glu Ile Thr Gly Gly Pro Gln Val Val Ile Glu Ala
            245                 250                 255
Gly Gly Asn Glu Asp Thr Ile His Met Ala Leu Asp Ser Val Arg Ile
                260                 265                 270
Gly Gly Lys Val Val Leu Val Gly Leu Pro Pro Ala Thr Ala Met Ile
            275                 280                 285
Pro Ile Arg Val Ala Ser Ile Val Arg Gly Gly Ile Glu Val Val Gly
290                 295                 300
Asn Tyr Gly Gly Arg Pro Arg Val Asp Met Pro Lys Leu Leu Glu Leu
305                 310                 315                 320
Val Arg Gln Gly Arg Tyr Asp Pro Ser Arg Leu Val Thr Gly Arg Phe
                325                 330                 335
Arg Leu Glu Glu Ile Asn Glu Ala Val Lys Met Leu Glu Glu Gly Glu
                340                 345                 350
Ala Ile Arg Ser Leu Ile Ile Pro
            355                 360

<210> SEQ ID NO 35
<211> LENGTH: 1083
<212> TYPE: DNA
<213> ORGANISM: Metallosphaera sedula

<400> SEQUENCE: 35
atgaaagctg cagtacttca tacgtataag gaaccgctgt ccattgagga cgtgaatatc      60
tcccaaccta aggctgggga agtcaagatc aaggtcaagg caaccgggct ctgtcactcc     120
gacgtacatg tctttgaggg gaaaaccca gttcctcccc cagtggttgc tggacacgaa      180
atatcaggga ttgtggagga agtgggacct ggggtgacca gggttaaacc aggtgatagg     240
gtgatttcag cgtttattca ccctgtggt aaatgcggta actgcgttgc aggaaaggag      300
aatctgtgtg agaccttctc ccaggtcaga ctcaagggag taatgccaga tggaacgtca     360
aggctgtcaa aggacggaaa ggagataagg actttccttg gaggcggttt cgcggagtac     420
gccattgtgg gagagaacgc gctaaccagg gttccagagg acatggacct agagaaggta     480
gctgtcctag gttgtgctgg gttaacaggg tacggtgcca tcatcatc caagattgag       540
cctggagaca ctgtggccgt gataggcgta ggaggagtgg gttgtccac aatacaactc      600
ctaagggcct cggggtgccgg gaggataatc gccgtgggaa cgaaaaagtg gaaacttgac    660
agggccatgg agctaggtgc aactgacgtg gtaaactcga aggagataga tcccgtcaaa    720
gcaataaagg agatcacggg tggagggcca caggtggtga tagaggctgg aggaaatgag    780
gatacgattc atatggcgct ggattcagtt agaattggag aaggtggt tctggtaggg      840
ttacctccag caacggccat gataccatc agggtagcgt caatagttag ggaggcata     900
gaggttgtgg gaattacgg aggaagacct agggttgata tgcccaagct tctcgagcta     960
gtgaggcagg gaagatacga tccgtctagg cttgtgacgg gtagattcag gttggaggaa   1020
ataaatgagg cagtcaaaat gcttgaggaa ggagaggcca taagaagtct cataatcccg   1080
taa                                                                 1083

<210> SEQ ID NO 36
<211> LENGTH: 360
```

<212> TYPE: PRT
<213> ORGANISM: Metallosphaera sedula

<400> SEQUENCE: 36

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
            20                  25                  30

Lys Ala Thr Gly Leu Cys Arg Ser Asp Val His Val Phe Glu Gly Lys
        35                  40                  45

Thr Pro Val Pro Pro Val Ala Gly His Glu Ile Ser Gly Ile
    50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu
        115                 120                 125

Ile Arg Thr Phe Leu Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205

Ile Ile Ala Val Gly Thr Lys Lys Trp Lys Leu Asp Arg Ala Met Glu
    210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Pro Gln Val Val Ile Glu Ala
                245                 250                 255

Gly Gly Asn Glu Asp Thr Ile His Met Ala Leu Asp Ser Val Arg Ile
            260                 265                 270

Gly Gly Lys Val Val Leu Val Gly Leu Pro Pro Ala Thr Ala Met Ile
        275                 280                 285

Pro Ile Arg Val Ala Ser Ile Val Arg Gly Gly Ile Glu Val Val Gly
    290                 295                 300

Asn Tyr Gly Gly Arg Pro Arg Val Asp Met Pro Lys Leu Leu Glu Leu
305                 310                 315                 320

Val Arg Gln Gly Arg Tyr Asp Pro Ser Arg Leu Val Thr Gly Arg Phe
                325                 330                 335

Arg Leu Glu Glu Ile Asn Glu Ala Val Lys Met Leu Glu Glu Gly Glu
            340                 345                 350

Ala Ile Arg Ser Leu Ile Pro
        355                 360

<210> SEQ ID NO 37
<211> LENGTH: 1083
<212> TYPE: DNA
<213> ORGANISM: Metallosphaera sedula

<400> SEQUENCE: 37

```
atgaaagcag cagttctgca tacctataaa gaaccgctga gcattgaaga tgtgaatatt      60
tcacagccga agccggtga agtgaaaatc aaagttaaag caaccggtct gtgtcgtagt      120
gatgttcatg ttttttgaagg taaaacaccg gttccgcctc cggttgttgc aggtcatgaa    180
attagcggta ttgttgaaga ggttggtccg ggtgttaccc gtgttaaacc gggtgatcgt    240
gttattagcg catttattca tccgtgtggt aaatgcggta attgtgttgc cggtaaagaa    300
aatctgtgtg aaacctttag ccaggttcgt ctgaaaggtg ttatgccgga tggcaccagc    360
cgtctgagca agatggcaa agaaattcgt acctttctgg gtggtggttt tgcagaatat    420
gcaattgttg gtgaaaatgc actgacccgt gttccggaag atatggatct ggaaaaagtt    480
gcagttctgg ttgtgccgg tctgaccggt tatggtgcaa ttagcagcag caaaattgaa    540
cctggtgata ccgttgcagt tattggtgtt ggtggtgtgg gtctgagcac cattcagctg    600
ctgcgtgcaa gcggtgcagg tcgtattatt gcagttggca ccaaaaaatg gaaactggat    660
cgtgcaatgg aactgggtgc aaccgatgtt gttaacagta aagaaattga tccggtgaaa    720
gccatcaaag aaatcaccgg tggtggtccg caggttgtta ttgaagccgg tggtaatgaa    780
gataccattc acatggcact ggatagcgtt cgtattggtg gtaaagttgt tctggttggt    840
ctgcctccgg caaccgcaat gattccgatt cgtgttgcaa gcattgttcg tggtggtatt    900
gaagttgttg gtaattatgg tggtcgtccg cgtgttgata tgccgaaact gctggaactg    960
gttcgtcagg tcgttatga tccgagccgt ctggttaccg tcgttttcg tctggaagaa    1020
attaatgaag ccgtcaaaat gctggaagaa ggtgaagcaa ttcgtagcct gattattccg    1080
taa                                                                   1083
```

<210> SEQ ID NO 38
<211> LENGTH: 1083
<212> TYPE: DNA
<213> ORGANISM: Metallosphaera sedula

<400> SEQUENCE: 38

```
atgaaagcag cagttctgca tacctataaa gaaccgctga gcattgaaga tgtgaatatt      60
tcacagccga agccggtga agtgaaaatc aaagttaaag caaccggtct gtgtcgtagt      120
gatgttcatg ttttttgaagg taaaacaccg gttccgcctc cggttgttgc aggtcatgaa    180
attagcggta ttgttgaaga ggttggtccg ggtgttaccc gtgttaaacc gggtgatcgt    240
gttattagcg catttattca tccgtgtggt aaatgcggta attgtgttgc cggtaaagaa    300
aatctgtgtg aaacctttag ccaggttcgt ctgaaaggtg ttatgccgga tggcaccagc    360
cgtctgagca agatggcaa agaaattcgt acctttctgg gtggtggttt tgcagaatat    420
gcaattgttg gtgaaaatgc actgacccgt gttccggaag atatggatct ggaaaaagtt    480
gcagttctgg ttgtgccgg tctgaccggt tatggtgcaa ttagcagcag caaaattgaa    540
cctggtgata ccgttgcagt tattggtgtt ggtggtgtgg gtctgagcac cattcagctg    600
ctgcgtgcaa gcggtgcagg tcgtattatt gcagttggca ccaaaaaatg gaaactggat    660
cgtgcaatgg aactgggtgc aaccgatgtt gttaacagta aagaaattga tccggtgaaa    720
gccatcaaag aaatcaccgg tggtggtccg caggttgtta ttgaagccgg tggtaatgaa    780
gataccattc acatggcact ggatagcgtt cgtattggtg gtaaagttgt tctggttggt    840
ctgcctccgg caaccgcaat gattccgatt cgtgttgcaa gcattgttcg tggtggtatt    900
```

```
gaagttgttg gtaattatgg tggtcgtccg cgtgttgata tgccgaaact gctggaactg    960
gttcgtcagg gtcgttatga tccgagccgt ctggttaccg gtcgttttcg tctggaagaa   1020
attaatgaag ccgtcaaaat gctggaagaa ggtgaagcaa ttcgtagcct gattattccg   1080
taa                                                                 1083

<210> SEQ ID NO 39
<211> LENGTH: 60
<212> TYPE: DNA
<213> ORGANISM: Artificial Sequence
<220> FEATURE:
<223> OTHER INFORMATION: Synthetic Construct - Primer for amplification

<400> SEQUENCE: 39
tcacacagga aacagaattc gagctcggta atgtcgttta ccctgattca gcaagcgact     60

<210> SEQ ID NO 40
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 40
ggtatatctc cttcttaaag ttaaacttat ttgccgccca ttgcatccgc tttctg         56

<210> SEQ ID NO 41
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 41
gtttaacttt aagaaggaga tataccatga ttctgatgcg ccgtaccctg aaagcg         56

<210> SEQ ID NO 42
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 42
ggtatatctc cttcttaaag ttaaacttac ttctcgatgt agccttttctc cacgag        56

<210> SEQ ID NO 43
<211> LENGTH: 70
<212> TYPE: DNA
<213> ORGANISM: Artificial Sequence
<220> FEATURE:
<223> OTHER INFORMATION: Synthetic Construct - Primer for amplification

<400> SEQUENCE: 43
gtttaacttt aagaaggaga tataccatga aagcagcagt tctgcatacc tataaagaac     60
cgctgagcat                                                            70

<210> SEQ ID NO 44
<211> LENGTH: 58
<212> TYPE: DNA
<213> ORGANISM: Artificial Sequence
<220> FEATURE:
<223> OTHER INFORMATION: Synthetic Construct - Primer for amplification

<400> SEQUENCE: 44
```

<210> SEQ ID NO 45
<211> LENGTH: 8457
<212> TYPE: DNA
<213> ORGANISM: Artificial Sequence
<220> FEATURE:
<223> OTHER INFORMATION: Synthetic Construct - pACT-MCL-DHB

<400> SEQUENCE: 45

```
atgcctgcag gtcgactcta gaggatcctt acggaataat caggctacga attgcttc      58
```

```
ttcgagctcg gtaatgtcgt ttaccctgat tcagcaagcg actccgcgct tacatcgcag      60
cgaacttgcg gttccgggtt caaatccgac ctttatggag aaatcagcag ccagcaaggc     120
cgatgtcatc ttcttggatc tggaggatgc cgttgcacct gatgacaaag aacaggcgcg     180
taagaacatc attcaggcac tgaacgatct ggactgggc aacaaaacga tgatgatccg     240
cattaacggt ctggacaccc actacatgta tcgggatgtg gtcgacatcg tagaagcatg     300
ccctcgcctg gatatgattc tcattcccaa agtcggagta ccagcagacg tgtatgcgat     360
tgatgtgctg acgacgcaaa tcgaacaggc gaagaaacgg gagaagaaaa tcggattcga     420
ggtgctcatt gaaacggctt taggcatggc caatgttgaa gccatcgcca catcttcgaa     480
acgcttggaa gcgatgtcgt ttggtgtggc cgattatgca gcatccactc gtgcccgtag     540
taccgtgatt ggtggtgtga atgcggatta ctccgttctc actgacaaag atgaagcagg     600
gaaccgtcaa acccattggc aagatccgtg gctgtttgcg cagaatcgca tgctggttgc     660
ttgccgtgct tacgggcttc gcccgattga tgggccattt ggcgacttca gcgatcccga     720
tggctatacc agtgctgcgc gtcgttgtgc ggcgctgggc tttgaaggca aatgggcgat     780
tcacccgagt cagatcgact tagcgaacga ggtgttcaca ccgtctgaag ctgaagtcac     840
caaagcgcgc cgcattctgg aggcaatgga agaagcggcc aaagccggtc gtggcgctgt     900
aagcctggac ggtcgcttga ttgacatcgc cagcattcgc atggctgaag ccctgatcca     960
gaaagcggat gcaatgggcg gcaaataagt ttaactttaa gaaggagata taccatgatt    1020
ctgatgcgcc gtaccctgaa agcggcaatc ttgggtgcca ccggcttagt cgggattgag    1080
tacgtacgga tgctgagcaa tcatccgtac atcaaacccg cctatctggc tgggaaaggg    1140
tcagttggca aaccgtatgg cgaagtagtg cgctggcaga ctgtgggcca agttcccaaa    1200
gaaattgccg atatggaaat caagccgact gatccgaaac tgatggatga tgttgacatc    1260
atctttagcc cactgcctca aggtgcggca ggacccgttg aggaacaatt gcgaaagaa    1320
ggatttccgg tcatttccaa ttctccggat catcggtttg atccggatgt cccactcctg    1380
gtgccagaac tgaatccgca caccattagc cttattgacg aacagcgtaa acgccgtgaa    1440
tggaaaggct tcatcgttac gacgccgtta tgcaccgcac agggtgctgc gatcccattg    1500
ggtgccatct tcaaggacta caaaatggat ggcgcattca ttacgaccat tcagtctctt    1560
agcggtgcgg gatatccggg tattccgtcc ctggatgtgg tggataacat tctgcctta    1620
ggggacggtt atgacgccaa aacgatcaag gaaattttcc gcatcctgag tgaagtgaaa    1680
cgcaatgtgg acgaacctaa actgaggac gtttcactgg ccgccacaac ccatcgcatt    1740
gcaaccattc atgccactga tgaggtgttg tacgtgtcgt ttaaggaaga aacagcagcg    1800
gagaaggtca agaaacgct ggaaaacttt cgcggtgaac ctcaggatct caaactgccg    1860
acagcgccct cgaaaccgat cattgtgatg aacgaagata ctcgcccaca ggtatatttc    1920
gatcgttggg cgggcgacat tccgggcatg agtgtcgttg ttggccgtct gaaacaggtc    1980
```

```
aacaaacgca tgattcgtct ggtatcgctt atccacaaca ccgtacgtgg tgctgcgggc    2040
ggtgggattt tagctgcgga gttgctcgtg gagaaaggct acatcgagaa gtaagtttaa    2100
ctttaagaag gagatatacc atgaaagcag cagttctgca tacctataaa gaaccgctga    2160
gcattgaaga tgtgaatatt tcacagccga agccggtgaa agtgaaaatc aaagttaaag    2220
caaccggtct gtgtcgtagt gatgttcatg tttttgaagg taaaacaccg gttccgcctc    2280
cggttgttgc aggtcatgaa attagccgta ttgttgaaga ggttggtccg ggtgttaccc    2340
gtgttaaacc gggtgatcgt gttattagcg catttattca tccgtgtggt aaatgcggta    2400
attgtgttgc cggtaaagaa aatctgtgtg aaacctttag ccaggttcgt ctgaaaggtg    2460
ttatgccgga tggcaccagc cgtctgagca agatggcaa agaaattcgt acctttctgg     2520
gtggtggttt tgcagaatat gcaattgttg gtgaaaatgc actgacccgt gttccggaag    2580
atatggatct ggaaaaagtt gcagttctgg gttgtgccgg tctgaccggt tatggtgcaa    2640
ttagcagcag caaaattgaa cctggtgata ccgttgcagt tattggtgtt ggtggtgtgg    2700
gtctgagcac cattcagctg ctgcgtgcaa gcggtgcagg tcgtattatt gcagttggca    2760
ccaaaaaatg gaactggat cgtgcaatgg aactgggtgc aaccgatgtt gttaacagta     2820
aagaaattga tccggtgaaa gccatcaaag aaatcaccgg tggtggtccg caggttgtta    2880
ttgaagccgg tggtaatgaa gataccattc acatggcact ggatagcgtt cgtattggtg    2940
gtaaagttgt tctggttggt ctgcctccgg caaccgcaat gattccgatt cgtgttgcaa    3000
gcattgttcg tggtggtatt gaagttgttg gtaattatgg tggtcgtccg cgtgttgata    3060
tgccgaaact gctggaactg gttcgtcagg gtcgttatga tccgagccgt ctggttaccg    3120
gtcgttttcg tctggaagaa attaatgaag ccgtcaaaat gctggaagaa ggtgaagcaa    3180
ttcgtagcct gattattccg taagatcctc tagagtcgac ctgcaggcat gcaagcttct    3240
gttttggcgg atgagagaag aaattcgtcg cccgccataa actgccaggc atcaaattaa    3300
gcagaaggcc atcctgacgg atggccttt tgcgtttcta caaactcttc ctgtctagca     3360
ggtggcactt ttcggggaaa tgtgcgcgga accctatt gtttattttt ctaaatacat      3420
tcaaatatgt atccgctcat gctagaaata tttatctga ttaataagat gatcttcttg     3480
agatcgtttt ggtctgcgcg taatctcttg ctctgaaaac gaaaaaaccg ccttgcaggg    3540 cggttttttcg aaggttctct gagctaccaa ctctttgaac cgaggtaact ggcttggagg   3600
agcgcagtca ccaaaacttg tcctttcagt ttagccttaa ccggcgcatg acttcaagac    3660
taactcctct aaatcaatta ccagtggctg ctgccagtgg tgcttttgca tgtctttccg    3720
ggttggactc aagacgatag ttaccggata aggcgcagcg gtcggactga acgggggggtt   3780 cgtgcataca gtccagcttg gagcgaactg cctacccgga actgagtgtc aggcgtggaa    3840
tgagacaaac gcggccataa cagcggaatg acaccggtaa accgaaaggc aggaacagga    3900
gagcgcacga gggagccgcc aggggaaacg cctggtatct ttatagtcct gtcgggtttc    3960
gccaccactg atttgagcgt cagatttcgt gatgcttgtc aggggggcgg agcctatgga    4020
aaaacggctt tgccgcggcc ctctcacttc cctgttaagt atcttcctgg catcttccag    4080
gaaatctccg ccccgttcgt aagccatttc cgctcgccgc agtcgaacga ccagcgtag     4140 cgagtcagtg agcgaggaag cggaatatat cctgtatcac atattctgct gacgcaccgg    4200
tgcagccttt tttctcctgc cacatgaagc acttcactga caccctcatc agtgccaaca    4260
tagtaagcca gtatacactc cgctagcgct gatgtccggc ggtgcttttg ccgttacgca    4320 ccacccccgtc agtagctgaa caggagggac agctgataga aacagaagcc actggagcac    4380
```

```
ctcaaaaaca ccatcataca ctaaatcagt aagttggcag catcacccga cgcactttgc    4440
gccgaataaa tacctgtgac ggaagatcac ttcgcagaat aaataaatcc tggtgtccct    4500
gttgataccg ggaagccctg ggccaacttt tggcgaaaat gagacgttga tcggcacgta    4560
agaggttcca actttcacca taatgaaata agatcactac cgggcgtatt ttttgagtta    4620
tcgagatttt caggagctaa ggaagctaaa atggagaaaa aaatcactgg atataccacc    4680
gttgatatat cccaatggca tcgtaaagaa cattttgagg catttcagtc agttgctcaa    4740
tgtacctata accagaccgt tcagctggat attacggcct ttttaaagac cgtaaagaaa    4800
aataagcaca gtttatatcc ggcctttatt cacattcttg cccgcctgat gaatgctcat    4860
ccggaattcc gtatggcaat gaaagacggt gagctggtga tatgggatag tgttcaccct    4920
tgttacaccg ttttccatga gcaaactgaa acgttttcat cgctctggag tgaataccac    4980
gacgatttcc ggcagtttct acacatatat tcgcaagatg tggcgtgtta cggtgaaaac    5040
ctggcctatt tccctaaagg gtttattgag aatatgtttt tcgtctcagc caatccctgg    5100
gtgagtttca ccagttttga tttaaacgtg gccaatatgg acaacttctt cgcccccgtt    5160
ttcaccatgg gcaaatatta tacgcaaggc gacaaggtgc tgatgccgct ggcgattcag    5220
gttcatcatg ccgtctgtga tggcttccat gtcggcagaa tgcttaatga attacaacag    5280
tactgcgatg agtggcaggg cggggcgtaa ttttttttaag gcagttattg gtgcccttaa    5340
acgcctggtg ctacgcctga ataagtgata ataagcggat gaatggcaga aattcgaaag    5400
caaattcgac ccggtcgtcg gttcaggca gggtcgttaa atagccgctt atgtctattg    5460
ctggtttacc ggtttattga ctaccggaag cagtgtgacc gtgtgcttct caaatgcctg    5520
aggccagttt gctcaggctc tccccgtgga ggtaataatt gacgatatga tcatttattc    5580
tgcctcccag agcctgataa aaacggttag cgcttcgtta atacagatgt aggtgttcca    5640
cagggtagcc agcagcatcc tgcgatgcag atccggaaca taatggtgca gggcgcttgt    5700
ttcggcgtgg gtatggtggc aggccccgtg gccggggac tgttgggcgc tgccggcacc    5760
tgtcctacga gttgcatgat aaagaagaca gtcataagtg cggcgacgat agtcatgccc    5820
cgcgcccacc ggaaggagct accggacagc ggtgcggact gttgtaactc agaataagaa    5880
atgaggccgc tcatggcgtt gactctcagt catagtatcg tggtatcacc ggttggttcc    5940
actctctgtt gcgggcaact tcagcagcac gtaggggact tccgcgtttc cagactttac    6000
gaaacacgga aaccgaagac cattcatgtt gttgctcagg tcgcagacgt tttgcagcag    6060
cagtcgcttc acgttcgctc gcgtatcggt gattcattct gctaaccagt aaggcaaccc    6120
cgccagccta gccgggtcct caacgacagg agcacgatca tgcgcacccg tggccaggac    6180
ccaacgctgc ccgagatgcg ccgcgtgcgg ctgctggaga tggcggacgc gatggatatg    6240
ttctgccaag ggttggtttg cgcattcaca gttctccgca agaattgatt ggctccaatt    6300
cttggagtgt gaatccgtt agcgaggtgc cgccggcttc cattcaggtc gaggtggccc    6360
ggctccatgc accgcgacgc aacgcgggga ggcagacaag gtatagggcg cgcctacaa    6420 tccatgccaa cccgttccat gtgctcgccg aggcggcata aatcgccgtg acgatcagcg    6480
gtccagtgat cgaagttagg ctggtaagag ccgcgagcga tccttgaagc tgtccctgat    6540
ggtcgtcatc tacctgcctg gacagcatgg cctgcaacgc gggcatcccg atgccgccgg    6600
aagcgagaag aatcataatg gggaaggcca tccagcctcg cgtcgcgaac gccagcaaga    6660
cgtagcccag cgcgtcggcc aattcgcgct aacttacatt aattgcgttg cgctcactgc    6720
```

| | | |
|---|---|---|
| ccgctttcca gtcgggaaac ctgtcgtgcc agctgcatta atgaatcggc caacgcgcgg | 6780 | |
| ggagaggcgg tttgcgtatt gggcgccagg gtggtttttc ttttcaccag tgagacgggc | 6840 | |
| aacagctgat tgcccttcac cgcctggccc tgagagagtt gcagcaagcg gtccacgctg | 6900 | |
| gtttgcccca gcaggcgaaa atcctgtttg atggtggttg acggcgggat ataacatgag | 6960 | |
| ctgtcttcgg tatcgtcgta tcccactacc gagatatccg caccaacgcg cagcccggac | 7020 | |
| tcggtaatgg cgcgcattgc gcccagcgcc atctgatcgt tggcaaccag catcgcagtg | 7080 | |
| ggaacgatgc cctcattcag catttgcatg gtttgttgaa aaccggacat ggcactccag | 7140 | |
| tcgccttccc gttccgctat cggctgaatt tgattgcgag tgagatattt atgccagcca | 7200 | |
| gccagacgca gacgcgccga gacagaactt aatgggcccg ctaacagcgc gatttgctgg | 7260 | |
| tgacccaatg cgaccagatg ctccacgccc agtcgcgtac cgtcttcatg ggagaaaata | 7320 | |
| atactgttga tgggtgtctg gtcagagaca tcaagaaata acgccggaac attagtgcag | 7380 | |
| gcagcttcca cagcaatggc atcctggtca tccagcggat agttaatgat cagcccactg | 7440 | |
| acgcgttgcg cgagaagatt gtgcaccgcc gctttacagg cttcgacgcc gcttcgttct | 7500 | |
| accatcgaca ccaccacgct ggcacccagt tgatcggcgc gagatttaat cgccgcgaca | 7560 | |
| atttgcgacg cgcgtgcag ggccagactg gaggtggcaa cgccaatcag caacgactgt | 7620 | |
| ttgcccgcca gttgttgtgc cacgcggttg ggaatgtaat tcagctccgc catcgccgct | 7680 | |
| tccactttt cccgcgtttt cgcagaaacg tggctgccct ggttcaccac gcgggaaacg | 7740 | |
| gtctgataag agacaccggc atactctgcg acatcgtata acgttactgg tttcacattc | 7800 | |
| accaccctga attgactctc ttccgggcgc tatcatgcca taccgcgaaa ggttttgcac | 7860 | |
| cattcgatgg tgtcaacgta atgcatgcc gcttcgcctt cgcgcgcgaa ttggccgcca | 7920 | |
| tgccggcgat aatggcctgc ttctcgccga aacgtttggt ggcgggacca gtgacgaagg | 7980 | |
| cttgagcgag ggcgtgcaag attccgaata ccgcaagcga caggccgatc atcgtcgcgc | 8040 | |
| tccagcgaaa gcggtcctcg ccgaaaatga cccagagcgc tgccggcacc tgtcctacga | 8100 | |
| gttgcatgat aaagaagaca gtcataagtg cggcgacgat agtcatgccc cgcgcccacc | 8160 | |
| ggaaggagct gactgggttg aaggctctca agggcatcgg cggagcttat cgactgcacg | 8220 | |
| gtgcaccaat gcttctggcg tcaggcagcc atcggaagct gtggtatggc tgtgcaggtc | 8280 | |
| gtaaatcact gcataattcg tgtcgctcaa ggcgcactcc cgttctggat aatgttttt | 8340 | |
| gcgccgacat cataacggtt ctggcaaata ttctgaaatg agctgttgac aattaatcat | 8400 | |
| cggctcgtat aatgtgtgga attgtgagcg gataacaatt tcacacagga aacagaa | 8457 | |

<210> SEQ ID NO 46
<211> LENGTH: 22
<212> TYPE: DNA
<213> ORGANISM: Artificial Sequence
<220> FEATURE:
<223> OTHER INFORMATION: Synthetic Construct - linker mtka mtkb

<400> SEQUENCE: 46
cgaacggggg aggaatcacg cc                                            22

<210> SEQ ID NO 47
<211> LENGTH: 7422
<212> TYPE: DNA
<213> ORGANISM: Artificial Sequence
<220> FEATURE:
<223> OTHER INFORMATION: Synthetic Construct - pET28-MEX-MTKAB

<400> SEQUENCE: 47

```
aattcgagct ccgtcgacaa gcttgcggcc gcactcgagc accaccacca ccaccactga    60
gatccggctg ctaacaaagc ccgaaaggaa gctgagttgg ctgctgccac cgctgagcaa   120
taactagcat aacccctt gg ggcctctaaa cgggtcttga ggggttttt t gctgaaagga   180 ggaactatat ccggattggc gaatgggacg cgccctgtag cggcgcatta agcgcggcgg   240
gtgtggtggt tacgcgcagc gtgaccgcta cacttgccag cgccctagcg cccgctcctt   300
tcgctttctt cccttccttt ctcgccacgt tcgccggctt tccccgtcaa gctctaaatc   360 ggggctccc tttagggttc cgatttagtg ctttacggca cctcgacccc aaaaaacttg   420
attagggtga tggttcacgt agtgggccat cgccctgata cacggttttt cgccctttga   480
cgttggagtc cacgttcttt aatagtggac tcttgttcca aactggaaca acactcaacc   540
ctatctcggt ctattctttt gatttataag gattttgcc gatttcggcc tattggttaa   600
aaaatgagct gatttaacaa aaatttaacg cgaattttaa caaaatatta acgtttacaa   660
tttcaggtgg cactttt cgg ggaaatgtgc gcggaaccc c tatttgttta tttttctaaa   720
tacattcaaa tatgtatccg ctcatgaatt aattcttaga aaaactcatc gagcatcaaa   780
tgaaactgca atttattcat atcaggatta tcaataccat attttt gaaa aagccgtttc   840 tgtaatgaag gagaaaactc accgaggcag ttccatagga tggcaagatc ctggtatcgg   900
tctgcgattc cgactcgtcc aacatcaata caacctatta atttccctc gtcaaaata   960 aggttatcaa gtgagaaatc accatgagtg acgactgaat ccggtgagaa tggcaaaagt  1020
ttatgcattt ctttccagac ttgttcaaca ggccagccat tacgctcgtc atcaaaatca  1080
ctcgcatcaa ccaaaccgtt attcattcgt gattgcgcct gagcgagacg aaatacgcga  1140
tcgctgttaa aaggacaatt acaaacagga atcgaatgca accggcgcag gaacactgcc  1200
agcgcatcaa caatattttc acctgaatca ggatattctt ctaatacctg gaatgctgtt  1260 ttccccgggga tcgcagtggt gagtaaccat gcatcatcag gagtacggat aaaatgcttg  1320
atggtcggaa gaggcataaa ttccgtcagc cagtttagtc tgaccatctc atctgtaaca  1380
tcattggcaa cgctacct tt gccatgtt tc agaaacaact ctggcgcatc gggcttccca  1440
tacaatcgat agattgtcgc acctgattgc ccgacattat cgcgagccca tttataccca  1500
tataaatcag catccatgtt ggaatttaat cgcggcctag agcaagacgt ttcccgttga  1560
atatggctca taacacccct tgtattactg tttatgtaag cagacagttt tattgttcat  1620
gaccaaaatc ccttaacgtg agttttcgtt ccactgagcg tcagacccc g tagaaaagat  1680 caaaggatct tcttgagatc cttttttt ct gcgcgtaatc tgctgcttgc aaacaaaaaa  1740
accaccgcta ccagcggtgg tttgtttgcc ggatcaagag ctaccaactc tttttccgaa  1800
ggtaactggc ttcagcagag cgcagatacc aaatactgtc cttctagtgt agccgtagtt  1860
aggccaccac ttcaagaact ctgtagcacc gcctacatac ctcgctctgc taatcctgtt  1920
accagtggct gctgccagtg gcgataagtc gtgtcttacc gggttggact caagacgata  1980
gttaccggat aaggcgcagc ggtcgggctg aacggggggt tcgtgcacac agcccagctt  2040
ggagcgaacg acctacaccg aactgagata cctacagcgt gagctatgag aaagcgccac  2100
gcttcccgaa gggagaaagg cggacaggta tccggtaagc ggcagggtcg gaacaggaga  2160
gcgcacgagg gagcttccag ggggaaacgc ctggtatctt tatagtcctg tcgggtttcg  2220
ccacctctga cttgagcgtc gatttttgtg atgctcgtca gggggggcgga gcctatggaa  2280 aaacgccagc aacgcggcct ttttacggtt cctggccttt tgctggcctt ttgctcacat  2340
```

```
gttctttcct gcgttatccc ctgattctgt ggataaccgt attaccgcct ttgagtgagc    2400
tgataccgct cgccgcagcc gaacgaccga gcgcagcgag tcagtgagcg aggaagcgga    2460
agagcgcctg atgcggtatt ttctccttac gcatctgtgc ggtatttcac accgcatata    2520
tggtgcactc tcagtacaat ctgctctgat gccgcatagt taagccagta tacactccgc    2580
tatcgctacg tgactgggtc atggctgcgc cccgacaccc gccaacaccc gctgacgcgc    2640
cctgacgggc ttgtctgctc ccggcatccg cttacagaca agctgtgacc gtctccggga    2700
gctgcatgtg tcagaggttt tcaccgtcat caccgaaacg cgcgaggcag ctgcggtaaa    2760
gctcatcagc gtggtcgtga agcgattcac agatgtctgc ctgttcatcc gcgtccagct    2820
cgttgagttt ctccagaagc gttaatgtct ggcttctgat aaagcgggcc atgttaaggg    2880
cggtttttc  ctgtttggtc actgatgcct ccgtgtaagg gggatttctg ttcatggggg    2940
taatgatacc gatgaaacga gagaggatgc tcacgatacg ggttactgat gatgaacatg    3000
cccggttact ggaacgttgt gagggtaaac aactggcggt atggatgcgg cgggaccaga    3060
gaaaaatcac tcagggtcaa tgccagcgct tcgttaatac agatgtaggt gttccacagg    3120
gtagccagca gcatcctgcg atgcagatcc ggaacataat ggtgcagggc gctgacttcc    3180
gcgtttccag actttacgaa acacggaaac cgaagaccat tcatgttgtt gctcaggtcg    3240
cagacgtttt gcagcagcag tcgcttcacg ttcgctcgcg tatcggtgat tcattctgct    3300
aaccagtaag gcaaccccgc cagcctagcc gggtcctcaa cgacaggagc acgatcatgc    3360
gcacccgtgg ggccgccatg ccggcgataa tggcctgctt ctcgccgaaa cgtttggtgg    3420
cgggaccagt gacgaaggct tgagcgaggg cgtgcaagat tccgaatacc gcaagcgaca    3480
ggccgatcat cgtcgcgctc cagcgaaagc ggtcctcgcc gaaaatgacc cagagcgctg    3540
ccggcacctg tcctacgagt tgcatgataa agaagacagt cataagtgcg gcgacgatag    3600
tcatgccccg cgcccaccgg aaggagctga ctgggttgaa ggctctcaag gcatcggtc     3660
gagatcccgt gcctaatga  gtgagctaac ttacattaat tgcgttgcgc tcactgcccg    3720
ctttccagtc gggaaacctg tcgtgccagc tgcattaatg aatcggccaa cgcgcgggga    3780
gaggcggttt gcgtattggg cgccagggtg gttttctttt tcaccagtga cgggcaac     3840
agctgattgc ccttcaccgc ctggccctga gagagttgca gcaagcggtc cacgctggtt    3900
tgccccagca ggcgaaaatc ctgtttgatg gtggttaacg gcgggatata acatgagctg    3960
tcttcggtat cgtcgtatcc cactaccgag atatccgcac caacgcgcag cccggactcg    4020
gtaatggcgc gcattgcgcc cagcgccatc tgatcgttgg caaccagcat cgcagtggga    4080
acgatgccct cattcagcat ttgcatggtt tgttgaaaac cggacatggc actccagtcg    4140
ccttcccgtt ccgctatcgg ctgaatttga ttgcgagtga gatatttatg ccagccagcc    4200
agacgcagac gcgccgagac agaacttaat gggcccgcta acagcgcgat ttgctggtga    4260
cccaatgcga ccagatgctc cacgcccagt cgcgtaccgt cttcatggga gaaaataata    4320
ctgttgatgg gtgtctggtc agagacatca agaaataacg ccggaacatt agtgcaggca    4380
gcttccacag caatggcatc ctggtcatcc agcggatagt taatgatcag cccactgacg    4440
cgttgcgcga agattgtg   caccgccgct ttacaggctt cgacgccgct tcgttctacc    4500
atcgacacca ccacgctggc acccagttga tcggcgcgag atttaatcgc cgcgacaatt    4560
tgcgacggcg cgtgcagggc cagactggag gtggcaacgc caatcagcaa cgactgtttg    4620
cccgccagtt gttgtgccac gcggttggga atgtaattca gctccgccat cgccgcttcc    4680
acttttttccc gcgttttcgc agaaacgtgg ctggcctggt tcaccacgcg ggaaacggtc    4740
```

-continued

```
tgataagaga caccggcata ctctgcgaca tcgtataacg ttactggttt cacattcacc    4800
accctgaatt gactctcttc cgggcgctat catgccatac cgcgaaaggt tttgcgccat    4860
tcgatggtgt ccgggatctc gacgctctcc cttatgcgac tcctgcatta ggaagcagcc    4920
cagtagtagg ttgaggccgt tgagcaccgc cgccgcaagg aatggtgcat gcaaggagat    4980
ggcgcccaac agtccccgg ccacggggcc tgccaccata cccacgccga acaagcgct     5040 catgagcccg aagtggcgag cccgatcttc cccatcggtg atgtcggcga tataggcgcc    5100
agcaaccgca cctgtggcgc cggtgatgcc ggccacgatg cgtccggcgt agaggatcga    5160
gatctcgatc ccgcgaaatt aatacgactc actataggg aattgtgagc ggataacaat    5220
tcccctctag aaataatttt gtttaacttt aagaaggaga tataccatgg gcagcagcca    5280
tcatcatcat catcacagca gcggcctggt gccgcgcggc agccatatgg ctagcatgga    5340
tgtgcacgaa tatcaggcga aagaactgct tgcgtcgttt ggagtcgccg tgcctaaggg    5400
cgccgtggcg ttttcaccgg atcaggcggt ctatgcagcc actgagttag gcggcagctt    5460
ttgggctgtc aaagcgcaga ttcatgccgg tgcacgcggc aaagcgggtg gtattaagtt    5520
gtgccgcacc tacaacgaag ttcgtgatgc tgcccgtgat ctcctgggta acggctggt     5580 aaccttgcaa accggtccgg agggtaaacc agtccagcgg gtatatgtgg aaacggctga    5640
tccgttcgaa cgcgaactct acttaggcta tgtgctggat cgcaaagcgg aacgtgtgcg    5700
cgttattgcc tcccaacgtg gcggcatgga tatcgaagag attgcggcta agaaccgga    5760 agcgcttatc caggtggtgg ttgaaccagc agtcggcttg cagcagttcc aagcccgcga    5820
gattgccttt cagctggggc tgaacatcaa acaggttagt gcagcggtta aaaccatcat    5880
gaacgcatat cgcgcattcc gcgattgtga cgggaccatg ctggagatta accccttagt    5940
agtgaccaaa gacgatcgcg tactggcact ggacgcgaaa atgagctttg acgacaatgc    6000
gctctttcgc cgtcgtaaca ttgcggatat gcatgacccg agtcaaggcg atccgcgtga    6060
agcgcaagct gccgagcaca acctgagcta cattggcctg gaaggcgaaa ttgggtgcat    6120
tgtgaatgga gctggtctgg caatggccac gatggacatg atcaaacatg cgggagggga    6180
accggccaat ttcctcgatg taggtggtgg tgcatctcct gatcgcgttg cgactgcctt    6240
ccgtctggtt ctgtccgatc gcaatgtgaa agctattctg gtcaacatct ttgcgggtat    6300
taatcgctgc gattgggtcg cagaagggg ggtcaaagca gctcgtgagg tgaagatcga    6360 cgttccctg atcgtacgtc ttgctggcac gaatgtggac gaaggcaaga aaattctggc    6420
cgaatcgggc ttagacttga tcacagccga tacgctgaca gaagcggccc gcaaagcggt    6480
tgaggcatgt catggagcga agcactaacg aacggggag gaatcacgcc atgtcgatcc    6540
tgattgacga aaagacgcca attctggtgc aaggcattac cggcgataaa gggacgtttc    6600
acgctaagga aatgattgcc tatggcagca atgtggtggg tggagttacc ccaggaaaag    6660
gtgggaaaac tcattgcggc gttcccgtgt caacaccgt gaaagaagct gtggaagcga    6720
ctggcgcgac cacctccatt accttcgtag cgccgccttt tgcagcggat gccattatgg    6780
aagccgctga tgccggctta aaactggtct gctccatcac agacggcatt cctgcgcagg    6840
acatgatgcg cgtcaaacgc tacttgcgtc gttatccgaa ggaaaagcgc acgatggtgg    6900
taggcccgaa ttgtgcgggt atcatctcgc cgggcaaaag catgctgggt attatgccgg    6960
ggcacatcta ccttcccggc aaagtcgtg tcattagtcg ctcagggacc cttgggtacg    7020
aagcggctgc gcagatgaaa gaactgggga ttggcatctc gacatccgtc ggaatcggtg    7080
```

-continued

```
gcgatccgat taacggtagc agctttctgg atcatctggc cctgttcgag caagatccgg    7140
aaaccgaagc cgttctcatg attggcgaaa ttggtggtcc acaggaggca gaagcaagcg    7200
catggatcaa agagaacttc tcaaaaccgg ttatcggttt tgtagccgga ttgactgctc    7260
cgaaaggtcg tcgcatgggt catgcaggcg cgatcatcag tgcgacgggt gactctgccg    7320
ctgagaaagc ggagattatg cggtcttatg gcctcacagt tgcacctgat ccgggtagtt    7380
ttggctctac ggttgccgat gtgttagcac gtgcggcgta ag                      7422
```

<210> SEQ ID NO 48
<211> LENGTH: 60
<212> TYPE: DNA
<213> ORGANISM: Artificial Sequence
<220> FEATURE:
<223> OTHER INFORMATION: Synthetic Construct - Primer for amplification

<400> SEQUENCE: 48

```
caggaaacag aattcgagct cggtaatgga tgtgcacgaa tatcaggcga aagaactgct    60
```

<210> SEQ ID NO 49
<211> LENGTH: 48
<212> TYPE: DNA
<213> ORGANISM: Artificial Sequence
<220> FEATURE:
<223> OTHER INFORMATION: Synthetic Construct - Primer for amplification

<400> SEQUENCE: 49

```
tacggcgcat cagaatcatt acgccgcacg tgctaacaca tcggcaac                 48
```

<210> SEQ ID NO 50
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 50

```
ggcgtaatga ttctgatgcg ccgtaccctg aaagcg                              36
```

<210> SEQ ID NO 51
<211> LENGTH: 42
<212> TYPE: DNA
<213> ORGANISM: Artificial Sequence
<220> FEATURE:
<223> OTHER INFORMATION: Synthetic Construct - Primer for amplification

<400> SEQUENCE: 51

```
ctgctgcttt cattacttct cgatgtagcc tttctccacg ag                       42
```

<210> SEQ ID NO 52
<211> LENGTH: 48
<212> TYPE: DNA
<213> ORGANISM: Artificial Sequence
<220> FEATURE:
<223> OTHER INFORMATION: Synthetic Construct - Primer for amplification

<400> SEQUENCE: 52

```
tacatcgaga agtaatgaaa gcagcagttc tgcataccta taaagaac                 48
```

<210> SEQ ID NO 53
<211> LENGTH: 57
<212> TYPE: DNA
<213> ORGANISM: Artificial Sequence
<220> FEATURE:
<223> OTHER INFORMATION: Synthetic Construct - Primer for amplification

<400> SEQUENCE: 53
cctgcaggtc gactctagag gatccttacg gaataatcag gctacgaatt gcttcac        57

<210> SEQ ID NO 54
<211> LENGTH: 9515
<212> TYPE: DNA
<213> ORGANISM: Artificial Sequence
<220> FEATURE:
<223> OTHER INFORMATION: Synthetic Construct - pETT20-MCS-DHB

<400> SEQUENCE: 54

```
ttcgagctcg gtaatggatg tgcacgaata tcaggcgaaa gaactgcttg cgtcgtttgg     60
agtcgccgtg cctaagggcg ccgtggcgtt ttcaccggat caggcggtct atgcagccac    120
tgagttaggc ggcagctttt gggctgtcaa agcgcagatt catgccggtg cacgcggcaa    180
agcgggtggt attaagttgt gccgcaccta caacgaagtt cgtgatgctg cccgtgatct    240
cctgggtaaa cggctggtaa ccttgcaaac cggtccggag ggtaaaccag tccagcgggt    300
atatgtggaa acggctgatc cgttcgaacg cgaactctac ttaggctatg tgctggatcg    360
caaagcggaa cgtgtgcgcg ttattgcctc ccaacgtggc ggcatggata tcgaagagat    420
tgcggctaaa gaaccggaag cgcttatcca ggtggtggtt gaaccagcag tcggcttgca    480
gcagttccaa gcccgcgaga ttgcctttca gctggggctg aacatcaaac aggttagtgc    540
agcggttaaa accatcatga cgcatatcg cgcattccgc gattgtgacg ggaccatgct    600
ggagattaac cccttagtag tgaccaaaga cgatcgcgta ctggcactgg acgcgaaaat    660
gagctttgac gacaatgcgc tctttcgccg tcgtaacatt gcggatatgc atgacccgag    720
tcaaggcgat ccgcgtgaag cgcaagctgc cgagcacaac ctgagctaca ttggcctgga    780
aggcgaaatt gggtgcattg tgaatggagc tggtctggca atggccacga tggacatgat    840
caaacatgcg ggaggggaac cggccaattt cctcgatgta ggtggtggtg catctcctga    900
tcgcgttgcg actgccttcc gtctggttct gtccgatcgc aatgtgaaag ctattctggt    960
caacatcttt gcgggtatta atcgctgcga ttgggtcgca gaaggggtgg tcaaagcagc   1020
tcgtgaggtg aagatcgacg ttcccctgat cgtacgtctt gctggcacga atgtggacga   1080
aggcaagaaa attctggccg aatcgggctt agacttgatc acagccgata cgctgacaga   1140
agcggcccgc aaagcggttg aggcatgtca tggagcgaag cactaacgaa cggggaggga   1200
atcacgccat gtcgatcctg attgacgaaa agacgccaat tctggtgcaa ggcattaccg   1260
gcgataaagg gacgtttcac gctaaggaaa tgattgccta tggcagcaat gtggtgggtg   1320
gagttacccc aggaaaaggt gggaaaactc attgcggcgt tcccgtgttc aacaccgtga   1380
aagaagctgt ggaagcgact ggcgcgacca cctccattac cttcgtagcg ccgccttttg   1440
cagcggatgc cattatggaa gccgctgatg ccggcttaaa actggtctgc tccatcacag   1500
acggcattcc tgcgcaggac atgatgcgcg tcaaacgcta cttgcgtcgt tatccgaagg   1560
aaaagcgcac gatggtggta ggcccgaatt gtgcgggtat catctcgccg ggcaaaagca   1620
tgctgggtat tatgccgggg cacatctacc ttcccggcaa agtcggtgtc attagtcgct   1680
cagggacccct tgggtacgaa gcggctgcgc agatgaaaga actggggatt ggcatctcga   1740
catccgtcgg aatcggtggc gatccgatta cggtagcag cttctggat catctggccc     1800
tgttcgagca agatccggaa accgaagccg ttctcatgat tggcgaaatt ggtggtccac   1860
aggaggcaga agcaagcgca tggatcaaag agaacttctc aaaaccggtt atcggttttg   1920
```

```
tagccggatt gactgctccg aaaggtcgtc gcatgggtca tgcaggcgcg atcatcagtg    1980
cgacgggtga ctctgccgct gagaaagcgg agattatgcg gtcttatggc ctcacagttg    2040
cacctgatcc gggtagtttt ggctctacgg ttgccgatgt gttagcacgt gcggcgtaat    2100
gattctgatg cgccgtaccc tgaaagcggc aatcttgggt gccaccggct tagtcgggat    2160
tgagtacgta cggatgctga gcaatcatcc gtacatcaaa cccgcctatc tggctgggaa    2220
agggtcagtt ggcaaaccgt atggcgaagt agtgcgctgg cagactgtgg gccaagttcc    2280
caaagaaatt gccgatatgg aaatcaagcc gactgatccg aaactgatgg atgatgttga    2340
catcatcttt agcccactgc ctcaaggtgc ggcaggaccc gttgaggaac aatttgcgaa    2400
agaaggattt ccggtcattt ccaattctcc ggatcatcgg tttgatccgg atgtcccact    2460
cctggtgcca gaactgaatc cgcacaccat tagccttatt gacgaacagc gtaaacgccg    2520
tgaatggaaa ggcttcatcg ttacgacgcc gttatgcacc gcacagggtg ctgcgatccc    2580
attgggtgcc atcttcaagg actacaaaat ggatggcgca ttcattacga ccattcagtc    2640
tcttagcggt gcgggatatc cgggtattcc gtccctggat gtggtggata acattctgcc    2700
tttaggggac ggttatgacg ccaaaacgat caaggaaatt ttccgcatcc tgagtgaagt    2760
gaaacgcaat gtggacgaac ctaaactgga ggacgtttca ctggccgcca aacccatcg    2820 cattgcaacc attcatggcc actatgaggt gttgtacgtg tcgtttaagg aagaaacagc    2880
agcggagaag gtcaaagaaa cgctggaaaa ctttcgcggt gaacctcagg atctcaaact    2940
gccgacagcg ccctcgaaac cgatcattgt gatgaacgaa gatactcgcc cacaggtata    3000
tttcgatcgt tgggcgggcg acattccggg catgagtgtc gttgttggcc gtctgaaaca    3060
ggtcaacaaa cgcatgattc gtctggtatc gcttatccac aacaccgtac gtggtgctgc    3120
gggcggtggg attttagctg cggagttgct cgtggagaaa ggctacatcg agaagtaatg    3180
aaagcagcag ttctgcatac ctataaagaa ccgctgagca ttgaagatgt gaatatttca    3240
cagccgaaag ccggtgaagt gaaaatcaaa gttaaagcaa ccggtctgtg tcgtagtgat    3300
gttcatgttt ttgaaggtaa acaccggttt ccgcctccgg ttgttgcagg tcatgaaatt    3360
agcggtattg ttgaagaggt tggtccgggt gttacccgtg ttaaaccggg tgatcgtgtt    3420
attagcgcat ttattcatcc gtgtggtaaa tgcggtaatt gtgttgccgg taaagaaaat    3480
ctgtgtgaaa cctttagcca ggttcgtctg aaaggtgtta tgccggatgg caccagccgt    3540
ctgagcaaag atggcaaaga aattcgtacc tttctgggtg gtggttttgc agaatatgca    3600
attgttggtg aaaatgcact gacccgtgtt ccggaagata tggatctgga aaaagttgca    3660
gttctgggtt gtgccggtct gaccggttat ggtgcaatta gcagcagcaa aattgaacct    3720
ggtgataccg ttgcagttat tggtgttggt ggtgtgggtc tgagcaccat tcagctgctg    3780
cgtgcaagcg gtgcaggtcg tattattgca gttggcacca aaaaatggaa actggatcgt    3840
gcaatggaac tgggtgcaac cgatgttgtt aacagtaaag aaattgatcc ggtgaaagcc    3900
atcaaagaaa tcaccggtgg tggtccgcag gttgttattg aagccggtgg taatgaagat    3960
accattcaca tggcactgga tagcgttcgt attggtggta agttgttct ggttggtctg    4020 cctccggcaa ccgcaatgat tccgattcgt gttgcaagca ttgttcgtgg tggtattgaa    4080
gttgttggta attatggtgg tcgtccgcgt gttgatatgc cgaaactgct ggaactggtt    4140
cgtcagggtc gttatgatcc gagccgtctg gttaccggtc gttttcgtct ggaagaaatt    4200
aatgaagccg tcaaaatgct ggaagaaggt gaagcaattc gtagcctgat tattccgtaa    4260
ggatcctcta gagtcgacct gcaggcatgc aagcttctgt tttggcggat gagagaagaa    4320
```

```
attcgtcgcc cgccataaac tgccaggcat caaattaagc agaaggccat cctgacggat    4380 ggccttttg  cgtttctaca aactcttcct gtctagcagg tggcacttt  cggggaaatg    4440 tgcgcggaac ccctatttgt ttattttct  aaatacattc aaatatgtat ccgctcatgc    4500
tagaaatatt ttatctgatt aataagatga tcttcttgag atcgttttgg tctgcgcgta    4560
atctcttgct ctgaaaacga aaaaaccgcc ttgcagggcg ttttttcgaa ggttctctga    4620
gctaccaact ctttgaaccg aggtaactgg cttggaggag cgcagtcacc aaaacttgtc    4680
ctttcagttt agccttaacc ggcgcatgac ttcaagacta actcctctaa atcaattacc    4740
agtggctgct gccagtggtg cttttgcatg tctttccggg ttggactcaa gacgatagtt    4800
accggataag gcgcagcggt cggactgaac gggggggttcg tgcatacagt ccagcttgga    4860
gcgaactgcc tacccggaac tgagtgtcag gcgtggaatg agacaaacgc ggccataaca    4920
gcggaatgac accggtaaac cgaaaggcag gaacaggaga gcgcacgagg gagccgccag    4980
gggaaacgcc tggtatcttt atagtcctgt cgggtttcgc caccactgat ttgagcgtca    5040
gatttcgtga tgcttgtcag gggggcggag cctatggaaa aacggctttg ccgcggccct    5100
ctcacttccc tgttaagtat cttcctggca tcttccagga aatctccgcc ccgttcgtaa    5160
gccatttccg ctcgccgcag tcgaacgacc gagcgtagcg agtcagtgag cgaggaagcg    5220
gaatatatcc tgtatcacat attctgctga cgcaccggtg cagcctttt  tctcctgcca    5280 catgaagcac ttcactgaca ccctcatcag tgccaacata gtaagccagt atacactccg    5340
ctagcgctga tgtccggcgg tgcttttgcc gttacgcacc accccgtcag tagctgaaca    5400
ggagggacag ctgatagaaa cagaagccac tggagcacct caaaaacacc atcatacact    5460
aaatcagtaa gttggcagca tcacccgacg cactttgcgc cgaataaata cctgtgacgg    5520
aagatcactt cgcagaataa ataaatcctg gtgtccctgt tgataccggg aagccctggg    5580
ccaacttttg gcgaaaatga gacgttgatc ggcacgtaag aggttccaac tttcaccata    5640
atgaaataag atcactaccg ggcgtatttt ttgagttatc gagattttca ggagctaagg    5700
aagctaaaat ggagaaaaaa atcactggat ataccaccgt tgatatatcc caatggcatc    5760
gtaaagaaca ttttgaggca tttcagtcag ttgctcaatg tacctataac cagaccgttc    5820
agctggatat tacggccttt ttaaagaccg taaagaaaaa taagcacaag ttttatccgg    5880
cctttattca cattcttgcc cgcctgatga atgctcatcc ggaattccgt atggcaatga    5940
aagacggtga gctggtgata tgggatagtg ttcacccttg ttacaccgtt ttccatgagc    6000
aaactgaaac gttttcatcg ctctggagtg aataccacga cgatttccgg cagtttctac    6060
acatatattc gcaagatgtg gcgtgttacg gtgaaaacct ggcctatttc cctaaagggt    6120
ttattgagaa tatgtttttc gtctcagcca atccctgggt gagtttcacc agttttgatt    6180
taaacgtggc caatatggac aacttcttcg cccccgtttt caccatgggc aaatattata    6240
cgcaaggcga caaggtgctg atgccgctgg cgattcaggt tcatcatgcc gtctgtgatg    6300
gcttccatgt cggcagaatg cttaatgaat tacaacagta ctgcgatgag tggcagggcg    6360
gggcgtaatt ttttaaggc  agttattggt gcccttaaac gcctggtgct acgcctgaat    6420
aagtgataat aagcggatga atggcagaaa ttcgaaagca aattcgaccc ggtcgtcggt    6480
tcagggcagg gtcgttaaat agccgcttat gtctattgct ggtttaccgg tttattgact    6540
accggaagca gtgtgaccgt gtgcttctca aatgcctgag gccagtttgc tcaggctctc    6600
cccgtggagg taataattga cgatatgatc atttattctg cctcccagag cctgataaaa    6660
```

```
acggttagcg cttcgttaat acagatgtag gtgttccaca gggtagccag cagcatcctg   6720
cgatgcagat ccggaacata atggtgcagg gcgcttgttt cggcgtgggt atggtggcag   6780
gccccgtggc cggggggactg ttgggcgctg ccggcacctg tcctacgagt tgcatgataa   6840
agaagacagt cataagtgcg gcgacgatag tcatgccccg cgcccaccgg aaggagctac   6900
cggacagcgg tgcggactgt tgtaactcag aataagaaat gaggccgctc atggcgttga   6960
ctctcagtca tagtatcgtg gtatcaccgg ttggttccac tctctgttgc gggcaacttc   7020
agcagcacgt aggggacttc cgcgtttcca gactttacga aacacggaaa ccgaagacca   7080
ttcatgttgt tgctcaggtc gcagacgttt tgcagcagca gtcgcttcac gttcgctcgc   7140
gtatcggtga ttcattctgc taaccagtaa ggcaaccccg ccagcctagc cgggtcctca   7200
acgacaggag cacgtcatg cgcacccgtg gccaggaccc aacgctgccc gagatgcgcc   7260
gcgtgcggct gctggagatg gcggacgcga tggatatgtt ctgccaaggg ttggtttgcg   7320
cattcacagt tctccgcaag aattgattgg ctccaattct tggagtggtg aatccgttag   7380
cgaggtgccg ccggcttcca ttcaggtcga ggtggcccgg ctccatgcac cgcgacgcaa   7440
cgcggggagg cagacaaggt atagggcggc gcctacaatc catgccaacc cgttccatgt   7500
gctcgccgag gcgcataaa tcgccgtgac gatcagcggt ccagtgatcg aagttaggct   7560
ggtaagagcc gcgagcgatc cttgaagctg tccctgatgg tcgtcatcta cctgcctgga   7620
cagcatggcc tgcaacgcgg gcatcccgat gccgccggaa gcgagaagaa tcataatggg   7680
gaaggccatc cagcctcgcg tcgcgaacgc cagcaagacg tagcccagcg cgtcggccaa   7740
ttcgcgctaa cttacattaa ttgcgttgcg ctcactgccc gctttccagt cgggaaacct   7800
gtcgtgccag ctgcattaat gaatcggcca acgcgcgggg agaggcggtt gcgtattgg   7860
gcgccagggt ggttttctct ttcaccagtg agacgggcaa cagctgattg cccttcaccg   7920
cctggccctg agagagttgc agcaagcggt ccacgctggt ttgccccagc aggcgaaaat   7980
cctgtttgat ggtggttgac ggcgggatat aacatgagct gtcttcggta tcgtcgtatc   8040
ccactaccga gatatccgca ccaacgcgca gcccggactc ggtaatggcg cgcattgcgc   8100
ccagcgccat ctgatcgttg gcaaccagca tcgcagtggg aacgatgccc tcattcagca   8160
tttgcatggt ttgttgaaaa ccggacatgg cactccagtc gccttcccgt tccgctatcg   8220
gctgaatttg attgcgagtg agatatttat gccagccagc cagacgcaga gcgcgccgaga   8280
cagaacttaa tgggcccgct aacagcgcga tttgctggtg acccaatgcg accagatgct   8340
ccacgcccag tcgcgtaccg tcttcatggg agaaaataat actgttgatg ggtgtctggt   8400
cagagacatc aagaaataac gccggaacat tagtgcaggc agcttccaca gcaatggcat   8460
cctggtcatc cagcggatag ttaatgatca gcccactgac gcgttgcgcg agaagattgt   8520
gcaccgccgc tttacaggct tcgacgccgc ttcgttctac catcgacacc accacgctgg   8580
cacccagttg atcggcgcga gatttaatcg ccgcgacaat ttgcgacggc gcgtgcaggg   8640
ccagactgga ggtggcaacg ccaatcagca acgactgttt gcccgccagt tgttgtgcca   8700
cgcggttggg aatgtaattc agctccgcca tcgccgcttc cacttttttcc cgcgttttcg   8760
cagaaacgtg gctggcctgg ttcaccacgc gggaaacggt ctgataagag acaccggcat   8820
actctgcgac atcgtataac gttactggtt tcacattcac caccctgaat tgactctctt   8880
ccgggcgcta tcatgccata ccgcgaaagg ttttgcacca ttcgatggtg tcaacgtaaa   8940
tgcatgccgc ttcgccttcg cgcgcgaatt ggccgccatg ccggcgataa tggcctgctt   9000
ctcgccgaaa cgtttggtgg cgggaccagt gacgaaggct tgagcgaggg cgtgcaagat   9060
```

```
tccgaatacc gcaagcgaca ggccgatcat cgtcgcgctc cagcgaaagc ggtcctcgcc    9120
gaaaatgacc cagagcgctg ccggcacctg tcctacgagt tgcatgataa agaagacagt    9180
cataagtgcg gcgacgatag tcatgccccg cgcccaccgg aaggagctga ctgggttgaa    9240
ggctctcaag ggcatcggcg gagcttatcg actgcacggt gcaccaatgc ttctggcgtc    9300
aggcagccat cggaagctgt ggtatggctg tgcaggtcgt aaatcactgc ataattcgtg    9360
tcgctcaagg cgcactcccg ttctggataa tgtttttttgc gccgacatca taacggttct    9420
ggcaaatatt ctgaaatgag ctgttgacaa ttaatcatcg gctcgtataa tgtgtggaat    9480
tgtgagcgga taacaatttc acacaggaaa cagaa                               9515
```

<210> SEQ ID NO 55
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 55

```
tataatcccg ggatgcgcgt taacaatggt ttgacc                              36
```

<210> SEQ ID NO 56
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 56

```
tataattcta gattacagtt tcggaccagc cg                                  32
```

<210> SEQ ID NO 57
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 57

```
tataatcccg ggatgcgcgt taacaatggt ttgacc                              36
```

<210> SEQ ID NO 58
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 58

```
tataattcta gattacagtt tcggaccagc cg                                  32
```

<210> SEQ ID NO 59
<211> LENGTH: 30
<212> TYPE: DNA
<213> ORGANISM: Artificial Sequence
<220> FEATURE:
<223> OTHER INFORMATION: Synthetic Construct - Primer for amplification

<400> SEQUENCE: 59

```
tataatcccg ggatgaacga acaatattcc                                     30
```

<210> SEQ ID NO 60

```
<211> LENGTH: 30
<212> TYPE: DNA
<213> ORGANISM: Artificial Sequence
<220> FEATURE:
<223> OTHER INFORMATION: Synthetic Construct - Primer for amplification

<400> SEQUENCE: 60
tataattcta gattagccgg tattacgcat                                      30

<210> SEQ ID NO 61
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 61
tataatcccg ggatgtccag aaggcttcgc agaaca                               36

<210> SEQ ID NO 62
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 62
tataattcta gattactcta ccgttaaaat ac                                   32

<210> SEQ ID NO 63
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 63
tataatcccg ggatgaaaac ccgtacacaa caaatt                               36

<210> SEQ ID NO 64
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 64
tataattcta gattagaact gcgattcttc ag                                   32

<210> SEQ ID NO 65
<211> LENGTH: 36
<212> TYPE: DNA
<213> ORGANISM: Artificial Sequence
<220> FEATURE:
<223> OTHER INFORMATION: Synthetic Construct - Primer for amplification

<400> SEQUENCE: 65
tataatcccg ggatgaaaaa actactcgtc gccaat                               36

<210> SEQ ID NO 66
<211> LENGTH: 32
<212> TYPE: DNA
<213> ORGANISM: Artificial Sequence
<220> FEATURE:
<223> OTHER INFORMATION: Synthetic Construct - Primer for amplification

<400> SEQUENCE: 66
```

```
tataattcta gattaattaa tttcgattaa ca                                  32

<210> SEQ ID NO 67
<211> LENGTH: 40
<212> TYPE: DNA
<213> ORGANISM: Artificial Sequence
<220> FEATURE:
<223> OTHER INFORMATION: Synthetic Construct - Primer for amplification

<400> SEQUENCE: 67
tataatcccg ggatgcctga cgctaaaaaa cagggcggt                           40

<210> SEQ ID NO 68
<211> LENGTH: 33
<212> TYPE: DNA
<213> ORGANISM: Artificial Sequence
<220> FEATURE:
<223> OTHER INFORMATION: Synthetic Construct - Primer for amplification

<400> SEQUENCE: 68
tataattcta gattaatcgt gagcgcctat ttc                                 33

<210> SEQ ID NO 69
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 69
gaaggttgcg cctacactaa gcatagttgt tgatgagtgt aggctggagc tgcttc        56

<210> SEQ ID NO 70
<211> LENGTH: 56
<212> TYPE: DNA
<213> ORGANISM: Artificial Sequence
<220> FEATURE:
<223> OTHER INFORMATION: Synthetic Construct - Primer for amplification

<400> SEQUENCE: 70
ttaaaccagt tcgttcgggc aggtttcgcc ttttcatgg gaattagcca tggtcc         56

<210> SEQ ID NO 71
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 71
atggctgtta ctaatgtcgc tgaacttaac gcactcgtag agcgtgtgta ggctggagct    60
gcttc                                                                65

<210> SEQ ID NO 72
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 72
ttaagcggat ttttcgctt ttttctcagc tttagccgga gcagccatat gaatatcctc    60
cttag                                                                65
```

<210> SEQ ID NO 73
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 73
atgtcgagta agttagtact ggttctgaac tgcggtagtt cttcagtgta ggctggagct    60
gcttc                                                                65

<210> SEQ ID NO 74
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 74
tcaggcagtc aggcggctcg cgtcttgcgc gataaccagt tcttccatat gaatatcctc    60
cttag                                                                65

<210> SEQ ID NO 75
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 75
ttactccgta tttgcataaa aaccatgcga gttacgggcc tataagtgta ggctggagct    60
gcttc                                                                65

<210> SEQ ID NO 76
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 76
atagattgag tgaaggtacg agtaataacg tcctgctgct gttctcatat gaatatcctc    60
cttag                                                                65

<210> SEQ ID NO 77
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 77
gtgtcccgta ttattatgct gatccctacc ggaaccagcg tcggtgtgta ggctggagct    60
gcttc                                                                65

<210> SEQ ID NO 78
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 78

```
ttactgctgc tgtgcagact gaatcgcagt cagcgcgatg gtgtacatat gaatatcctc    60
cttag                                                                65
```

<210> SEQ ID NO 79
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 79

```
atgaaacaaa cggttgcagc ttatatcgcc aaaacactcg aatcggtgta ggctggagct    60
gcttc                                                                65
```

<210> SEQ ID NO 80
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 80

```
ttaccttagc cagtttgttt tcgccagttc gatcacttca tcacccatat gaatatcctc    60
cttag                                                                65
```

<210> SEQ ID NO 81
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 81

```
atgaccatta ctccggcaac tcatgcaatt tcgataaatc ctgccgtgta ggctggagct    60
gcttc                                                                65
```

<210> SEQ ID NO 82
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 82

```
tcagatccgg tctttccaca ccgtctggat attacagaat tcgtgcatat gaatatcctc    60
cttag                                                                65
```

<210> SEQ ID NO 83
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 83

```
atgaaactta acgacagtaa cttattccgc cagcaggcgt tgattgtgta ggctggagct    60
gcttc                                                                65
```

<210> SEQ ID NO 84
<211> LENGTH: 65
<212> TYPE: DNA

```
<213> ORGANISM: Artificial Sequence
<220> FEATURE:
<223> OTHER INFORMATION: Synthetic Construct - Primer for amplification

<400> SEQUENCE: 84
ttaaagaccg atgcacatat atttgatttc taagtaatct tcgatcatat gaatatcctc    60
cttag                                                                65

<210> SEQ ID NO 85
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 85
atggaccaga agctgttaac ggatttccgc tcagaactac tcgatgtgta ggctggagct    60
gcttc                                                                65

<210> SEQ ID NO 86
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 86
tcaggtgtgt ttaaagctgt tctgctgggc aataccctgc agtttcatat gaatatcctc    60
cttag                                                                65

<210> SEQ ID NO 87
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 87
atggataaga agcaagtaac ggatttaagg tcggaactac tcgatgtgta ggctggagct    60
gcttc                                                                65

<210> SEQ ID NO 88
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 88
tcaggtatgt ttaaagctgt tctgttgggc aataccctgc agtttcatat gaatatcctc    60
cttag                                                                65

<210> SEQ ID NO 89
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 89
atggctacat cagtacagac aggtaaagct aagcagctca cattagtgta ggctggagct    60
gcttc                                                                65
```

<210> SEQ ID NO 90
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 90
ttagtgtttc ttgtcattca tcacaatata gtgtggtgaa cgtgccatat gaatatcctc    60
cttag                                                                65

<210> SEQ ID NO 91
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 91
atggaaccaa aaacaaaaaa acagcgttcg ctttatatcc cttacgtgta ggctggagct    60
gcttc                                                                65

<210> SEQ ID NO 92
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 92
ttagatggag gtacggcggt agtcgcggta ttcggcttgc cagaacatat gaatatcctc    60
cttag                                                                65

<210> SEQ ID NO 93
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 93
atggatgacc agttaaaaca aagtgcactt gatttccatg aatttgtgta ggctggagct    60
gcttc                                                                65

<210> SEQ ID NO 94
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 94
ttacagcggt tgggtttgcg cttctaccac ggccagcgcc accatcatat gaatatcctc    60
cttag                                                                65

<210> SEQ ID NO 95
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 95
atgaacgaac aatattccgc attgcgtagt aatgtcagta tgctcgtgta ggctggagct    60
gcttc    65

<210> SEQ ID NO 96
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 96
ttagccggta ttacgcatac ctgccgcaat cccggcaata gtgaccatat gaatatcctc    60
cttag    65

<210> SEQ ID NO 97
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 97
atgtccagaa ggcttcgcag aacaaaaatc gttaccacgt taggcgtgta ggctggagct    60
gcttc    65

<210> SEQ ID NO 98
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 98
ttactctacc gttaaaatac gcgtggtatt agtagaaccc acggtcatat gaatatcctc    60
cttag    65

<210> SEQ ID NO 99
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 99
atgaaaaaga ccaaaattgt ttgcaccatc ggaccgaaaa ccgaagtgta ggctggagct    60
gcttc    65

<210> SEQ ID NO 100
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 100
ttacaggacg tgaacagatg cggtgttagt agtgccgctc ggtaccatat gaatatcctc    60
cttag    65

<210> SEQ ID NO 101
<211> LENGTH: 65

<212> TYPE: DNA
<213> ORGANISM: Artificial Sequence
<220> FEATURE:
<223> OTHER INFORMATION: Synthetic Construct - Primer for amplification

<400> SEQUENCE: 101
atggaactga cgactcgcac tttacctgcg cggaaacata ttgcggtgta ggctggagct    60
gcttc    65

<210> SEQ ID NO 102
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 102
ttacttcaga cggtccgcga gataacgctg ataatcgggg atcagcatat gaatatcctc    60
cttag    65

<210> SEQ ID NO 103
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 103
atggtcgcac ccattcccgc gaaacgcggc agaaaacccg ccgttgtgta ggctggagct    60
gcttc    65

<210> SEQ ID NO 104
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 104
tcagcgcatt ccaccgtacg ccagcgtcac ttccttcgcc gctttcatat gaatatcctc    60
cttag    65

<210> SEQ ID NO 105
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 105
atggaaagta aagtagttgt tccggcacaa ggcaagaaga tcaccgtgta ggctggagct    60
gcttc    65

<210> SEQ ID NO 106
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 106
ttacatgttt tcgatgatcg cgtcaccaaa ctctgaacat ttcagcatat gaatatcctc    60

-continued cttag                                                              65

<210> SEQ ID NO 107
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 107
atgcagaaca gcgctttgaa agcctggttg gactcttctt acctcgtgta ggctggagct     60
gcttc                                                              65

<210> SEQ ID NO 108
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 108
ttattcgacg ttcagcgcgt cattaaccag atcttgttgc tgtttcatat gaatatcctc     60
cttag                                                              65

<210> SEQ ID NO 109
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 109
atgagtagcg tagatattct ggtccctgac ctgcctgaat ccgtagtgta ggctggagct     60
gcttc                                                              65

<210> SEQ ID NO 110
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 110
ctacacgtcc agcagcagac gcgtcggatc ttccagcaac tctttcatat gaatatcctc     60
cttag                                                              65

<210> SEQ ID NO 111
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 111
gtgcaaacct ttcaagccga tcttgccatt gtaggcgccg gtggcgtgta ggctggagct     60
gcttc                                                              65

<210> SEQ ID NO 112
<211> LENGTH: 65
<212> TYPE: DNA
<213> ORGANISM: Artificial Sequence
<220> FEATURE:
<223> OTHER INFORMATION: Synthetic Construct - Primer for amplification -continued

<400> SEQUENCE: 112
tcagccattc gccttctcct tcttattggc tgcttccgcc ttatccatat gaatatcctc    60
cttag    65

<210> SEQ ID NO 113
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 113
atggctgaga tgaaaaacct gaaaattgag gtggtgcgct ataacgtgta ggctggagct    60
gcttc    65

<210> SEQ ID NO 114
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 114
ttagcgtggt ttcagggtcg cgataagaaa gtctttcgaa ctttccatat gaatatcctc    60
cttag    65

<210> SEQ ID NO 115
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 115
atgacgacta aacgtaaacc gtatgtacgg ccaatgacgt ccaccgtgta ggctggagct    60
gcttc    65

<210> SEQ ID NO 116
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 116
ttaccagtac agggcaacaa acaggattac gatggtggca accaccatat gaatatcctc    60
cttag    65

<210> SEQ ID NO 117
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 117
atgattaatc caaatccaaa gcgttctgac gaaccggtat tctgggtgta ggctggagct    60
gcttc    65

<210> SEQ ID NO 118

```
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 118
ttagattgta acgacaccaa tcagcgtgac aactgtcagg atagccatat gaatatcctc      60
cttag                                                                 65

<210> SEQ ID NO 119
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 119
atgatttcag gcattttagc atccccgggt atcgctttcg gtaaagtgta ggctggagct      60
gcttc                                                                 65

<210> SEQ ID NO 120
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 120
ttagcagatt gttttttctt caatgaactt gttaaccagc gtcatcatat gaatatcctc      60
cttag                                                                 65

<210> SEQ ID NO 121
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 121
atgtttaaga atgcatttgc taacctgcaa aaggtcggta aatcggtgta ggctggagct      60
gcttc                                                                 65

<210> SEQ ID NO 122
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 122
ttagtggtta cggatgtact catccatctc ggttttcagg ttatccatat gaatatcctc      60
cttag                                                                 65

<210> SEQ ID NO 123
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 123
gtgaaaccag taacgttata cgatgtcgca gagtatgccg gtgtcgtgta ggctggagct      60
```

```
gcttc                                                              65

<210> SEQ ID NO 124
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 124
tcactgcccg ctttccagtc gggaaacctg tcgtgccagc tgcatcatat gaatatcctc    60
cttag                                                              65

<210> SEQ ID NO 125
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 125
atgattattt ccgcagccag cgattatcgc gccgcagcgc aacgcgtgta ggctggagct    60
gcttc                                                              65

<210> SEQ ID NO 126
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 126
ctatgccgca ttccctttcg ccatgggagc cagtgccgca ggcaacatat gaatatcctc    60
cttag                                                              65

<210> SEQ ID NO 127
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 127
atgaaaaaca tcaatccaac gcagaccgct gcctggcagg cactagtgta ggctggagct    60
gcttc                                                              65

<210> SEQ ID NO 128
<211> LENGTH: 65
<212> TYPE: DNA
<213> ORGANISM: Artificial Sequence
<220> FEATURE:
<223> OTHER INFORMATION: Synthetic Construct - Primer for amplification

<400> SEQUENCE: 128
ttaaccgcgc cacgctttat agcggttaat cagaccattg gtcgacatat gaatatcctc    60
cttag                                                              65

<210> SEQ ID NO 129
<211> LENGTH: 20
<212> TYPE: DNA
<213> ORGANISM: Artificial Sequence
<220> FEATURE:
```

<223> OTHER INFORMATION: Synthetic Construct - Primer for amplification

<400> SEQUENCE: 129
cggtgccctg aatgaactgc                                            20

<210> SEQ ID NO 130
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 130
cagtcatagc cgaatagcct                                            20

<210> SEQ ID NO 131
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 131
atacgtgtcc cgagcggtag                                            20

<210> SEQ ID NO 132
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 132
tacacatccc gccatcagca                                            20

<210> SEQ ID NO 133
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 133
gaagtaaacg ggaaaatcaa                                            20

<210> SEQ ID NO 134
<211> LENGTH: 20
<212> TYPE: DNA
<213> ORGANISM: Artificial Sequence
<220> FEATURE:
<223> OTHER INFORMATION: Synthetic Construct - Primer for amplificatio

<400> SEQUENCE: 134
agaagtggca taagaaaacg                                            20

<210> SEQ ID NO 135
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 135
ccattggctg aaaattacgc                                            20

```
<210> SEQ ID NO 136
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 136
gttccattgc acggatcacg                                                  20

<210> SEQ ID NO 137
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 137
atgccgtaga agccgccagt                                                  20

<210> SEQ ID NO 138
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 138
tgttggtgcg cagctcgaag                                                  20

<210> SEQ ID NO 139
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 139
gcaaatctgg tttcatcaac                                                  20

<210> SEQ ID NO 140
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 140
tcccttgcac aaaacaaagt                                                  20

<210> SEQ ID NO 141
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 141
ggatttggtt ctcgcataat                                                  20

<210> SEQ ID NO 142
<211> LENGTH: 20
<212> TYPE: DNA
<213> ORGANISM: Artificial Sequence
<220> FEATURE:
<223> OTHER INFORMATION: Synthetic Construct - Primer for amplification
```

```
<400> SEQUENCE: 142
agcattaacg gtagggtcgt                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 143
gctgattctc gcgaataaac                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 144
aaaaacgttc ttgcgcgtct                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 145
tctgtttgtc accacccgc                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 146
aagccagcac ctggaagcag                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 147
aagagctgcc gcaggaggat                                              20

<210> SEQ ID NO 148
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 148
gccgccctct taagtcaaat                                              20

<210> SEQ ID NO 149
<211> LENGTH: 20
```

```
<212> TYPE: DNA
<213> ORGANISM: Artificial Sequence
<220> FEATURE:
<223> OTHER INFORMATION: Synthetic Construct - Primer for amplification

<400> SEQUENCE: 149
ggattttagc aatattcgct                                              20

<210> SEQ ID NO 150
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 150
cctaatagca ggaagaagac                                              20

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 151
gctgaactgt tgctggaaga                                              20

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 152
ggcgtgcttt tacaactaca                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 153
tagtaaataa cccaaccggc                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 154
tcagtgagcg cagtgtttta                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 155
```

-continued

```
attaatggtg agagtttgga                                          20

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 156 tgctttttt tattattcgc                                           20

<210> SEQ ID NO 157
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 157
gctttataaa agacgacgaa                                          20

<210> SEQ ID NO 158
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 158
gtaacgacaa ttccttaagg                                          20

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 159
tttatatgcc catggtttct                                          20

<210> SEQ ID NO 160
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 160
atctgttaga ggcggatgat                                          20

<210> SEQ ID NO 161
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 161
ctggaacgtt aaatctttga                                          20

<210> SEQ ID NO 162
<211> LENGTH: 20
<212> TYPE: DNA
<213> ORGANISM: Artificial Sequence
```

```
<220> FEATURE:
<223> OTHER INFORMATION: Primer for amplification

<400> SEQUENCE: 162
ccagtttagt agctttcatt                                              20

<210> SEQ ID NO 163
<211> LENGTH: 25
<212> TYPE: DNA
<213> ORGANISM: Artificial Sequence
<220> FEATURE:
<223> OTHER INFORMATION: Synthetic Construct - Primer for amplification

<400> SEQUENCE: 163
gatttgttca acattaactc atcgg                                        25

<210> SEQ ID NO 164
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 164
tgcgattaac agacaccctt                                              20

<210> SEQ ID NO 165
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 165
tctcaggtgc tcacagaaca                                              20

<210> SEQ ID NO 166
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 166
tatggaagag gcgctactgc                                              20

<210> SEQ ID NO 167
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 167
cgacctgctg cataaacacc                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 168
tgaacgctaa ggtgattgca                                              20
```

<210> SEQ ID NO 169
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 169
acgtagacaa gagctcgcaa                                           20

<210> SEQ ID NO 170
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 170
catcacgtac gactgcgtcg                                           20

<210> SEQ ID NO 171
<211> LENGTH: 19
<212> TYPE: DNA
<213> ORGANISM: Artificial Sequence
<220> FEATURE:
<223> OTHER INFORMATION: Synthetic Construct - Primer for amplification

<400> SEQUENCE: 171
tgcaactttg tgctgagca                                            19

<210> SEQ ID NO 172
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 172
tatcgcttcc gggcattgtc                                           20

<210> SEQ ID NO 173
<211> LENGTH: 25
<212> TYPE: DNA
<213> ORGANISM: Artificial Sequence
<220> FEATURE:
<223> OTHER INFORMATION: Synthetic Construct - Primer for amplification

<400> SEQUENCE: 173
aaatcgatct cgtcaaattt cagac                                     25

<210> SEQ ID NO 174
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 174
aggaaccaca aatcgccata                                           20

<210> SEQ ID NO 175
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 175
gacgtgaaga ttactacgct                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 176
agttcaatgc tgaaccacac                                              20

<210> SEQ ID NO 177
<211> LENGTH: 25
<212> TYPE: DNA
<213> ORGANISM: Artificial Sequence
<220> FEATURE:
<223> OTHER INFORMATION: Synthetic Construct - Primer for amplification

<400> SEQUENCE: 177
tagccgcgac cacggtaaga aggag                                        25

<210> SEQ ID NO 178
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 178
cagcgcatca cccggaaaca                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 179
atcgtgatca ttaacctgat                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 180
ttaccctgat aaattaccgc                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 181
gaatctggtg tatatggcga                                              20

<210> SEQ ID NO 182

```
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 182
tcttcgctat tacgccagct                                                   20

<210> SEQ ID NO 183
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 183
cgtcagcgga tgtatctggt                                                   20

<210> SEQ ID NO 184
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 184
gcggaatttc tggttcgtaa                                                   20

<210> SEQ ID NO 185
<211> LENGTH: 387
<212> TYPE: PRT
<213> ORGANISM: Escherichia coli

<400> SEQUENCE: 185

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
```

```
                195                 200                 205
Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 186
<211> LENGTH: 1164
<212> TYPE: DNA
<213> ORGANISM: Escherichia coli

<400> SEQUENCE: 186
atgaacaact taatctgca  caccccaacc cgcattctgt tggtaaagg  cgcaatcgct      60 ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaaccccggct tatgaaacgc tgatgaacgc cgtgaaactg    240
gttcgcgaac agaaagtgac tttcctgctg gcggttggcg cgggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
```

```
acccacctct ccgactacgg tctggacggc agctccatcc cggctttgct gaaaaaactg    1080
gaagagcacg gcatgaccca actgggcgaa atcatgaca ttacgttgga tgtcagccgc    1140
cgtatatacg aagccgcccg ctaa                                           1164
```

<210> SEQ ID NO 187
<211> LENGTH: 371
<212> TYPE: PRT
<213> ORGANISM: Porphyromonas gingivalis

<400> SEQUENCE: 187

```
Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
                20                  25                  30

Thr Asn Glu Phe Ile Tyr Glu Pro Tyr Met Lys Ala Cys Gln Leu Pro
            35                  40                  45

Cys His Phe Val Met Gln Glu Lys Tyr Gly Gln Gly Glu Pro Ser Asp
        50                  55                  60

Glu Met Met Asn Asn Ile Leu Ala Asp Ile Arg Asn Ile Gln Phe Asp
65                  70                  75                  80

Arg Val Ile Gly Ile Gly Gly Thr Val Ile Asp Ile Ser Lys Leu
                85                  90                  95

Phe Val Leu Lys Gly Leu Asn Asp Val Leu Asp Ala Phe Asp Arg Lys
                100                 105                 110

Ile Pro Leu Ile Lys Glu Lys Glu Leu Ile Ile Val Pro Thr Thr Cys
            115                 120                 125

Gly Thr Gly Ser Glu Val Thr Asn Ile Ser Ile Ala Glu Ile Lys Ser
        130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
                180                 185                 190

Ser Pro Lys Ala Ser Pro Tyr Ser Arg Leu Phe Ser Glu Ala Ala Trp
            195                 200                 205

Asp Ile Ile Leu Glu Val Phe Lys Lys Ile Ala Glu His Gly Pro Glu
        210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
    290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
```

```
                340             345            350
Asn Asn Tyr Val Glu Leu Thr Val Asp Glu Ile Glu Gly Ile Tyr Arg
                355             360             365
Arg Leu Tyr
        370

<210> SEQ ID NO 188
<211> LENGTH: 1116
<212> TYPE: DNA
<213> ORGANISM: Porphyromonas gingivalis

<400> SEQUENCE: 188
atgcaacttt tcaaactcaa gagtgtaaca catcactttg acactttttgc agaatttgcc      60 aaggaattct gtcttggaga acgcgacttg gtaattacca acgagttcat ctatgaaccg      120
tatatgaagg catgccagct cccctgccat tttgttatgc aggagaaata tgggcaaggc      180
gagccttctg acgaaatgat gaataacatc ttggcagaca tccgtaatat ccagttcgac      240
cgcgtaatcg gtatcggagg aggtacggtt attgacatct ctaaactttt cgttctgaaa      300
ggattaaatg atgtactcga tgcattcgac cgcaaaatac ctcttatcaa agagaaagaa      360
ctgatcattg tgcccacaac atgcggaacg ggtagcgagg tgacgaacat ttctatcgca      420
gaaatcaaaa gccgtcacac caaaatggga ttggctgacg atgccattgt tgcagaccat      480
gccatcatca tacctgaact tctgaagagc ttgcctttcc acttctacgc atgcagtgca      540
atcgatgctc ttatccatgc catcgagtca tacgtatctc taaagccag tccatattct      600 cgtctgttca gtgaggcggc ttgggacatt atcctggaag tattcaagaa atcgccgaa      660 cacggccctg aataccgctt cgaaaagctg ggagaaatga tcatggccag caactatgcc      720
ggtatagcct tcggaaatgc aggagtagga gccgtccacg cactatccta cccgttggga      780
ggcaactatc acgtgccgca tggagaagca actatcagt tcttcacaga ggtattcaaa      840
gtataccaaa agaagaatcc tttcggctat atagtcgaac tcaactggaa gctctccaag      900
atactgaact gccagcccga atacgtatat ccgaagctgg atgaacttct cggatgcctt      960
cttaccaaga aaccttttgca cgaataccgg catgaaggacg aagaggtaag aggctttgcg     1020
gaatcagtgc ttaagacaca gcaaagattg ctcgccaaca actacgtaga gcttactgta     1080
gatgagatcg aaggtatcta cagaagactc tactaa                                1116

<210> SEQ ID NO 189
<211> LENGTH: 1220
<212> TYPE: PRT
<213> ORGANISM: Chloroflexus aurantiacus

<400> SEQUENCE: 189

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95
```

```
Asn Ala Gly Ser Ala Gly Ala Gln Arg Arg Leu Ala Glu Ile Pro Leu
            100                 105                 110

Thr Glu Ala Glu Leu Gly Pro Gly Ala Glu Thr Leu His Ala Ser
        115                 120                 125

Ile Ala Asn Leu Leu Gly Met Gly Trp His Leu Met Arg Ile Ala Ala
        130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
            195                 200                 205

Ile Arg Thr Val Phe Gln Arg Met Asp Gln Leu Lys Gly Arg Pro Glu
            210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
            275                 280                 285

Glu Thr Ser Leu Leu Ala Arg Thr Asp Leu Arg Thr Ile Asp Ala Ser
            290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
            355                 360                 365

Leu Asp Pro Arg Asp Pro Ala Thr Ile Asp Ala Val Phe Asp Trp Gly
            370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
            435                 440                 445

Arg Ala Arg Gly Pro Arg Val Ile Phe Leu Ser Asn Gly Ala Asp Gln
            450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510
```

-continued

```
Arg Phe Ala Asn Arg Ser Leu Glu Gly Leu Glu Phe Ala Cys Ala Trp
            515                 520                 525

Thr Ala Gln Leu Leu His Ser Gln Arg His Ile Asn Glu Ile Thr Leu
530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
            595                 600                 605

Lys Leu Glu Gln Met Gln Ala Met Ile Gln Ser Glu Leu Ala Glu Val
            610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
675                 680                 685

Leu Phe Ala Asn Leu Ile Ser Asn Tyr Ser Leu Met Arg Lys Leu Ala
            690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
            755                 760                 765

Pro Val Glu Gly Asp Arg Leu Arg Gly Thr Gly Glu Arg Pro Gly Leu
770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
            805                 810                 815

His Glu Leu Val Glu Leu Leu Pro Asn Asp Val Ala Ala Leu Glu
            820                 825                 830

Gln Asn Pro Ala Ala Pro Thr Ala Leu Arg Glu Leu Ala Arg Arg Phe
            835                 840                 845

Arg Ser Glu Gly Asp Pro Ala Ala Ser Ser Ser Ala Leu Leu Asn
850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
            915                 920                 925

Val Ala Met Ala Thr Val Tyr Tyr Leu Ala Asp Arg Asn Val Ser Gly
```

Glu Thr Phe His Pro Ser Gly Gly Leu Arg Tyr Arg Thr Pro Thr
945                 950                 955                 960

Gly Gly Glu Leu Phe Gly Leu Pro Ser Pro Glu Arg Leu Ala Glu Leu
            965                 970                 975

Val Gly Ser Thr Val Tyr Leu Ile Gly Glu His Leu Thr Glu His Leu
        980                 985                 990

Asn Leu Leu Ala Arg Ala Tyr Leu Glu Arg Tyr Gly Ala Arg Gln Val
        995                 1000                1005

Val Met Ile Val Glu Thr Glu Thr Gly Ala Glu Thr Met Arg Arg
    1010                1015                1020

Leu Leu His Asp His Val Glu Ala Gly Arg Leu Met Thr Ile Val
    1025                1030                1035

Ala Gly Asp Gln Ile Glu Ala Ala Ile Asp Gln Ala Ile Thr Arg
    1040                1045                1050

Tyr Gly Arg Pro Gly Pro Val Val Cys Thr Pro Phe Arg Pro Leu
    1055                1060                1065

Pro Thr Val Pro Leu Val Gly Arg Lys Asp Ser Asp Trp Ser Thr
    1070                1075                1080

Val Leu Ser Glu Ala Glu Phe Ala Glu Leu Cys Glu His Gln Leu
    1085                1090                1095

Thr His His Phe Arg Val Ala Arg Lys Ile Ala Leu Ser Asp Gly
    1100                1105                1110

Ala Ser Leu Ala Leu Val Thr Pro Glu Thr Thr Ala Thr Ser Thr
    1115                1120                1125

Thr Glu Gln Phe Ala Leu Ala Asn Phe Ile Lys Thr Thr Leu His
    1130                1135                1140

Ala Phe Thr Ala Thr Ile Gly Val Glu Ser Glu Arg Thr Ala Gln
    1145                1150                1155

Arg Ile Leu Ile Asn Gln Val Asp Leu Thr Arg Arg Ala Arg Ala
    1160                1165                1170

Glu Glu Pro Arg Asp Pro His Glu Arg Gln Gln Glu Leu Glu Arg
    1175                1180                1185

Phe Ile Glu Ala Val Leu Leu Val Thr Ala Pro Leu Pro Pro Glu
    1190                1195                1200

Ala Asp Thr Arg Tyr Ala Gly Arg Ile His Arg Gly Arg Ala Ile
    1205                1210                1215

Thr Val
    1220

<210> SEQ ID NO 190
<211> LENGTH: 3660
<212> TYPE: DNA
<213> ORGANISM: Chloroflexus aurantiacus

<400> SEQUENCE: 190
atgagcggaa caggacgact ggcaggaaag attgcgttaa ttaccggtgg cgccggcaat     60
atcggcagtg aattgacacg tcgctttctc gcagagggag cgacggtcat tattagtgga    120
cggaatcggg cgaagttgac cgcactggcc gaacggatgc aggcagaggc aggagtgccg    180
gcaaagcgca tcgatctcga agtcatggat gggagtgatc cggtcgcggt acgtgccggt    240
atcgaagcga ttgtggcccg tcacggccag atcgacattc tggtcaacaa tgcaggaagt    300
gccggtgccc agcgtcgtct ggccgagatt ccactcactg aagctgaatt aggccctggc    360

```
gccgaagaga cgcttcatgc cagcatcgcc aatttacttg gtatgggatg gcatctgatg    420
cgtattgcgg cacctcatat gccggtagga agtgcggtca tcaatgtctc gaccatcttt    480
tcacgggctg agtactacgg gcggattccg tatgtcaccc ctaaagctgc tcttaatgct    540
ctatctcaac ttgctgcgcg tgagttaggt gcacgtggca tccgcgttaa tacgatcttt    600
cccggcccga ttgaaagtga tcgcatccgt acagtgttcc agcgtatgga tcagctcaag    660
gggcggcccg aaggcgacac agcgcaccat ttttttgaaca ccatgcgatt gtgtcgtgcc    720
aacgaccagg gcgcgcttga acgtcggttc ccctccgtcg gtgatgtggc agacgccgct    780
gtctttctgg ccagtgccga atccgccgct ctctccggtg agacgattga ggttacgcac    840
ggaatggagt tgccggcctg cagtgagacc agcctgctgg cccgtactga tctgcgcacg    900
attgatgcca gtggccgcac gacgctcatc tgcgccggcg accagattga agaggtgatg    960
gcgctcaccg gtatgttgcg tacctgtggg agtgaagtga tcatcggctt ccgttcggct   1020
gcggcgctgg cccagttcga gcaggcagtc aatgagagtc ggcggctggc cggcgcagac   1080
tttacgcctc ccattgcctt gccactcgat ccacgcgatc cggcaacaat tgacgctgtc   1140
ttcgattggg ccggcgagaa taccggcggg attcatgcag cggtgattct gcctgctacc   1200
agtcacgaac cggcaccgtg cgtgattgag gttgatgatg agcgggtgct gaattttctg   1260
gccgatgaaa tcaccgggac aattgtgatt gccagtcgcc tggcccgtta ctggcagtcg   1320
caacggctta cccccggcgc acgtgcgcgt gggccgcgtg tcatttttct ctcgaacggt   1380
gccgatcaaa tgggaatgt ttacggacgc attcaaagtg ccgctatcgg tcagctcatt   1440
cgtgtgtggc gtcacgaggc tgaacttgac tatcagcgtg ccagcgccgc cggtgatcat   1500
gtgctgccgc cggtatgggc caatcagatt gtgcgcttcg ctaaccgcag ccttgaaggg   1560
ttagaatttg cctgtgcctg gacagctcaa ttgctccata gtcaacgcca tatcaatgag   1620
attaccctca acatccctgc caacattagc gccaccaccg gcgcacgcag tgcatcggtc   1680
ggatgggcgg aaagcctgat cgggttgcat ttggggaaag ttgccttgat taccggtggc   1740
agcgccggta ttggtgggca gatcgggcgc ctcctggctt tgagtggcgc gcgcgtgatg   1800
ctggcagccc gtgatcggca taagctcgaa cagatgcagg cgatgatcca atctgagctg   1860
gctgaggtgg ggtataccga tgtcgaagat cgcgtccaca ttgcaccggg ctgcgatgtg   1920
agtagcgaag cgcagcttgc ggatcttgtt gaacgtaccc tgtcagcttt tggcaccgtc   1980
gattatctga tcaacaacgc cgggatcgcc ggtgtcgaag agatggttat cgatatgcca   2040
gttgagggat ggcgccatac cctcttcgcc aatctgatca gcaactactc cgttgatcgc   2100
aaactggcgc cgttgatgaa aaaacagggt agcggttaca tccttaacgt ctcatcatac   2160
tttggcggtg aaaaagatgc ggccattccc tacccccaacc gtgccgatta cgccgtctcg   2220
aaggctggtc agcgggcaat ggccgaagtc tttgcgcgct tccttggccc ggagatacag   2280
atcaatgcca ttgcgccggg tccggtcgaa ggtgatcgct tgcgcggtac cggtgaacgt   2340
cccggcctct ttgcccgtcg ggcgcggctg attttggaga acaagcggct gaatgagctt   2400
cacgctgctc ttatcgcggc tgcgcgcacc gatgagcgat ctatgcacga actggttgaa   2460
ctgctcttac ccaatgatgt ggccgcacta gagcagaatc ccgcagcacc taccgcgttg   2520
cgtgaactgg cacgacgttt tcgcagcgaa ggcgatccgg cggcatcatc aagcagtgcg   2580
ctgctgaacc gttcaattgc cgctaaattg ctggctcgtt tgcataatgg tggctatgtg   2640
ttgcctgcca acatctttgc aaacctgcca aacccgcccg atcccttctt cacccgagcc   2700
cagattgatc gcgaggctcg caaggttcgt gacggcatca tggggatgct ctacctgcaa   2760
```

```
cggatgccga ctgagtttga tgtcgcaatg gccaccgtct attaccttgc cgaccgcaat    2820
gtcagtggtg agacattcca cccatcaggt ggtttgcgtt acgaacgcac ccctaccggt    2880
ggcgaactct tcggcttgcc ctcaccggaa cggctggcgg agctggtcgg aagcacggtc    2940
tatctgatag gtgaacatct gactgaacac cttaacctgc ttgcccgtgc gtacctcgaa    3000
cgttacgggg cacgtcaggt agtgatgatt gttgagacag aaaccggggc agagacaatg    3060
cgtcgcttgc tccacgatca cgtcgaggct ggtcggctga tgactattgt ggccggtgat    3120
cagatcgaag ccgctatcga ccaggctatc actcgctacg gtcgcccagg gccggtcgtc    3180
tgtaccccct tccggccact gccgacggta ccactggtcg ggcgtaaaga cagtgactgg    3240
agcacagtgt tgagtgaggc tgaatttgcc gagttgtgcg aacaccagct cacccaccat    3300
ttccgggtag cgcgcaagat tgccctgagt gatggtgcca gtctcgcgct ggtcactccc    3360
gaaactacgg ctacctcaac taccgagcaa tttgctctgg ctaacttcat caaaacgacc    3420
cttcacgctt ttacggctac gattggtgtc gagagcgaaa gaactgctca gcgcattctg    3480
atcaatcaag tcgatctgac ccggcgtgcg cgtgccgaag agccgcgtga tccgcacgag    3540
cgtcaacaag aactggaacg ttttatcgag gcagtcttgc tggtcactgc accactcccg    3600
cctgaagccg ataccgtta cgccgggcgg attcatcgcg gacgggcgat taccgtgtaa    3660
```

<210> SEQ ID NO 191
<211> LENGTH: 455
<212> TYPE: PRT
<213> ORGANISM: Chloroflexus aurantiacus

<400> SEQUENCE: 191

```
Met Ala Lys Ala Ser Arg Leu Thr Arg Ser Thr Gly Gln Pro Thr Glu
1               5                   10                  15

Val Ser Glu Gly Gln Val Thr Gly Thr Ser Glu Met Pro Pro Thr Gly
                20                  25                  30

Glu Glu Pro Ser Gly His Ala Glu Ser Lys Pro Ala Ser Asp Pro
            35                  40                  45

Met Ser Thr Pro Gly Thr Gly Gln Glu Gln Leu Pro Leu Ser Gly Ile
        50                  55                  60

Arg Val Ile Asp Val Gly Asn Phe Leu Ala Gly Pro Tyr Ala Ala Ser
65                  70                  75                  80

Ile Leu Gly Glu Phe Gly Ala Glu Val Leu Lys Ile Glu His Pro Leu
                85                  90                  95

Gly Gly Asp Pro Met Arg Arg Phe Gly Thr Ala Thr Ala Arg His Asp
            100                 105                 110

Ala Thr Leu Ala Trp Leu Ser Glu Ala Arg Asn Arg Lys Ser Val Thr
        115                 120                 125

Ile Asp Leu Arg Gln Gln Glu Gly Val Ala Leu Phe Leu Lys Leu Val
    130                 135                 140

Ala Lys Ser Asp Ile Leu Ile Glu Asn Phe Arg Pro Gly Thr Met Glu
145                 150                 155                 160

Glu Trp Gly Leu Ser Trp Pro Val Leu Gln Ala Thr Asn Pro Gly Leu
                165                 170                 175

Ile Met Leu Arg Val Ser Gly Tyr Gly Gln Thr Gly Pro Tyr Arg Arg
            180                 185                 190

Arg Ser Gly Phe Ala His Ile Ala His Ala Phe Ser Gly Leu Ser Tyr
        195                 200                 205

Leu Ala Gly Phe Pro Gly Glu Thr Pro Val Leu Pro Gly Thr Ala Pro
```

```
                        210                 215                 220
Leu Gly Asp Tyr Ile Ala Ser Leu Phe Gly Ala Ile Gly Ile Leu Ile
225                 230                 235                 240

Ala Leu Arg His Lys Glu Gln Thr Gly Arg Gly Gln Leu Ile Asp Val
                245                 250                 255

Gly Ile Tyr Glu Ala Val Phe Arg Ile Leu Asp Glu Ile Ala Pro Ala
            260                 265                 270

Tyr Gly Leu Phe Gly Lys Ile Arg Glu Arg Glu Gly Ala Gly Ser Phe
        275                 280                 285

Ile Ala Val Pro His Gly His Phe Arg Ser Lys Asp Gly Lys Trp Val
    290                 295                 300

Ala Ile Ala Cys Thr Thr Asp Lys Met Phe Glu Arg Leu Ala Glu Ala
305                 310                 315                 320

Met Glu Arg Pro Glu Leu Ala Ser Pro Glu Leu Tyr Gly Asp Gln Arg
                325                 330                 335

Lys Arg Leu Ala Ala Arg Asp Ile Val Asn Gln Ile Thr Ile Glu Trp
            340                 345                 350

Val Gly Ser Leu Thr Arg Asp Glu Val Met Arg Arg Cys Leu Glu Lys
        355                 360                 365

Glu Val Pro Val Gly Pro Leu Asn Ser Ile Ala Asp Met Phe Asn Asp
    370                 375                 380

Glu His Phe Leu Ala Arg Gly Asn Phe Ala Cys Ile Glu Ala Glu Gly
385                 390                 395                 400

Ile Gly Glu Val Val Pro Asn Val Ile Pro Arg Leu Ser Glu Thr
                405                 410                 415

Pro Gly Arg Val Thr Asn Leu Gly Pro Pro Leu Gly Asn Ala Thr Tyr
            420                 425                 430

Glu Val Leu Arg Glu Leu Leu Asp Ile Ser Ala Glu Gly Ile Lys Arg
        435                 440                 445

Leu Arg Ser Arg Lys Ile Ile
    450                 455

<210> SEQ ID NO 192
<211> LENGTH: 1368
<212> TYPE: PRT
<213> ORGANISM: Chloroflexus aurantiacus

<400> SEQUENCE: 192

Ala Thr Gly Gly Cys Ala Ala Ala Gly Gly Cys Thr Cys Ala Cys
1               5                   10                  15

Gly Cys Cys Thr Gly Ala Cys Cys Ala Gly Cys Thr Cys Ala Ala Cys
                20                  25                  30

Cys Gly Gly Thr Cys Ala Gly Cys Cys Ala Ala Cys Gly Gly Ala Gly
            35                  40                  45

Gly Thr Gly Thr Cys Ala Gly Ala Ala Gly Gly Ala Cys Ala Gly Gly
        50                  55                  60

Thr Cys Ala Cys Cys Gly Gly Ala Cys Ala Ala Gly Cys Gly Gly Ala
65                  70                  75                  80

Gly Ala Thr Gly Cys Cys Cys Cys Cys Ala Cys Ala Gly Gly Ala
                85                  90                  95

Gly Ala Ala Gly Ala Cys Cys Ala Thr Cys Ala Gly Gly Ala Cys
            100                 105                 110

Ala Cys Gly Cys Ala Gly Ala Ala Thr Cys Ala Ala Ala Gly Cys Cys
        115                 120                 125
```

-continued

```
Gly Cys Cys Gly Gly Cys Cys Ala Gly Thr Gly Ala Thr Cys Cys Gly
    130                 135                 140

Ala Thr Gly Ala Gly Cys Ala Cys Ala Cys Cys Gly Gly Gly Cys Ala
145                 150                 155                 160

Cys Cys Gly Gly Thr Cys Ala Gly Gly Ala Gly Cys Ala Gly Thr Thr
                165                 170                 175

Gly Cys Cys Gly Thr Thr Gly Ala Gly Thr Gly Gly Cys Ala Thr Thr
                180                 185                 190

Cys Gly Gly Gly Thr Cys Ala Thr Thr Gly Ala Thr Gly Thr Ala Gly
            195                 200                 205

Gly Thr Ala Ala Thr Thr Thr Thr Cys Thr Gly Cys Cys Gly Gly
    210                 215                 220

Cys Cys Cys Gly Thr Ala Thr Gly Cys Thr Gly Cys Thr Thr Cys Cys
225                 230                 235                 240

Ala Thr Cys Cys Thr Gly Gly Thr Gly Ala Ala Thr Thr Cys Gly
                245                 250                 255

Gly Thr Gly Cys Cys Gly Ala Gly Thr Gly Cys Thr Cys Ala Ala
        260                 265                 270

Gly Ala Thr Cys Gly Ala Ala Cys Ala Cys Cys Gly Cys Thr Gly
    275                 280                 285

Gly Gly Thr Gly Gly Cys Gly Ala Thr Cys Cys Gly Ala Thr Gly Cys
        290                 295                 300

Gly Thr Cys Gly Thr Thr Thr Cys Gly Gly Cys Ala Cys Thr Gly Cys
305                 310                 315                 320

Ala Ala Cys Thr Gly Cys Gly Cys Cys Ala Cys Gly Ala Thr
                325                 330                 335

Gly Cys Ala Ala Cys Ala Cys Thr Gly Gly Cys Cys Thr Gly Gly Cys
                340                 345                 350

Thr Gly Ala Gly Cys Gly Ala Gly Gly Cys Cys Gly Thr Ala Ala
        355                 360                 365

Cys Cys Gly Thr Ala Ala Gly Thr Cys Gly Gly Thr Cys Ala Cys Gly
    370                 375                 380

Ala Thr Thr Gly Ala Thr Cys Thr Gly Cys Gly Thr Cys Ala Gly Cys
385                 390                 395                 400

Ala Ala Gly Ala Gly Gly Cys Gly Thr Thr Gly Cys Gly Cys Thr
                405                 410                 415

Cys Thr Thr Thr Cys Thr Gly Ala Ala Gly Cys Thr Gly Gly Thr Cys
                420                 425                 430

Gly Cys Cys Ala Ala Thr Cys Cys Gly Ala Cys Ala Thr Thr Cys
    435                 440                 445

Thr Gly Ala Thr Thr Gly Ala Ala Ala Cys Thr Thr Cys Thr Gly
450                 455                 460

Cys Cys Cys Cys Gly Gly Thr Ala Cys Gly Ala Thr Gly Ala Ala
465                 470                 475                 480

Gly Ala Ala Thr Gly Gly Gly Cys Thr Thr Gly Ala Gly Cys Thr
                485                 490                 495

Gly Gly Cys Cys Thr Gly Thr Thr Thr Gly Cys Ala Gly Gly Cys
            500                 505                 510

Gly Ala Cys Gly Ala Ala Thr Cys Cys Gly Gly Ala Cys Thr Gly
        515                 520                 525

Ala Thr Thr Ala Thr Gly Cys Thr Gly Cys Gly Gly Thr Gly Thr
    530                 535                 540

Cys Gly Gly Gly Cys Thr Ala Thr Gly Gly Thr Cys Ala Gly Ala Cys
```

-continued

```
        545                 550                 555                 560
Cys Gly Gly Cys Cys Gly Thr Ala Cys Cys Gly Thr Cys Gly Gly
                565                 570                 575
Cys Gly Thr Thr Cys Gly Gly Gly Thr Thr Gly Cys Cys Cys
                580                 585                 590
Ala Thr Ala Thr Thr Gly Cys Cys Ala Cys Gly Cys Thr Thr Thr
                595                 600                 605
Cys Ala Gly Cys Gly Gly Cys Cys Thr Cys Thr Cys Gly Thr Ala Thr
        610                 615                 620
Cys Thr Gly Gly Cys Cys Gly Gly Thr Thr Cys Cys Cys Gly
625                 630                 635                 640
Gly Cys Gly Ala Ala Ala Cys Gly Cys Cys Ala Gly Thr Cys Thr Thr
                645                 650                 655
Gly Cys Cys Gly Gly Ala Ala Cys Gly Gly Cys Ala Cys Cys Gly
                660                 665                 670
Cys Thr Cys Gly Gly Cys Gly Ala Cys Thr Ala Thr Ala Thr Cys Gly
        675                 680                 685
Cys Cys Ala Gly Thr Cys Thr Gly Thr Thr Cys Gly Gly Gly Gly Cys
        690                 695                 700
Gly Ala Thr Thr Gly Gly Ala Thr Thr Thr Gly Ala Thr Cys
705                 710                 715                 720
Gly Cys Gly Cys Thr Gly Cys Gly Cys Cys Ala Cys Ala Ala Ala Gly
                725                 730                 735
Ala Gly Cys Ala Gly Ala Cys Cys Gly Gly Ala Cys Gly Cys Gly Gly
                740                 745                 750
Gly Cys Ala Gly Thr Thr Gly Ala Thr Cys Gly Ala Thr Gly Thr Cys
        755                 760                 765
Gly Gly Gly Ala Thr Thr Thr Ala Cys Gly Ala Ala Cys Gly Gly
        770                 775                 780
Thr Cys Thr Thr Cys Cys Gly Gly Ala Thr Thr Cys Thr Gly Gly Ala
785                 790                 795                 800
Thr Gly Ala Gly Ala Thr Thr Gly Cys Cys Cys Gly Gly Cys Thr
                805                 810                 815
Thr Ala Cys Gly Gly Thr Cys Thr Gly Thr Thr Cys Gly Gly Cys Ala
                820                 825                 830
Ala Gly Ala Thr Thr Cys Gly Thr Gly Ala Ala Cys Gly Cys Gly Ala
                835                 840                 845
Ala Gly Gly Gly Cys Cys Gly Gly Gly Ala Gly Thr Thr Thr Thr
                850                 855                 860
Ala Thr Thr Gly Cys Thr Gly Thr Thr Cys Gly Cys Ala Thr Gly
865                 870                 875                 880
Gly Cys Cys Ala Thr Thr Cys Cys Gly Cys Thr Cys Gly Ala Ala
                885                 890                 895
Gly Gly Ala Cys Gly Cys Ala Ala Gly Thr Gly Gly Thr Thr
                900                 905                 910
Gly Cys Gly Ala Thr Thr Gly Cys Cys Thr Gly Thr Ala Cys Cys Ala
                915                 920                 925
Cys Cys Gly Ala Cys Ala Ala Gly Ala Thr Gly Thr Thr Thr Gly Ala
        930                 935                 940
Ala Cys Gly Gly Cys Thr Gly Gly Cys Cys Gly Ala Ala Gly Cys Ala
945                 950                 955                 960
Ala Thr Gly Gly Ala Gly Cys Gly Cys Cys Gly Gly Ala Ala Cys
                965                 970                 975
```

-continued

```
Thr Gly Gly Cys Thr Thr Cys Gly Cys Cys Gly Gly Ala Ala Cys Thr
            980                 985                 990
Gly Thr Ala Cys Gly Gly Cys Gly  Ala Thr Cys Ala Ala  Cys Gly Cys
            995                 1000                1005
Ala Ala  Ala Cys Gly Gly Cys  Thr Gly Gly Cys Ala  Gly Cys Ala
            1010                1015                1020
Cys Gly  Cys Gly Ala Thr Ala  Thr Thr Gly Thr Gly  Ala Ala Cys
            1025                1030                1035
Cys Ala  Gly Ala Thr Cys Ala  Cys Gly Ala Thr Thr  Gly Ala Ala
            1040                1045                1050
Thr Gly  Gly Gly Thr Cys Gly  Gly Thr Thr Cys Gly  Thr Thr Gly
            1055                1060                1065
Ala Cys  Gly Cys Gly Cys Gly  Ala Cys Gly Ala Gly  Gly Thr Gly
            1070                1075                1080
Ala Thr  Gly Cys Gly Gly Cys  Gly Thr Thr Gly Thr  Cys Thr Gly
            1085                1090                1095
Gly Ala  Gly Ala Ala Gly Gly  Ala Ala Gly Thr Thr  Cys Cys Cys
            1100                1105                1110
Gly Thr  Thr Gly Gly Cys Cys  Cys Ala Cys Thr Cys  Ala Ala Cys
            1115                1120                1125
Ala Gly  Cys Ala Thr Cys Gly  Cys Cys Gly Ala Thr  Ala Thr Gly
            1130                1135                1140
Thr Thr  Cys Ala Ala Cys Gly  Ala Cys Gly Ala Ala  Cys Ala Thr
            1145                1150                1155
Thr Thr  Thr Cys Thr Gly Gly  Cys Thr Cys Gly Cys  Gly Gly Cys
            1160                1165                1170
Ala Ala  Cys Thr Thr Thr Gly  Cys Cys Thr Gly Thr  Ala Thr Cys
            1175                1180                1185
Gly Ala  Ala Gly Cys Cys Gly  Ala Gly Gly Thr Ala  Thr Cys
            1190                1195                1200
Gly Gly  Cys Gly Ala Ala Gly  Thr Gly Gly Thr Gly  Gly Thr Thr
            1205                1210                1215
Cys Cys  Gly Ala Ala Cys Gly  Thr Gly Ala Thr Cys  Cys Cys Cys
            1220                1225                1230
Ala Gly  Ala Cys Thr Gly Thr  Cys Ala Gly Ala Ala  Ala Cys Ala
            1235                1240                1245
Cys Cys  Gly Gly Gly Ala Cys  Gly Gly Gly Thr Gly  Ala Cys Cys
            1250                1255                1260
Ala Ala  Cys Cys Thr Cys Gly  Gly Cys Cys Cys Ala  Cys Cys Gly
            1265                1270                1275
Cys Thr  Gly Gly Gly Gly Ala  Ala Thr Gly Cys Cys  Ala Cys Gly
            1280                1285                1290
Thr Ala  Thr Gly Ala Gly Gly  Thr Gly Thr Thr Gly  Cys Gly Cys
            1295                1300                1305
Gly Ala  Gly Cys Thr Gly Cys  Thr Thr Gly Ala Thr  Ala Thr Thr
            1310                1315                1320
Thr Cys  Thr Gly Cys Cys Gly  Ala Ala Gly Ala Gly  Ala Thr Cys
            1325                1330                1335
Ala Ala  Gly Cys Gly Thr Cys  Thr Gly Cys Gly Cys  Ala Gly Cys
            1340                1345                1350
Cys Gly  Cys Ala Ala Gly Ala  Thr Thr Ala Thr Thr  Thr Ala Gly
            1355                1360                1365
```

<210> SEQ ID NO 193
<211> LENGTH: 405
<212> TYPE: PRT
<213> ORGANISM: Chloroflexus aurantiacus

<400> SEQUENCE: 193

```
Met Asp Gly Thr Thr Thr Thr Leu Pro Leu Ala Gly Ile Arg Val Ile
1               5                   10                  15

Asp Ala Ala Thr Val Ile Ala Ala Pro Phe Cys Ala Thr Leu Leu Gly
            20                  25                  30

Glu Phe Gly Ala Asp Val Leu Lys Val Glu His Pro Ile Gly Gly Asp
        35                  40                  45

Ala Leu Arg Arg Phe Gly Thr Pro Thr Ala Arg Gly Asp Thr Leu Thr
    50                  55                  60

Trp Leu Ser Glu Ser Arg Asn Lys Arg Ser Val Thr Leu Asn Leu Gln
65                  70                  75                  80

His Pro Glu Gly Ala Arg Val Phe Lys Glu Leu Ile Ala His Ser Asp
                85                  90                  95

Val Leu Cys Glu Asn Phe Arg Pro Gly Thr Leu Glu Lys Trp Gly Leu
            100                 105                 110

Gly Trp Asp Val Leu Ser Lys Ile Asn Pro Arg Leu Ile Met Leu Arg
        115                 120                 125

Val Thr Gly Tyr Gly Gln Thr Gly Pro Tyr Arg Asp Arg Pro Gly Phe
    130                 135                 140

Ala Arg Ile Ala His Ala Val Gly Gly Ile Ala Tyr Leu Ala Gly Met
145                 150                 155                 160

Pro Lys Gly Thr Pro Val Thr Pro Gly Ser Thr Thr Leu Ala Asp Tyr
                165                 170                 175

Met Thr Gly Leu Tyr Gly Cys Ile Gly Val Leu Leu Ala Leu Arg His
            180                 185                 190

Arg Glu Gln Thr Gly Arg Gly Gln Tyr Ile Asp Ala Ala Leu Tyr Glu
        195                 200                 205

Ser Val Phe Arg Cys Ser Asp Glu Leu Val Pro Ala Tyr Gly Met Tyr
    210                 215                 220

Arg Lys Val Arg Glu Arg His Gly Ser His Tyr Asn Glu Phe Ala Cys
225                 230                 235                 240

Pro His Gly His Phe Gln Thr Lys Asp Gly Lys Trp Val Ala Ile Ser
                245                 250                 255

Cys Ala Thr Asp Lys Leu Phe Ala Arg Leu Ala Asn Ala Met Gly Arg
            260                 265                 270

Pro Glu Leu Ala Ser Ser Val Tyr Gly Asp Gln Lys Val Arg Leu
        275                 280                 285

Ala His Ala Ser Asp Val Asn Glu Ile Val Arg Asp Trp Cys Ser Ser
    290                 295                 300

Leu Thr Arg Ala Glu Val Leu Glu Arg Cys Tyr Ala Thr Ala Thr Pro
305                 310                 315                 320

Ala Ala Pro Leu Asn Asp Ile Ala Asp Phe Phe Gly Asp Arg His Val
                325                 330                 335

His Ala Arg Arg Asn Leu Val Ala Ile Asp Ala Glu Asp Leu Gly Glu
            340                 345                 350

Thr Leu Ile Met Pro Asn Val Val Pro Lys Leu Ser Glu Thr Pro Gly
        355                 360                 365

Ser Ile Arg Ser Leu Gly Pro Lys Leu Gly Glu His Thr Glu Glu Val
    370                 375                 380
```

```
Leu Lys Glu Ile Leu Gly Met Cys Asp Glu Gln Ile Asn Asp Leu Arg
385                 390                 395                 400

Ser Lys Arg Val Ile
                405
```

<210> SEQ ID NO 194
<211> LENGTH: 1218
<212> TYPE: DNA
<213> ORGANISM: Chloroflexus aurantiacus

<400> SEQUENCE: 194

```
atggatggaa cgaccacaac gttgccgctg gccggaattc gcgttatcga tgccgcgacg    60
gtgattgctg cgccttttg tgcgaccctg ttgggcgaat cggcgctga cgtgttgaaa    120
gtagaacatc ctatcggcgg tgatgcgctg cgccgcttcg ggacgccgac cgcacgcggc    180
gatacgctga cctggctgag cgagtcgcgc aacaagcgtt cggttacgct caacctgcaa    240
catcccgaag gggcgcgtgt cttcaaagag ctgatcgccc actccgatgt gctgtgcgaa    300
aattttcgcc ccggtacgct ggaaaaatgg gggctgggtt gggatgtgtt gagcaagatc    360
aacccgcgcc tgattatgtt gcgggtcacc ggctatgggc agaccgggcc gtaccgtgat    420
cgaccggggt ttgcccggat tgcgcacgcc gtcggtggca tcgcgtatct ggccggtatg    480
ccgaaaggga caccggtgac gccggggtca acgacactcg ccgattacat gaccggtctc    540
tacggctgta ttggcgtgct gctggcgctg cgccaccgcg aacagaccgg acgcggccag    600
tacattgatg ccgctctgta cgaatcggtc ttccgctgta gcgatgagct ggtgccggcc    660
tacgggatgt atcgcaaggt gcgtgaacgc cacggttccc actacaacga gtttgcctgt    720
cctcacggcc acttccagac caaagacggg aaatgggtgg cgatctcgtg tgcgaccgat    780
aagctgttg cccgactggc aaatgcgatg gggcgcccg aactggcgtc gtcgagtgtc    840
tacggcgacc agaaagtacg gctggcgcac gccagtgatg tgaacgagat tgtgcgtgac    900
tggtgtagct cgctgacccg cgccgaagtg cttgagcgct gttacgccac ggctaccccg    960
gcggcaccgc tgaacgacat tgccgacttc ttcggtgatc gccacgtcca cgctcgtcgg   1020
aatctggtcg cgattgatgc cgaagacctg ggggagacgt tgatcatgcc gaatgtggtg   1080
ccaaagctct cggagacacc gggcagcatt cgctcgctcg gcccgaaact cggcgagcat   1140
acggaagagg tcttgaaaga gattctcggc atgtgcgacg agcagatcaa cgatctgcgt   1200
tcaaagcggg tgatatag                                                1218
```

<210> SEQ ID NO 195
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 195

```
ttgtcaacga tggggtcatg                                                20
```

<210> SEQ ID NO 196
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 196
aaaaatgccg acataacgtc                                               20

<210> SEQ ID NO 197
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 197
ccatccgttg aatgagtttt                                               20

<210> SEQ ID NO 198
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 198
tggtgttaac tggcaaaatc                                               20

<210> SEQ ID NO 199
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 199
gtgacttcca acggcaaaag                                               20

<210> SEQ ID NO 200
<211> LENGTH: 20
<212> TYPE: DNA
<213> ORGANISM: Artificial Sequence
<220> FEATURE:
<223> OTHER INFORMATION: Synthetic Construct - Primer for amplification

<400> SEQUENCE: 200
ccgttggttt gatagcaata                                               20

<210> SEQ ID NO 201
<211> LENGTH: 1080
<212> TYPE: DNA
<213> ORGANISM: Sulfolobus tokodaii

<400> SEQUENCE: 201
atgattctga tgcgccgtac cctgaaagcg gcaatcttgg gtgccaccgg cttagtcggg      60
attgagtacg tacggatgct gagcaatcat ccgtacatca aaccgcccta tctggctggg     120
aaagggtcag ttggcaaacc gtatggcgaa gtagtgcgct ggcagactgt gggccaagtt     180
cccaaagaaa ttgccgatat ggaaatcaag ccgactgatc cgaaactgat ggatgatgtt     240
gacatcatct ttagcccact gcctcaaggt gcggcaggac ccgttgagga caatttgcg      300 aaagaaggat ttccggtcat ttccaattct ccggatcatc ggtttgatcc ggatgtccca     360
ctcctggtgc cagaactgaa tccgcacacc attagcctta ttgacgaaca gcgtaaacgc     420
cgtgaatgga aaggcttcat cgttacgacg ccgttatgca ccgcacaggg tgctgcgatc     480
ccattgggtg ccatcttcaa ggactacaaa atggatggcg cattcattac gaccattcag     540
tctcttagcg gtgcgggata tccgggtatt ccgtccctgg atgtggtgga taacattctg     600
cctttagggg acggccctga cgccaaaacg atcaaggaaa ttttccgcat cctgagtgaa     660

-continued

```
gtgaaacgca atgtggacga acctaaactg gaggacgttt cactggccgc cacaacccat    720
cgcattgcaa ccattcatgg ccactatgag gtgttgtacg tgtcgtttaa ggaagaaaca    780
gcagcggaga aggtcaaaga aacgctggaa aactttcgcg gtgaacctca ggatctcaaa    840
ctgccgacag cgccctcgaa accgatcatt gtgatgaacg aagatactcg cccacaggta    900
tatttcgatc gttgggcggg cgacattccg ggcatgagtg tcgttgttgg ccgtctgaaa    960
caggtcaaca aacgcatgat tcgtctggta tcgcttatcc acaacaccgt acgtggtgct   1020
gcgggcggtg ggattttagc tgcggagttg ctcgtggaga aaggctacat cgagaagtaa   1080
```

<210> SEQ ID NO 202
<211> LENGTH: 359
<212> TYPE: PRT
<213> ORGANISM: Sulfolobus tokodaii

<400> SEQUENCE: 202

```
Met Ile Leu Met Arg Arg Thr Leu Lys Ala Ala Ile Leu Gly Ala Thr
1               5                  10                  15

Gly Leu Val Gly Ile Glu Tyr Val Arg Met Leu Ser Asn His Pro Tyr
            20                  25                  30

Ile Lys Pro Ala Tyr Leu Ala Gly Lys Gly Ser Val Gly Lys Pro Tyr
        35                  40                  45

Gly Glu Val Val Arg Trp Gln Thr Val Gly Gln Val Pro Lys Glu Ile
    50                  55                  60

Ala Asp Met Glu Ile Lys Pro Thr Asp Pro Lys Leu Met Asp Asp Val
65                  70                  75                  80

Asp Ile Ile Phe Ser Pro Leu Pro Gln Gly Ala Ala Gly Pro Val Glu
                85                  90                  95

Glu Gln Phe Ala Lys Glu Gly Phe Pro Val Ile Ser Asn Ser Pro Asp
            100                 105                 110

His Arg Phe Asp Pro Asp Val Pro Leu Leu Val Pro Glu Leu Asn Pro
        115                 120                 125

His Thr Ile Ser Leu Ile Asp Glu Gln Arg Lys Arg Arg Glu Trp Lys
    130                 135                 140

Gly Phe Ile Val Thr Thr Pro Leu Cys Thr Ala Gln Gly Ala Ala Ile
145                 150                 155                 160

Pro Leu Gly Ala Ile Phe Lys Asp Tyr Lys Met Asp Gly Ala Phe Ile
                165                 170                 175

Thr Thr Ile Gln Ser Leu Ser Gly Ala Gly Tyr Pro Gly Ile Pro Ser
            180                 185                 190

Leu Asp Val Val Asp Asn Ile Leu Pro Leu Gly Asp Gly Pro Asp Ala
        195                 200                 205

Lys Thr Ile Lys Glu Ile Phe Arg Ile Leu Ser Glu Val Lys Arg Asn
    210                 215                 220

Val Asp Glu Pro Lys Leu Glu Asp Val Ser Leu Ala Ala Thr Thr His
225                 230                 235                 240

Arg Ile Ala Thr Ile His Gly His Tyr Glu Val Leu Tyr Val Ser Phe
                245                 250                 255

Lys Glu Glu Thr Ala Ala Glu Lys Val Lys Thr Leu Glu Asn Phe
            260                 265                 270

Arg Gly Glu Pro Gln Asp Leu Lys Leu Pro Thr Ala Pro Ser Lys Pro
        275                 280                 285

Ile Ile Val Met Asn Glu Asp Thr Arg Pro Gln Val Tyr Phe Asp Arg
    290                 295                 300
```

Trp Ala Gly Asp Ile Pro Gly Met Ser Val Val Gly Arg Leu Lys
305                 310                 315                 320

Gln Val Asn Lys Arg Met Ile Arg Leu Val Ser Leu Ile His Asn Thr
                325                 330                 335

Val Arg Gly Ala Ala Gly Gly Gly Ile Leu Ala Ala Glu Leu Leu Val
            340                 345                 350

Glu Lys Gly Tyr Ile Glu Lys
        355

<210> SEQ ID NO 203
<211> LENGTH: 8457
<212> TYPE: DNA
<213> ORGANISM: Artificial Sequence
<220> FEATURE:
<223> OTHER INFORMATION: Synthetic Construct - plasmid

<400> SEQUENCE: 203

| | | | | |
|---|---|---|---|---|
| ttcgagctcg | gtaatgtcgt | ttaccctgat | tcagcaagcg | actccgcgct | tacatcgcag | 60 |
| cgaacttgcg | gttccgggtt | caaatccgac | ctttatggag | aaatcagcag | ccagcaaggc | 120 |
| cgatgtcatc | ttcttggatc | tggaggatgc | cgttgcacct | gatgacaaag | aacaggcgcg | 180 |
| taagaacatc | attcaggcac | tgaacgatct | ggactggggc | aacaaaacga | tgatgatccg | 240 |
| cattaacggt | ctggacaccc | actacatgta | tcgggatgtg | gtcgacatcg | tagaagcatg | 300 |
| ccctcgcctg | gatatgattc | tcattcccaa | agtcggagta | ccagcagacg | tgtatgcgat | 360 |
| tgatgtgctg | acgacgcaaa | tcgaacaggc | gaagaaacgg | gagaagaaaa | tcggattcga | 420 |
| ggtgctcatt | gaaacggctt | taggcatggc | caatgttgaa | gccatcgcca | catcttcgaa | 480 |
| acgcttggaa | gcgatgtcgt | ttggtgtggc | cgattatgca | gcatccactc | gtgcccgtag | 540 |
| taccgtgatt | ggtggtgtga | atgcggatta | ctccgttctc | actgacaaag | atgaagcagg | 600 |
| gaaccgtcaa | acccattggc | aagatccgtg | gctgtttgcg | cagaatcgca | tgctggttgc | 660 |
| ttgccgtgct | tacgggcttc | gcccgattga | tgggccattt | ggcgacttca | gcgatcccga | 720 |
| tggctatacc | agtgctgcgc | gtcgttgtgc | ggcgctgggc | tttgaaggca | aatgggcgat | 780 |
| tcacccgagt | cagatcgact | tagcgaacga | ggtgttcaca | ccgtctgaag | ctgaagtcac | 840 |
| caaagcgcgc | cgcattctgg | aggcaatgga | agaagcggcc | aaagccggtc | gtggcgctgt | 900 |
| aagcctggac | ggtcgcttga | ttgacatcgc | cagcattcgc | atggctgaag | ccctgatcca | 960 |
| gaaagcggat | gcaatgggcg | gcaaataagt | ttaactttaa | gaaggagata | taccatgatt | 1020 |
| ctgatgcgcc | gtaccctgaa | agcggcaatc | ttgggtgcca | ccggcttagt | cgggattgag | 1080 |
| tacgtacgga | tgctgagcaa | tcatccgtac | atcaaacccg | cctatctggc | tgggaaaggg | 1140 |
| tcagttggca | aaccgtatgg | cgaagtagtg | cgctggcaga | ctgtgggcca | agttcccaaa | 1200 |
| gaaattgccg | atatggaaat | caagccgact | gatccgaaac | tgatggatga | tgttgacatc | 1260 |
| atctttagcc | cactgcctca | aggtgcggca | ggacccgttg | aggaacaatt | gcgaaagaa | 1320 |
| ggatttccgg | tcatttccaa | ttctccggat | catcggtttg | atccggatgt | cccactcctg | 1380 |
| gtgccagaac | tgaatccgca | caccattagc | cttattgacg | aacagcgtaa | acgccgtgaa | 1440 |
| tggaaaggct | tcatcgttac | gacgccgtta | tgcaccgcac | agggtgctgc | gatcccattg | 1500 |
| ggtgccatct | tcaaggacta | caaaatggat | ggcgcattca | ttacgaccat | tcagtctctt | 1560 |
| agcggtgcgg | gatatccggg | tattccgtcc | ctgatgtgg | tggataacat | tctgccttta | 1620 |
| ggggacggcc | ctgacgccaa | aacgatcaag | gaaattttcc | gcatcctgag | tgaagtgaaa | 1680 |

```
cgcaatgtgg acgaacctaa actggaggac gtttcactgg ccgccacaac ccatcgcatt   1740
gcaaccattc atggccacta tgaggtgttg tacgtgtcgt ttaaggaaga aacagcagcg   1800
gagaaggtca agaaacgct ggaaaacttt cgcggtgaac ctcaggatct caaactgccg    1860
acagcgccct cgaaaccgat cattgtgatg aacgaagata ctcgcccaca ggtatatttc   1920
gatcgttggg cggcgacat tccgggcatg agtgtcgttg ttggccgtct gaaacaggtc    1980
aacaaacgca tgattcgtct ggtatcgctt atccacaaca ccgtacgtgg tgctgcgggc   2040
ggtgggattt tagctgcgga gttgctcgtg gagaaaggct acatcgagaa gtaagtttaa   2100
ctttaagaag gagatatacc atgaaagcag cagttctgca tacctataaa gaaccgctga   2160
gcattgaaga tgtgaatatt tcacagccga agccggtga agtgaaaatc aaagttaaag    2220
caaccggtct gtgtcgtagt gatgttcatg tttttgaagg taaaacaccg gttccgcctc   2280
cggttgttgc aggtcatgaa attagcgta ttgttgaaga ggttggtccg ggtgttaccc    2340
gtgttaaacc gggtgatcgt gttattagcg catttattca tccgtgtggt aaatgcggta   2400
attgtgttgc cggtaaagaa aatctgtgtg aaacctttag ccaggttcgt ctgaaaggtg   2460
ttatgccgga tggcaccagc cgtctgagca agatggcaa agaaattcgt accttttctgg   2520 gtggtggttt tgcagaatat gcaattgttg gtgaaaatgc actgacccgt gttccggaag   2580
atatggatct ggaaaaagtt gcagttctgg gttgtgccgg tctgaccggt tatggtgcaa   2640
ttagcagcag caaaattgaa cctggtgata ccgttgcagt tattggtgtt ggtggtgtgg   2700
gtctgagcac cattcagctg ctgcgtgcaa gcggtgcagg tcgtattatt gcagttggca   2760
ccaaaaaatg gaaactggat cgtgcaatgg aactgggtgc aaccgatgtt gttaacagta   2820
aagaaattga tccggtgaaa gccatcaaag aaatcaccgg tggtggtccg caggttgtta   2880
ttgaagccgg tggtaatgaa gataccattc acatggcact ggatagcgtt cgtattggtg   2940
gtaaagttgt tctggttggt ctgcctccgg caaccgcaat gattccgatt cgtgttgcaa   3000
gcattgttcg tggtggtatt gaagttgttg gtaattatgg tggtcgtccg cgtgttgata   3060
tgccgaaact gctggaactg gttcgtcagg tcgttatga tccgagccgt ctggttaccg    3120
gtcgttttcg tctggaagaa attaatgaag ccgtcaaaat gctggaagaa ggtgaagcaa   3180
ttcgtagcct gattattccg taagatcctc tagagtcgac ctgcaggcat gcaagcttct   3240
gttttggcgg atgagagaag aaattcgtcg cccgccataa actgccaggc atcaaattaa   3300
gcagaaggcc atcctgacgg atggccttt tgcgtttcta caaactcttc ctgtctagca    3360
ggtggcactt tcggggaaa tgtgcgcgga ccccctattt gtttattttt ctaaatacat    3420
tcaaatatgt atccgctcat gctagaaata ttttatctga ttaataagat gatcttcttg   3480
agatcgtttt ggtctgcgcg taatctcttg ctctgaaaac gaaaaaaccg ccttgcaggg   3540
cggtttttcg aaggttctct gagctaccaa ctctttgaac cgaggtaact ggcttggagg   3600
agcgcagtca ccaaaacttg tccttttcagt ttagccttaa ccggcgcatg acttcaagac   3660
taactcctct aaatcaatta ccagtggctg ctgccagtgg tgcttttgca tgtctttccg   3720
ggttggactc aagacgatag ttaccggata aggcgcagcg gtcggactga acgggggtt    3780 cgtgcataca gtccagcttg gagcgaactg cctacccgga actgagtgtc aggcgtggaa   3840
tgagacaaac gcggccataa cagcggaatg acaccggtaa accgaaaggc aggaacagga   3900
gagcgcacga gggagccgcc aggggaaacg cctggtatct ttatagtcct gtcgggtttc   3960
gccaccactg atttgagcgt cagatttcgt gatgcttgtc aggggggcgg agcctatgga   4020
aaaacggctt tgccgcggcc ctctcacttc cctgttaagt atcttcctgg catcttccag   4080
```

```
gaaatctccg ccccgttcgt aagccatttc cgctcgccgc agtcgaacga ccgagcgtag    4140
cgagtcagtg agcgaggaag cggaatatat cctgtatcac atattctgct gacgcaccgg    4200
tgcagccttt tttctcctgc cacatgaagc acttcactga caccctcatc agtgccaaca    4260
tagtaagcca gtatacactc cgctagcgct gatgtccggc ggtgcttttg ccgttacgca    4320
ccaccccgtc agtagctgaa caggagggac agctgataga aacagaagcc actggagcac    4380
ctcaaaaaca ccatcataca ctaaatcagt aagttggcag catcacccga cgcactttgc    4440
gccgaataaa tacctgtgac ggaagatcac ttcgcagaat aaataaatcc tggtgtccct    4500
gttgataccg ggaagccctg gccaactttt tggcgaaaat gagacgttga tcggcacgta    4560
agaggttcca actttcacca taatgaaata agatcactac cgggcgtatt ttttgagtta    4620
tcgagatttt caggagctaa ggaagctaaa atggagaaaa aaatcactgg atataccacc    4680
gttgatatat cccaatggca tcgtaaagaa catttttgagg catttcagtc agttgctcaa    4740
tgtacctata accagaccgt tcagctggat attacggcct ttttaaagac cgtaaagaaa    4800
aataagcaca gtttttatcc ggcctttatt cacattcttg cccgcctgat gaatgctcat    4860
ccggaattcc gtatggcaat gaaagacggt gagctggtga tatgggatag tgttcaccct    4920
tgttacaccg tttttccatga gcaaactgaa acgttttcat cgctctggag tgaataccac    4980
gacgatttcc ggcagtttct acacatatat tcgcaagatg tggcgtgtta cggtgaaaac    5040
ctggcctatt tccctaaagg gtttattgag aatatgtttt tcgtctcagc caatccctgg    5100
gtgagtttca ccagttttga tttaaacgtg gccaatatgg acaacttctt cgcccccgtt    5160
ttcaccatgg gcaaatatta tacgcaaggc gacaaggtgc tgatgccgct ggcgattcag    5220
gttcatcatg ccgtctgtga tggcttccat gtcggcagaa tgcttaatga attacaacag    5280
tactgcgatg agtggcaggg cggggcgtaa ttttttttaag gcagttattg gtgcccttaa    5340
acgcctggtg ctacgcctga ataagtgata taagcggat gaatggcaga aattcgaaag    5400
caaattcgac ccggtcgtcg gttcagggca gggtcgttaa atagccgctt atgtctattg    5460
ctggtttacc ggtttattga ctaccggaag cagtgtgacc gtgtgcttct caaatgcctg    5520
aggccagttt gctcaggctc tccccgtgga ggtaataatt gacgatatga tcatttattc    5580
tgcctcccag agcctgataa aaacggttag cgcttcgtta atacagatgt aggtgttcca    5640
cagggtagcc agcagcatcc tgcgatgcag atccggaaca taatggtgca gggcgcttgt    5700
ttcggcgtgg gtatggtggc aggccccgtg gccgggggac tgttgggcgc tgccggcacc    5760
tgtcctacga gttgcatgat aaagaagaca gtcataagtg cggcgacgat agtcatgccc    5820
cgcgcccacc ggaaggagct accggacagc ggtgcggact gttgtaactc agaataagaa    5880
atgaggccgc tcatggcgtt gactctcagt catagtatcg tggtatcacc ggttggttcc    5940
actctctgtt gcgggcaact tcagcagcac gtagggact tccgcgtttc cagactttac    6000
gaaacacgga aaccgaagac cattcatgtt gttgctcagg tcgcagacgt tttgcagcag    6060
cagtcgcttc acgttcgctc gcgtatcggt gattcattct gctaaccagt aaggcaaccc    6120
cgccagccta gccgggtcct caacgacagg agcacgatca tgcgcacccg tggccaggac    6180
ccaacgctgc ccgagatgcg ccgcgtgcgg ctgctggaga tggcggacgc gatggatatg    6240
ttctgccaag ggttggtttg cgcattcaca gttctccgca agaattgatt ggctccaatt    6300
cttggagtgg tgaatccgtt agcgaggtgc cgccggcttc cattcaggtc gaggtggccc    6360
ggctccatgc accgcgacgc aacgcgggga ggcagacaag gtatagggcg cgcctacaa    6420
```

| | |
|---|---|
| tccatgccaa cccgttccat gtgctcgccg aggcggcata aatcgccgtg acgatcagcg | 6480 |
| gtccagtgat cgaagttagg ctggtaagag ccgcgagcga tccttgaagc tgtccctgat | 6540 |
| ggtcgtcatc tacctgcctg acagcatgg cctgcaacgc gggcatcccg atgccgccgg | 6600 |
| aagcgagaag aatcataatg gggaaggcca tccagcctcg cgtcgcgaac gccagcaaga | 6660 |
| cgtagcccag cgcgtcggcc aattcgcgct aacttacatt aattgcgttg cgctcactgc | 6720 |
| ccgctttcca gtcgggaaac ctgtcgtgcc agctgcatta atgaatcggc caacgcgcgg | 6780 |
| ggagaggcgg tttgcgtatt gggcgccagg gtggtttttc ttttcaccag tgagacgggc | 6840 |
| aacagctgat tgcccttcac cgcctggccc tgagagagtt gcagcaagcg gtccacgctg | 6900 |
| gtttgcccca gcaggcgaaa atcctgtttg atggtggttg acggcgggat ataacatgag | 6960 |
| ctgtcttcgg tatcgtcgta tcccactacc gagatatccg caccaacgcg cagcccggac | 7020 |
| tcggtaatgg cgcgcattgc gcccagcgcc atctgatcgt tggcaaccag catcgcagtg | 7080 |
| ggaacgatgc cctcattcag catttgcatg gtttgttgaa aaccggacat ggcactccag | 7140 |
| tcgccttccc gttccgctat cggctgaatt tgattgcgag tgagatattt atgccagcca | 7200 |
| gccagacgca gacgcgccga gacagaactt aatgggcccg ctaacagcgc gatttgctgg | 7260 |
| tgacccaatg cgaccagatg ctccacgccc agtcgcgtac cgtcttcatg ggagaaaata | 7320 |
| atactgttga tgggtgtctg gtcagagaca tcaagaaata cgccggaac attagtgcag | 7380 |
| gcagcttcca cagcaatggc atcctggtca tccagcggat agttaatgat cagcccactg | 7440 |
| acgcgttgcg cgagaagatt gtgcaccgcc gctttacagg cttcgacgcc gcttcgttct | 7500 |
| accatcgaca ccaccacgct ggcacccagt tgatcggcgc gagatttaat cgccgcgaca | 7560 |
| atttgcgacg gcgcgtgcag ggccagactg gaggtggcaa cgccaatcag caacgactgt | 7620 |
| ttgcccgcca gttgttgtgc cacgcggttg ggaatgtaat tcagctccgc catcgccgct | 7680 |
| tccacttttt cccgcgtttt cgcagaaacg tggctggcct ggttcaccac gcgggaaacg | 7740 |
| gtctgataag agacaccggc atactctgcg acatcgtata acgttactgg tttcacattc | 7800 |
| accaccctga attgactctc ttccgggcgc tatcatgcca taccgcgaaa ggttttgcac | 7860 |
| cattcgatgt tgtcaacgta aatgcatgcc gcttcgcctt cgcgcgcgaa ttggccgcca | 7920 |
| tgccggcgat aatggcctgc ttctcgccga aacgtttggt ggcgggacca gtgacgaagg | 7980 |
| cttgagcgag ggcgtgcaag attccgaata ccgcaagcga caggccgatc atcgtcgcgc | 8040 |
| tccagcgaaa gcggtcctcg ccgaaaatga cccagagcgc tgccggcacc tgtcctacga | 8100 |
| gttgcatgat aaagaagaca gtcataagtg cggcgacgat agtcatgccc cgcgcccacc | 8160 |
| ggaaggagct gactgggttg aaggctctca agggcatcgg cggagcttat cgactgcacg | 8220 |
| gtgcaccaat gcttctggcg tcaggcagcc atcggaagct gtggtatggc tgtgcaggtc | 8280 |
| gtaaatcact gcataattcg tgtcgctcaa ggcgcactcc cgttctggat aatgttttt | 8340 |
| gcgccgacat cataacggtt ctggcaaata ttctgaaatg agctgttgac aattaatcat | 8400 |
| cggctcgtat aatgtgtgga attgtgagcg gataacaatt tcacacagga aacagaa | 8457 |